(12) United States Patent
Thomas et al.

(10) Patent No.: US 9,649,313 B2
(45) Date of Patent: May 16, 2017

(54) USE OF ITK INHIBITORS FOR THE TREATMENT OF CANCER

(71) Applicant: The University of North Carolina at Chapel Hill, Chapel Hill, NC (US)

(72) Inventors: Nancy Thomas, Chapel Hill, NC (US); Kathleen Dorsey, Chapel Hill, NC (US); Sharon Edmiston, Chapel Hill, NC (US); Pamela Groben, Chapel Hill, NC (US); Craig Carson, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/647,354

(22) PCT Filed: Nov. 26, 2013

(86) PCT No.: PCT/US2013/072047
§ 371 (c)(1),
(2) Date: May 26, 2015

(87) PCT Pub. No.: WO2014/082085
PCT Pub. Date: May 30, 2014

(65) Prior Publication Data
US 2016/0000788 A1    Jan. 7, 2016

Related U.S. Application Data

(60) Provisional application No. 61/729,747, filed on Nov. 26, 2012, provisional application No. 61/891,216, filed on Oct. 15, 2013.

(51) Int. Cl.
*A61K 31/519* (2006.01)
*A61K 31/4985* (2006.01)
*A61K 31/4184* (2006.01)
*A61K 31/4155* (2006.01)
*A61K 31/426* (2006.01)

(52) U.S. Cl.
CPC ........ *A61K 31/519* (2013.01); *A61K 31/4155* (2013.01); *A61K 31/4184* (2013.01); *A61K 31/426* (2013.01); *A61K 31/4985* (2013.01)

(58) Field of Classification Search
IPC .......... A61K 31/519,31/426, 31/4155, 31/4985, 31/4184
See application file for complete search history.

(56) References Cited

U.S. PATENT DOCUMENTS 6,710,065 B1 *  3/2004  Camden ............. A61K 31/4184
                                                   514/395
9,115,127 B2 *  8/2015  Boezio ................. C07D 235/30
2005/0197375 A1 * 9/2005  Sircar ................ A61K 31/4184
                                                   514/394

FOREIGN PATENT DOCUMENTS

WO    WO 2005/053690      *  6/2005
WO    WO 2010/35534 A2  * 11/2010

* cited by examiner

*Primary Examiner* — Shirley V Gembeh
(74) *Attorney, Agent, or Firm* — Olive Law Group, PLLC; Nathan P. Letts

(57) ABSTRACT

This invention relates generally to the use of ITK (IL-2 inducible T-cell kinase) inhibitors for the treatment of patients who have melanoma or other solid tumors. Applicants demonstrate that ITK lentiviral small hairpin RNA knockdowns and a small molecule inhibitor can each decrease the proliferation and migration of melanoma cell lines and a small molecule inhibitor can be used to inhibit the growth of melanomas in vivo.

10 Claims, 36 Drawing Sheets

(b)

(b)

(c)

(a)

(c)

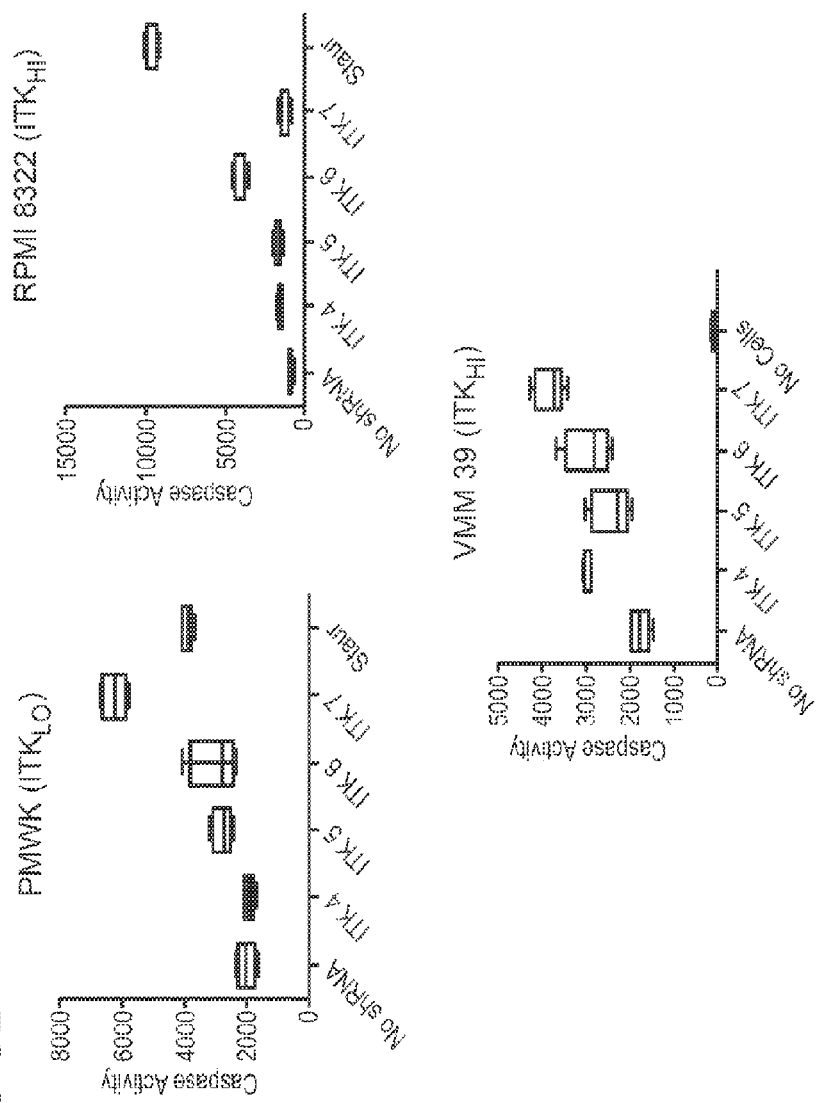

USE OF ITK INHIBITORS FOR THE TREATMENT OF CANCER

CROSS REFERENCE TO RELATED APPLICATIONS

Figure 1:
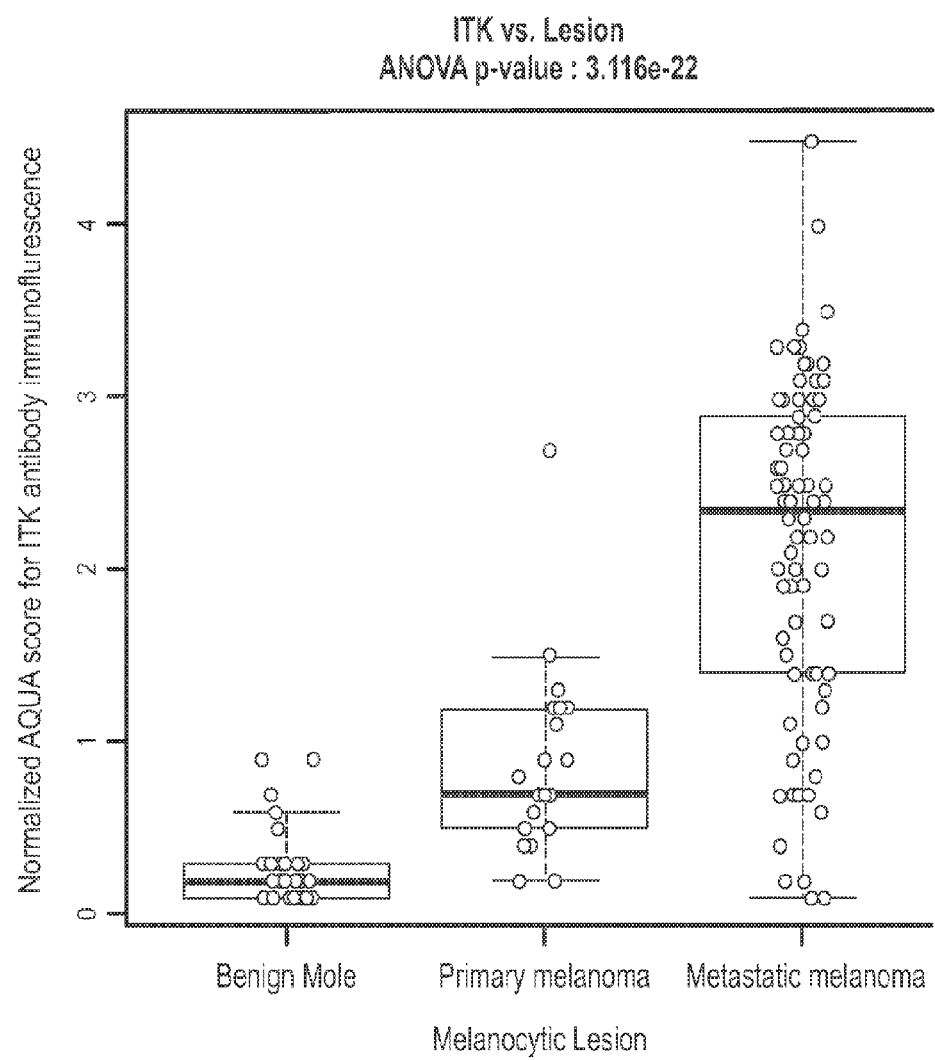

This application is a §371 U.S. National Stage of International Application PCT/US2013/072047, filed Nov. 26, 2013, which claims the benefit of U.S. Ser. No. 61/891,216 filed Oct. 15, 2013, Thomas et al. and U.S. Ser. No. 61/729,747 filed Nov. 26, 2012, Thomas et al., which are hereby incorporated by reference in their entireties.

STATEMENT REGARDING FEDERALLY SPONSORED RESEARCH OR DEVELOPMENT

This invention was made with government support under Grant Nos. CA134368 and CA160138-01 awarded by the National Institutes of Health. The United States Government has certain rights in the invention.

1. FIELD OF THE INVENTION

This invention relates generally to the use of interleukin-2 inducible T-cell kinase (ITK) inhibitors for the treatment of patients who have melanoma or other solid tumors. Applicants demonstrate that ITK small hairpin RNA knockdowns and a small molecule inhibitor can each decrease the proliferation and migration of melanoma cell lines and a small molecule inhibitor can be used to inhibit the growth of melanomas in vivo.

2. BACKGROUND OF THE INVENTION

2.1. Introduction

Melanoma is the seventh most common malignancy in the U.S. The American Cancer Society estimates that approximately 130,000 new cases of melanoma, including 76,250 invasive and 55,560 non-invasive melanomas, will be diagnosed in 2012 and about 9200 people will die of melanoma (Siegel et al., 2012, *CA Cancer J Clin.* 62(1):10-29). If a melanoma is identified and removed before metastasis has occurred, there is a relatively high rate of cure.

Once metastasis has taken place, there are few current therapies that can contain or reverse the adverse effects of malignant melanoma. It is a deadly disease with few systemic treatment options compared to many other cancers. Currently patients diagnosed with an advanced stage of the disease have less than a 15% 5-year survival rate. New inhibitors of BRAFV600E, such as Zelboraf (Bollag 2010) and the CTLA-4 inhibitor Yervoy, have recently been found to influence melanoma survival in clinical trials. Bollag et al., 2010 Nature 467(7315):596-9; Robert et al., 2011 *N Engl J Med* 364(26):2517-26. However, both of these agents are either limited to a small subset of patients or have only short-term clinical benefits due to the rapid development of resistance (Chapman et al., 2011 *N Engl J Med* 364(26): 2507-16; Eggermont and Robert, 2011 *Eur J Cancer* 47: 2150-2156; Hodi et al., 2010 *N Engl J Med* 363(8): p. 711-23). Clearly new therapeutics are needed to enable the effective clinical management of malignant melanoma.

2.2. Companion Diagnostics

Many cancer drugs are approved for use with a companion diagnostic. For example, trastuzumab (Herceptin®) is approved for breast cancer over expressing ERB-B2 and cetuximab (Erbitux®) for patients with wild-type KRAS. Amado et al., 2008, *J Clin Oncol* 26 (10): 1626-1634; Allegra et al., 2009 *J Clin Oncol* 27 2091-2096. Another cancer drug approved for use with a diagnostic is crizotinib (Xalkori®) approved for non-small cell lung cancer (NSCLC) with a fluorescent in situ hybridization (FISH) test for ALK rearrangements (Vysis LSI ALK Dual Color, Break Apart Rearrangement Probe; Abbott Molecular, Abbott Park, Ill.). Shah et al., 2011 *Lancet Oncol* 12 1004-1012; Shaw et al., 2009 *J Clin Oncol* 27 4247-4253. Vemurafenib (Zelboraf®) is approved for melanoma in patients with BRAF V600E mutation (Cobas 4800 BRAF V600 Mutation Test, Roche Molecular Diagnostics, Pleasanton, Calif.). Chapman et al., 2011.

Our earlier work investigating DNA methylation during the progression of melanoma showed that the promoter of ITK was demethylated in primary melanomas and could lead to aberrantly expressed ITK protein in those lesions. Conway et al., 2011 *Pigment Cell Melanoma Res.* 24(2): 352-60. ITK (IL-2 inducible T-cell kinase) is a member of the TEC family of tyrosine kinases that have been implicated in T cell activation, development, and differentiation. ITK has a restricted expression profile, normally found only in mast cells and T lymphocytes, and has been shown to signal in association with the PI3 kinase pathway following activation by the TCR (T Cell Receptor) complex. ITK plays an important role in T cell signaling and the production of various pro-inflammatory cytokines such as IL-2, IL-4, IL-5, IL-10 and IL-13. Drugs targeting ITK are under development for the treatment of diseases related to inflammation disorders such as psoriasis and allergic asthma or for T cell leukemia or lymphoma.

3. SUMMARY OF THE INVENTION

In particular non-limiting embodiments, the present invention provides a method of inhibiting the growth of a solid tumor in a subject which comprises administering an effective amount of a selective interleukin-2 inducible T-cell kinase (ITK) inhibitor to the subject. It may be a therapeutically effective amount or a prophylactically effective amount. The solid tumor may be a breast, a gastric, a head and neck, a kidney, a liver, a lung, a melanoma, a non-small cell lung cancer (NSCLC), a pancreatic, or a uterine tumor. The melanoma tumor may be a primary melanoma tumor or a melanoma metastasis tumor. The breast tumor may be an estrogen receptor negative (ER(−)), a progesterone receptor negative (PR(−)) or an ER(−)PR(−) breast tumor.

The selective interleukin-2 inducible T-cell kinase (ITK) inhibitor may be a 2-amino-5-(thioaryl)thiazole, a 2-amino-5-[(thiomethyl)aryl]thiazole, a 4-arylpyrazolyl indole, a 5-arylpyrazolyl indole, a benzimidazole, an imidazo quinoxalin, or a pyrazolopyrimidine.

The 2-amino-5-(thioaryl)thiazole may be

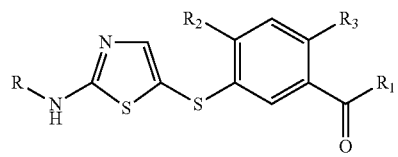

where R is alkenyl, alkyl, alkyl(aryl), alkynyl, aryl, cycloalkyl, cycloaryl, halogen, hydrogen, heteroaryl, or heterocycloalkyl; $R_1$ is alkenyl, alkoxy, alkyl, alkyl(aryl), alkynyl, aryl, cycloalkyl, cycloaryl, halogen, hydrogen, heteroaryl, or heterocycloalkyl; $R_2$ is alkenyl, alkoxy, alkyl, alkyl(aryl), alkynyl, amino, aryl, cycloalkyl, cycloaryl, halogen, hydrogen, hydroxyl, heteroaryl, heterocycloalkyl, or nitro; and R₃ is alkenyl, alkoxy, alkyl, alkyl(aryl), alkynyl, amino, aryl, cycloalkyl, cycloaryl, halogen, hydrogen, hydroxyl, heteroaryl, heterocycloalkyl, or nitro.

The 2-amino-5-(thioaryl)thiazole may be

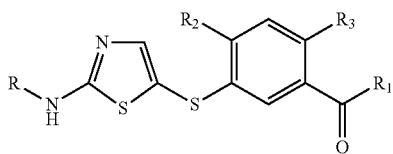

where R is alkyl(aryl), aryl, cycloalkyl, or heteroaryl; R₁ is heterocycloalkyl; R₂ is alkoxy, alkyl, alkyl(aryl), alkynyl, amino, hydrogen, or hydroxy; and R₃ is alkoxy, alkyl, alkyl(aryl), alkynyl, amino, hydrogen, or hydroxy.

The 2-amino-5-[(thiomethyl)aryl]thiazole may be

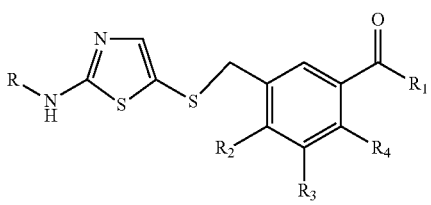

where R is alkenyl, alkyl, alkyl(aryl), alkynyl, aryl, cycloaryl, halogen, hydrogen, or heteroaryl; R₁ is alkenyl, alkoxy, alkyl, alkyl(aryl), alkynyl, aryl, cycloalkyl, cycloaryl, halogen, hydrogen, heteroaryl, or heterocycloalkyl; R₂ is alkenyl, alkoxy, alkyl, alkyl(aryl), alkynyl, amino, aryl, cycloalkyl, cycloaryl, halogen, hydrogen, hydroxyl, heteroaryl, heterocycloalkyl, or nitro; R₃ is alkenyl, alkoxy, alkyl, alkyl(aryl), alkynyl, amino, aryl, cycloalkyl, cycloaryl, halogen, hydrogen, hydroxyl, heteroaryl, heterocycloalkyl, or nitro; and R₄ is alkenyl, alkoxy, alkyl, alkyl(aryl), alkynyl, amino, aryl, cycloalkyl, cycloaryl, halogen, hydrogen, hydroxyl, heteroaryl, heterocycloalkyl, or nitro.

The 2-amino-5-[(thiomethyl)aryl]thiazole may be

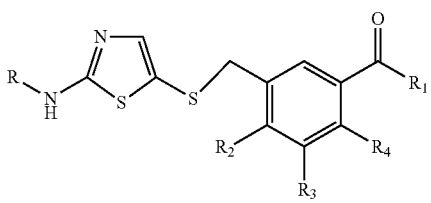

where R is alkyl(aryl), aryl, cycloalkyl, or heteroaryl; R₁ is heterocycloalkyl; R₂ is alkoxy, alkyl, alkyl(aryl), alkynyl, amino, halogen, hydrogen, or hydroxy; R₃ is alkoxy, alkyl, alkyl(aryl), alkynyl, amino, halogen, hydrogen, or hydroxy; and R₄ is alkoxy, alkyl, alkyl(aryl), alkynyl, amino, halogen, hydrogen, or hydroxy.

The 4-arylpyrazolyl indole may be

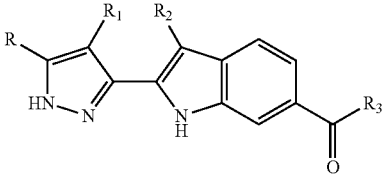

where R is alkenyl, alkoxy, alkyl, alkyl(aryl), alkynyl, amino, aryl, cycloalkyl, cycloaryl, halogen, hydrogen, hydroxyl, heteroaryl, heterocycloalkyl, or nitro; R₁ is alkenyl, alkoxy, alkyl, alkyl(aryl), alkynyl, amino, aryl, cycloalkyl, cycloaryl, halogen, hydrogen, hydroxyl, heteroaryl, heterocycloalkyl, or nitro; R₂ is alkenyl, alkoxy, alkyl, alkyl(aryl), alkynyl, amino, aryl, cycloalkyl, cycloaryl, halogen, hydrogen, hydroxyl, heteroaryl, heterocycloalkyl, or nitro; and R₃ is alkenyl, alkoxy, alkyl, alkyl (aryl), alkynyl, amino, aryl, cycloalkyl, cycloaryl, halogen, hydrogen, hydroxyl, heteroaryl, heterocycloalkyl, or nitro.

The 4-arylpyrazolyl indole may be

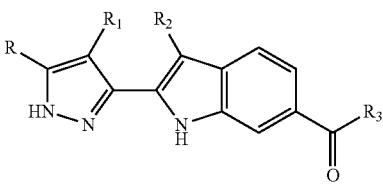

where R is alkyl(aryl), aryl, or hydrogen; R₁ is alkyl(aryl), aryl, or hydrogen; R₂ is alkyl, alkyl(aryl), or hydrogen; and R₃ is alkyl, alkyl(aryl), amino, or heterocycloalkyl.

The benzimidazole may be

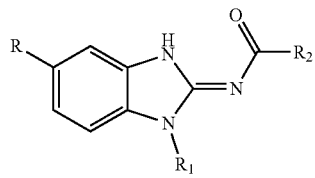

where R is alkenyl, alkoxy, alkyl, alkyl(aryl), alkynyl, amino, aryl, cycloalkyl, cycloaryl, halogen, hydrogen, hydroxyl, heteroaryl, heterocycloalkyl, or nitro; R₁ is alkenyl, alkoxy, alkyl, alkyl(aryl), alkynyl, amino, aryl, cycloalkyl, cycloaryl, halogen, hydrogen, hydroxyl, heteroaryl, heterocycloalkyl, or nitro; and R₂ is alkenyl, alkoxy, alkyl, alkyl(aryl), alkynyl, amino, aryl, cycloalkyl, cycloaryl, halogen, hydrogen, hydroxyl, heteroaryl, heterocycloalkyl, nitro, thiophenyl cycloalkyl, thiophenyl heteroaryl or thiophenyl heterocycloalkyl.

The benzimidazole may be

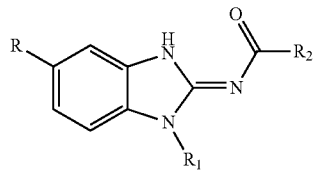

where R is alkyl(aryl), heteroaryl, or heterocycloalkyl; $R_1$ is alkyl; and $R_2$ is aryl, heteroaryl, heterocycloalkyl, thiophenyl cycloalkyl, thiophenyl heteroaryl or thiophenyl heterocycloalkyl.

The benzimidazole may be

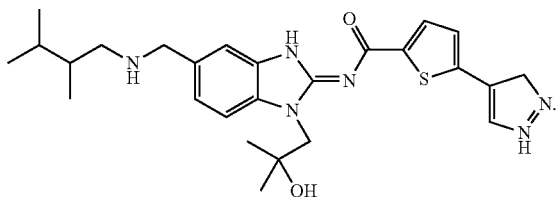 [SMILES: CC(C)C(C)CNCc1ccc2c(c1)[nH]/c(=N\C(=O)c1ccc(C3=CN=NC3)s1)n2CC(C)(C)O]

The imidazo quinoxalin may be

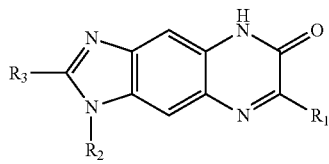

where $R_1$ is alkenyl, alkoxy, alkyl, alkyl(aryl), alkynyl, amino, aryl, cycloalkyl, cycloaryl, halogen, hydrogen, hydroxyl, heteroaryl, and heterocycloalkyl; $R_2$ is alkenyl, alkoxy, alkyl, alkyl(aryl), alkynyl, amino, aryl, cycloalkyl, cycloaryl, halogen, hydrogen, hydroxyl, heteroaryl, heterocycloalkyl, or nitro; and $R_3$ is alkenyl, alkoxy, alkyl, alkyl(aryl), alkynyl, amino, aryl, cycloalkyl, cycloaryl, halogen, hydrogen, hydroxyl, heteroaryl, heterocycloalkyl, or nitro.

The pyrazolopyrimidine may be

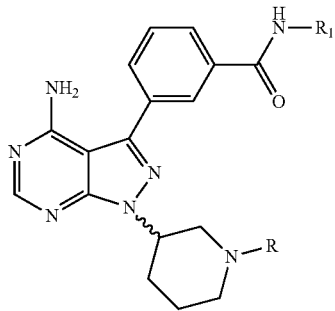

where R is alkenyl, alkoxy, alkyl, alkyl(aryl), alkynyl, amino, aryl, cyano, cycloalkyl, cycloaryl, halogen, hydrogen, hydroxyl, heteroaryl, heterocycloalkyl, keto alkenyl, keto heterocycloalkenyl, keto alkynyl; and $R_1$ is alkenyl, alkoxy, alkyl, alkyl(aryl), alkynyl, amino, aryl, cycloalkyl, cycloaryl, halogen, hydrogen, hydroxyl, heteroaryl, and heterocycloalkyl.

The invention also provides method of maintaining a cell in a G0/G1 phase of the cell cycle, which comprises administering to the cell an effective amount of a selective interleukin-2 inducible T-cell kinase (ITK) inhibitor, e.g., a melanoma cell or a breast cancer cell.

The invention also provides a method of inhibiting melanoma cell motility in a subject which comprises administering an effective amount of a selective interleukin-2 inducible T-cell kinase (ITK) inhibitor to the subject. The melanoma cell may be a primary melanoma cell or a melanoma metastasis cell. In these methods, selective interleukin-2 inducible T-cell kinase (ITK) inhibitor may be one of the compounds above, e.g., a 2-amino-5-(thioaryl)thiazole, a 2-amino-5-[(thiomethyl)aryl]thiazole, a 4-arylpyrazolyl indole, a 5-arylpyrazolyl indole, a benzimidazole, an imidazo quinoxalin, or a pyrazolopyrimidine.

The invention also provides a method of monitoring treatment response of a solid tumor cancer patient receiving an selective interleukin-2 inducible T-cell kinase (ITK) inhibitor which comprises measuring a level of an ITK biomarker in an appropriate sample from the patient so as to monitor the treatment response of the solid tumor cancer patient. The ITK biomarker is a specific antibody for ITK, a specific antibody for phosphor-ITK, or a nucleic acid that specifically binds ITK.

4. BRIEF DESCRIPTION OF THE FIGURES

FIG. 1. Dual fluorescent immunohistochemistry and AQUA of ITK in the nevus-melanoma progression pathway. ITK protein levels for 30 benign nevi (moles), 22 primary melanomas, and 86 metastatic melanomas were studied quantitatively using dual fluorescent immunohistochemistry and Automated Quantitative Analysis (AQUA) technology as described. The two antigens that were detected were ITK and S100 and AQUA analysis using S100 signals to define melanocytic cells, was performed to quantify the expression of ITK in melanocytic lesions. The results demonstrated that median levels of ITK expression significantly differ across the populations of nevi, primary melanomas and metastatic melanomas (p<0.001). No ITK staining was observed in the normal skin specimens including melanocytes (data not shown).

Figure 2:
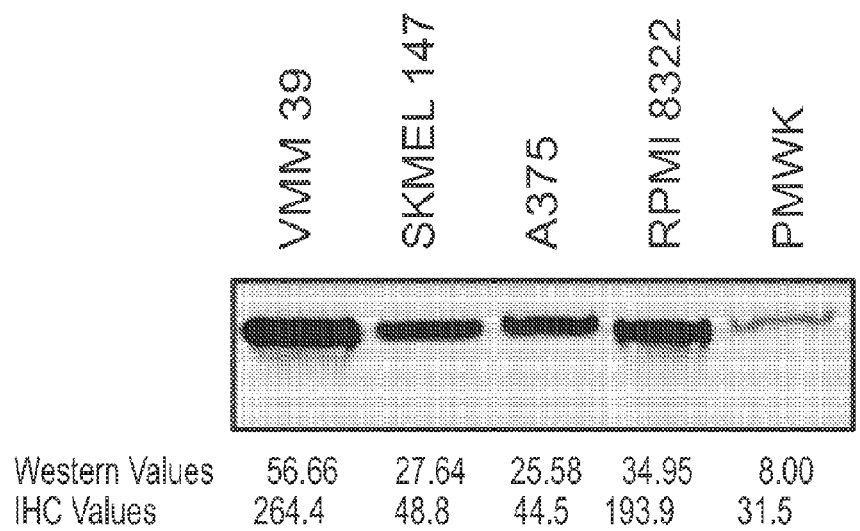

FIG. 2. Expression of ITK in cell lines by western compared to fluorescent immunohistochemistry. FIG. 2 shows ITK levels in melanoma cell lines comparing quantification on a Western blot using cell lysates with AQUA scores by fluorescent immunohistochemistry of the cells embedded in a TMA. While the absolute numbers and dynamic ranges differ, the relative order of the cell lines for levels of ITK expression are the same. Both measures were performed using rabbit monoclonal anti ITK (Y401).

Figure 3A:
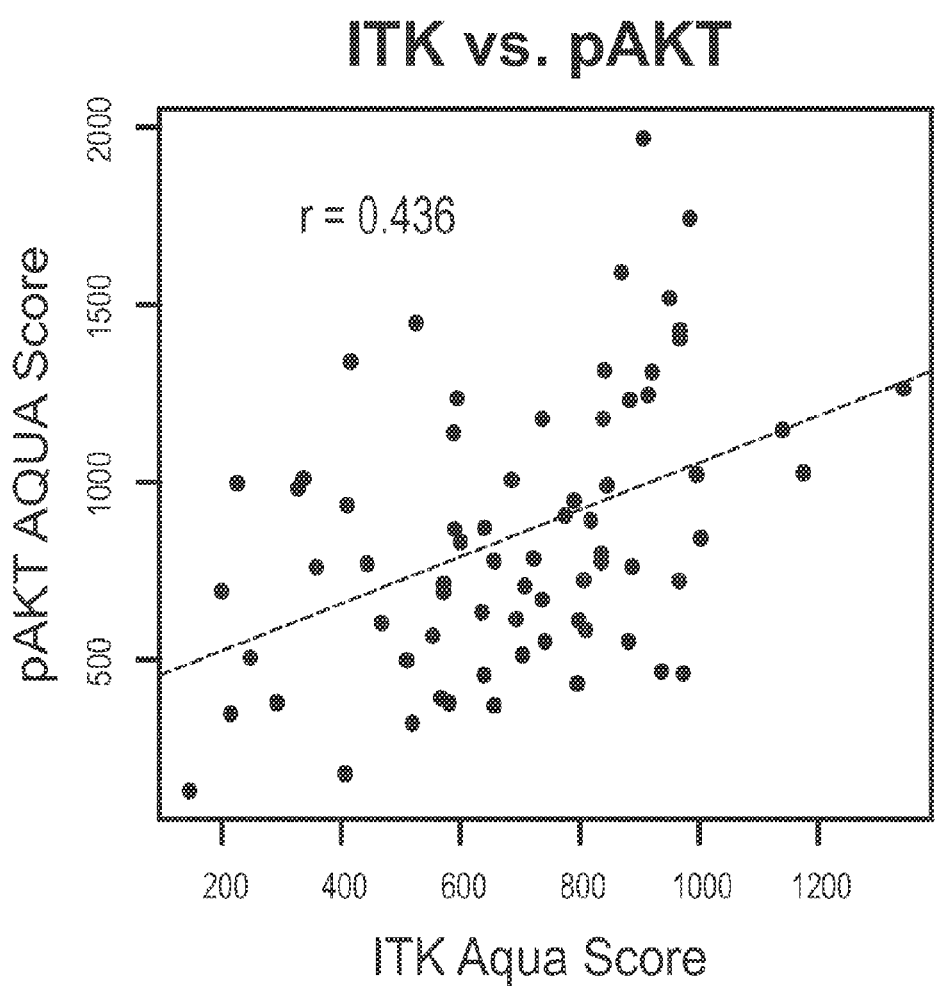
Figure 3B:
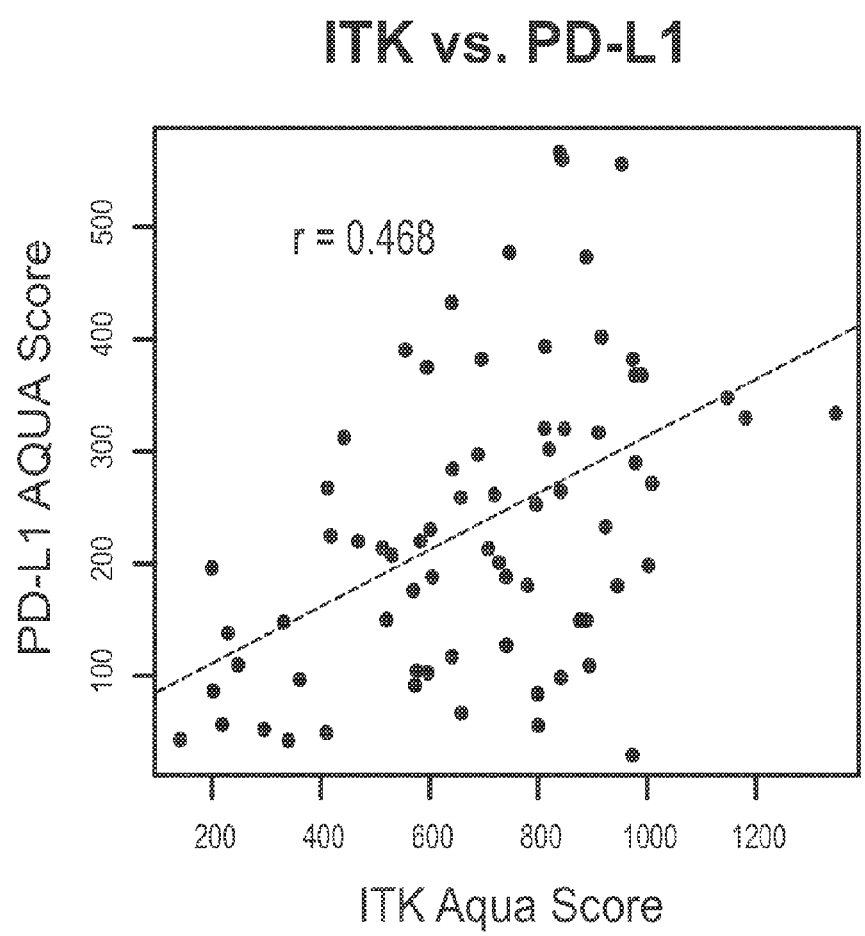

FIG. 3A-B. Correlation of ITK expression with pAKT and PD-L1. FIG. 3A) IHC for phospho AKT (pAKT) and for ITK were performed on serial TMA sections. The correlation was performed using a Pearson correlation with the AQUA score for both the ITK and the pAKT values as described in the materials and methods. FIG. 3B) Correlation between ITK and PD-L protein levels in metastatic melanomas (n=70). Tissue microarray sections underwent sequential dual stains for ITK/S100 and PD-L1/S100 and were counterstained with DAPI and visualized using dual color IF. ITK and PD-L expression were each quantified in S100-positive cells using AQUA. IHC for phospho ERK (pERK) was performed and analyzed as for FIG. 3A. Plots were generated for both nuclear and cytoplasmic pERK and the two were similar. There was no correlation with pERK and ITK.

Figure 4A:
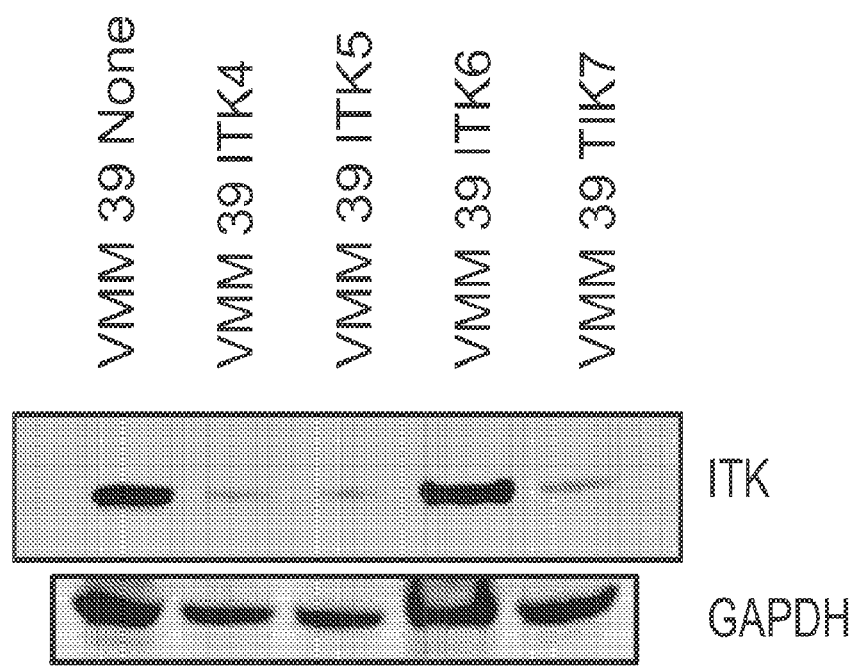
Figure 4B:
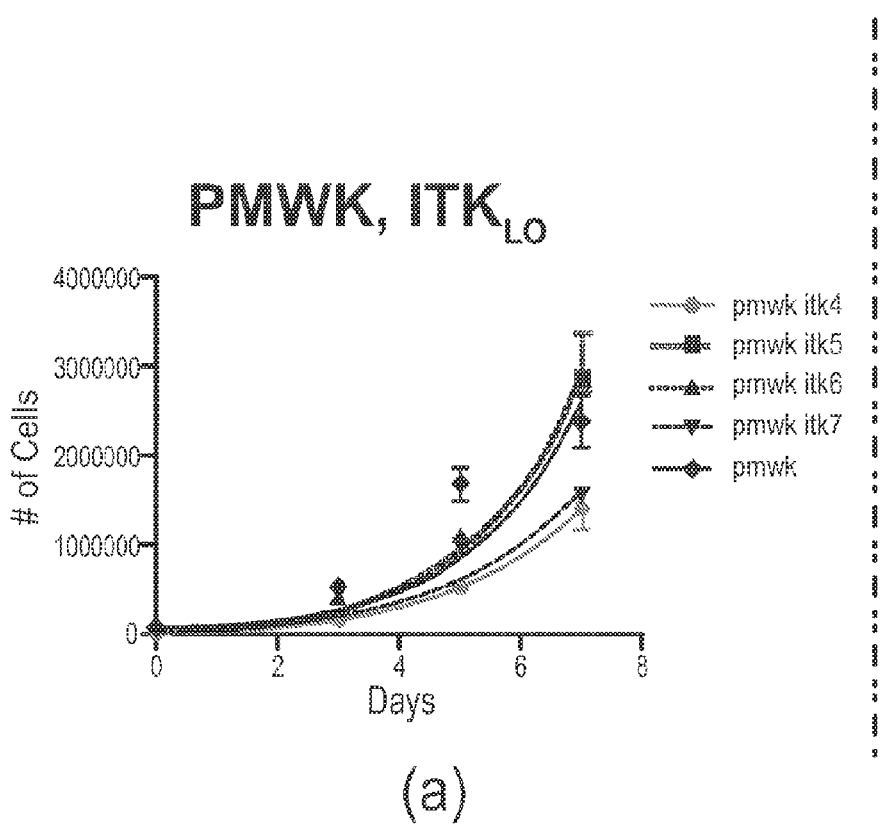
Figure 4B:
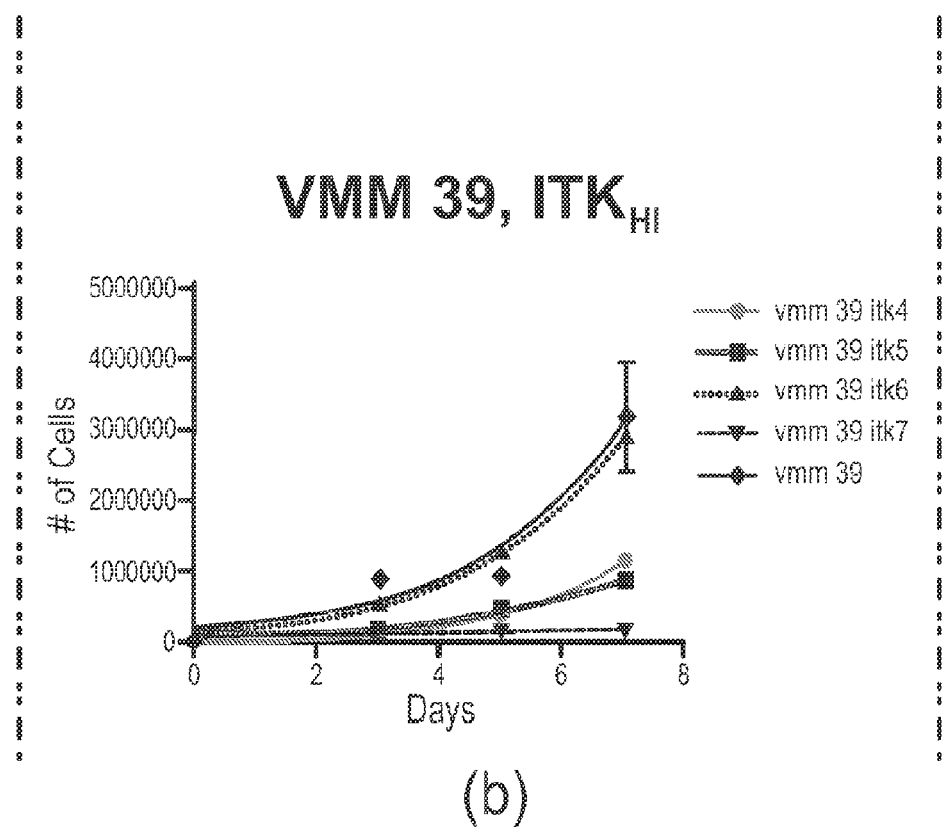
Figure 4B:
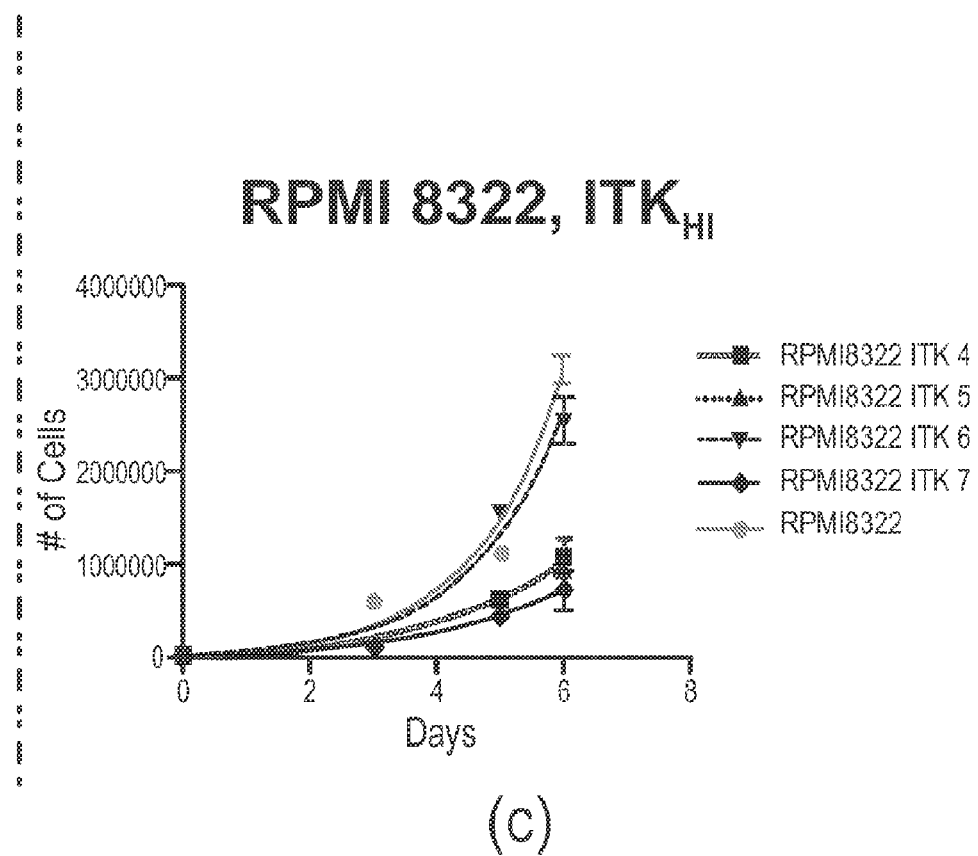
Figure 4C:
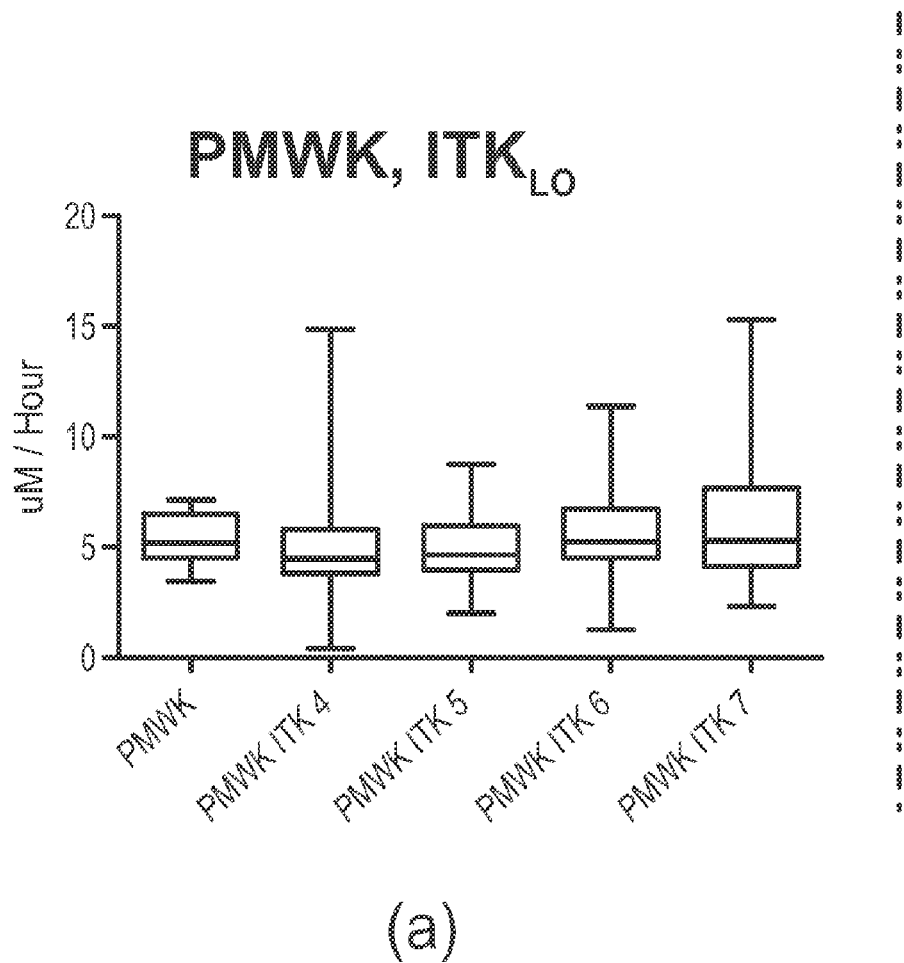
Figure 4C:
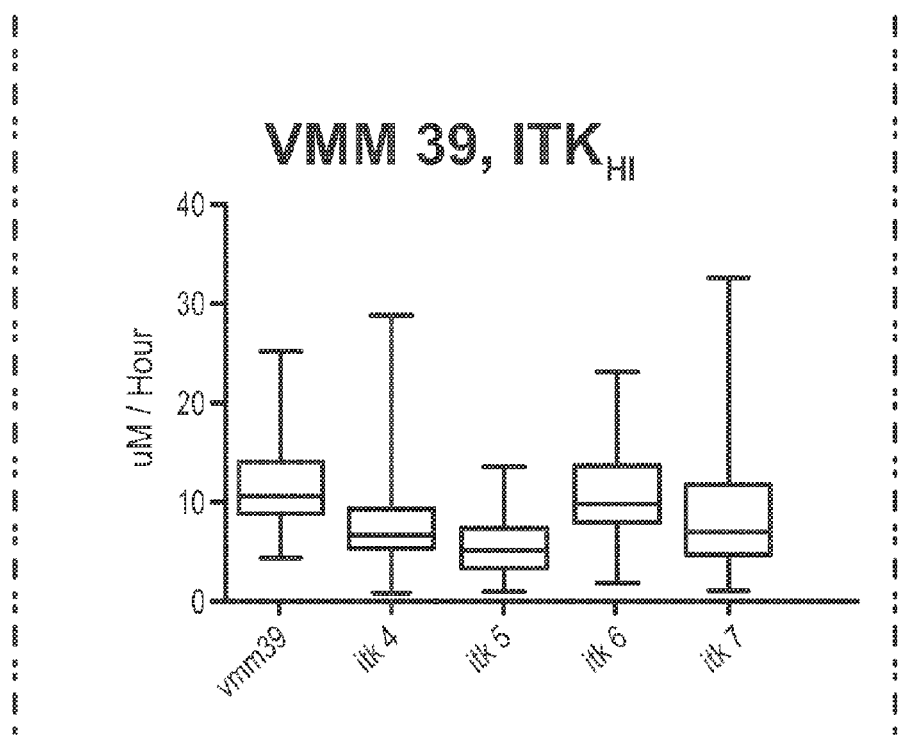
Figure 4C:
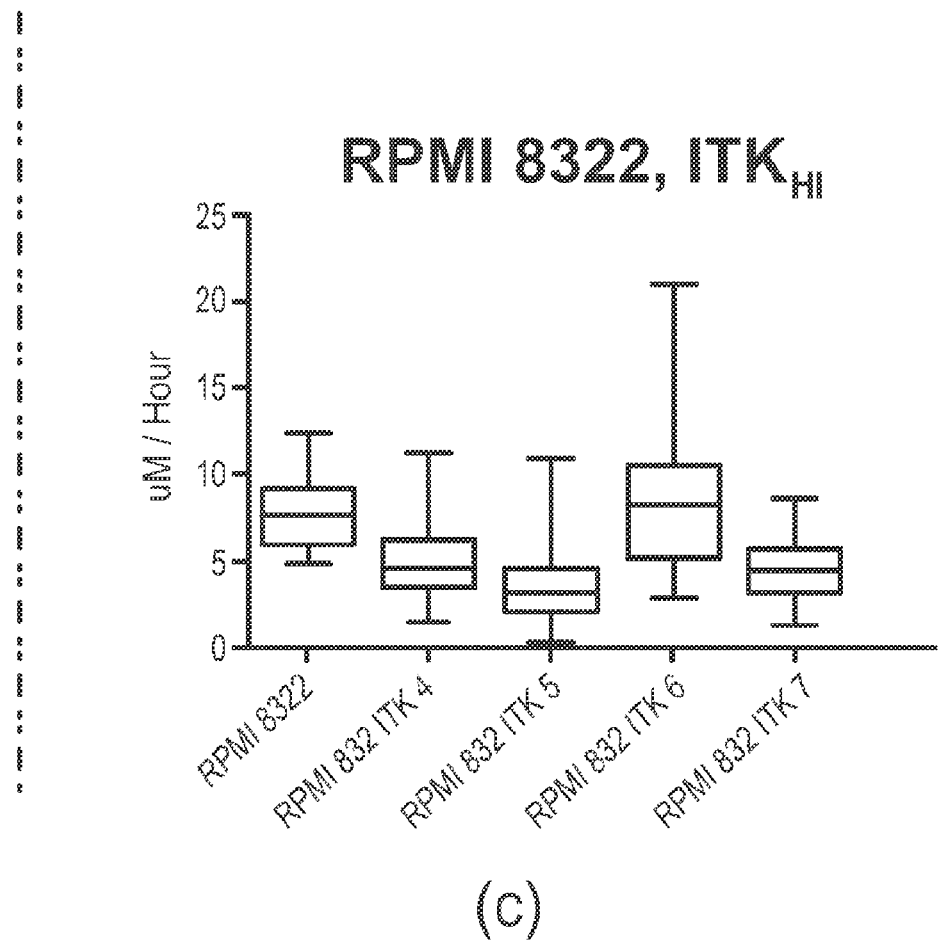
Figure 4D:
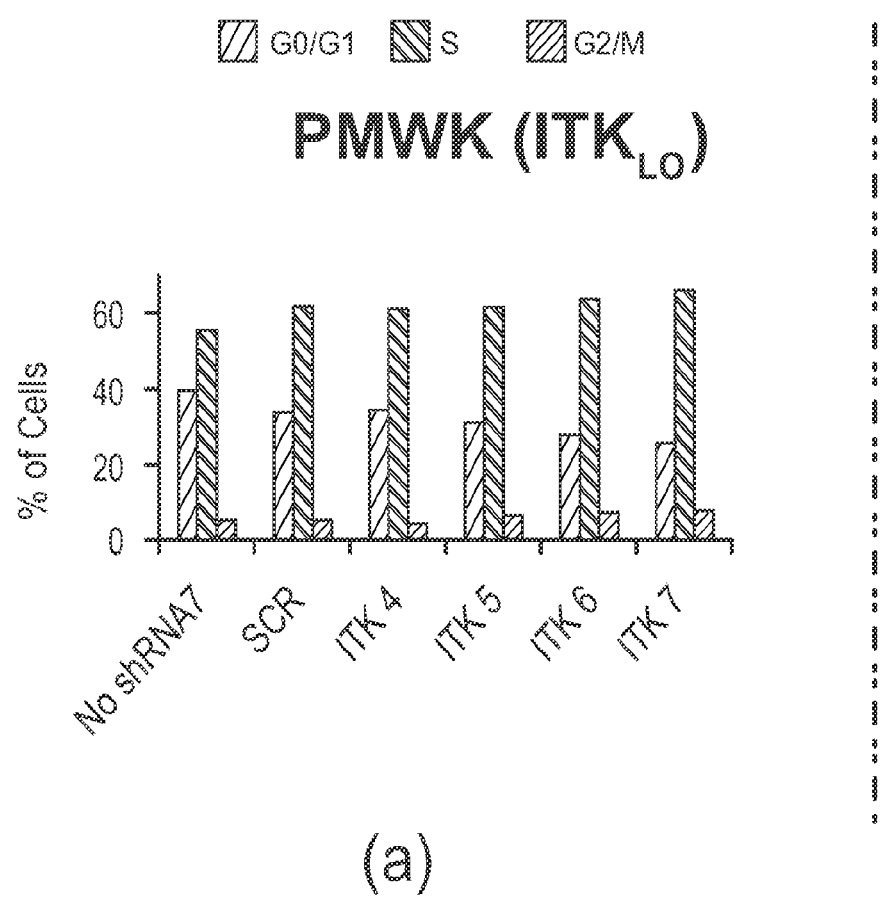
Figure 4D:
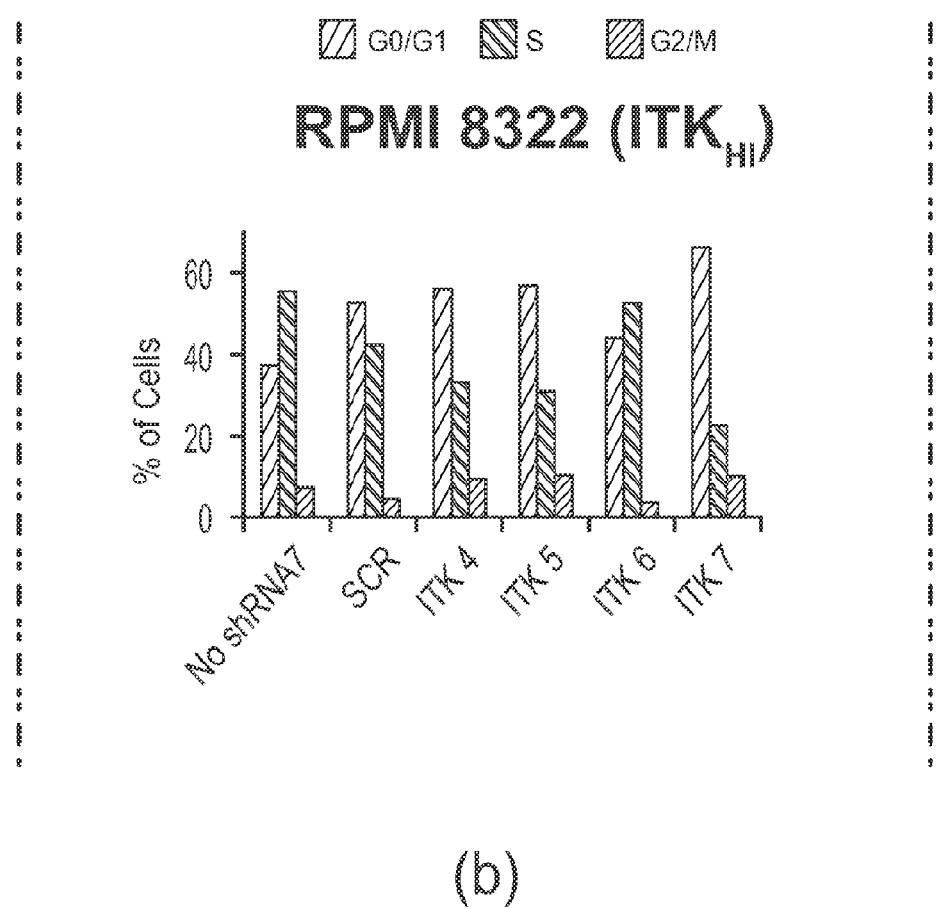
Figure 4D:
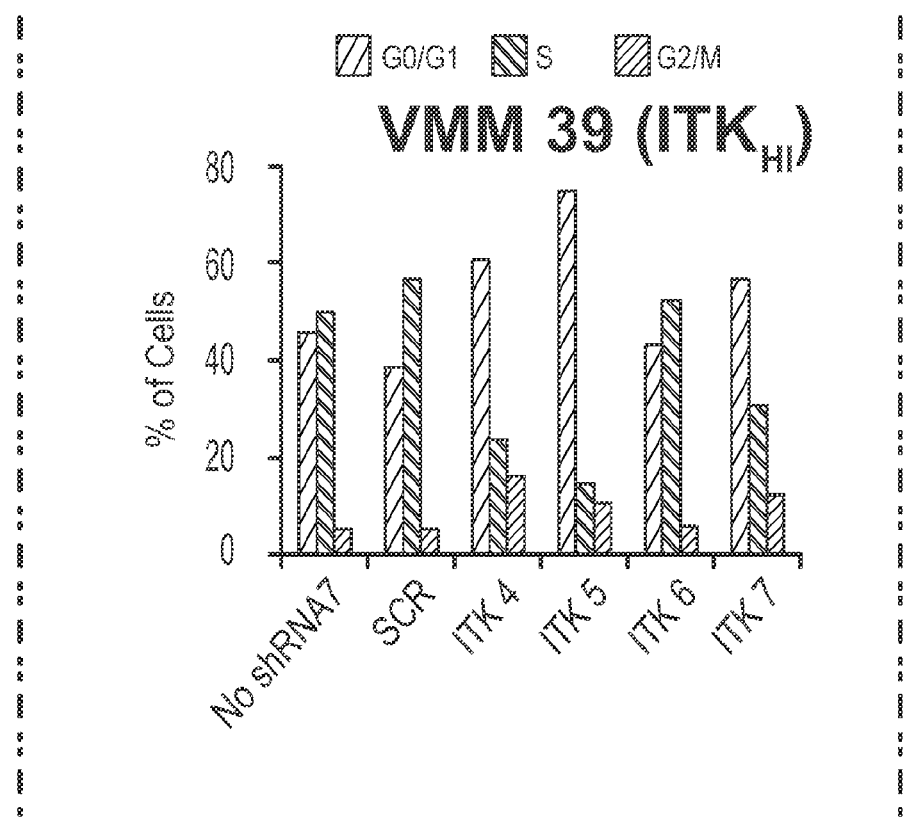
Figure 4E:
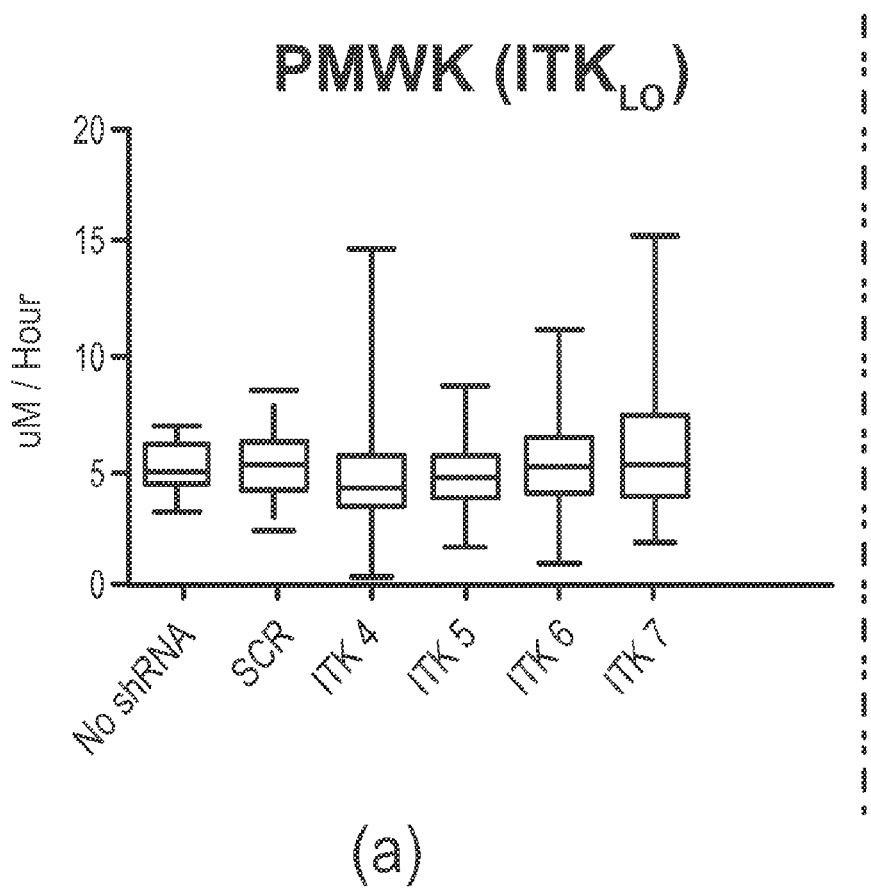
Figure 4E:
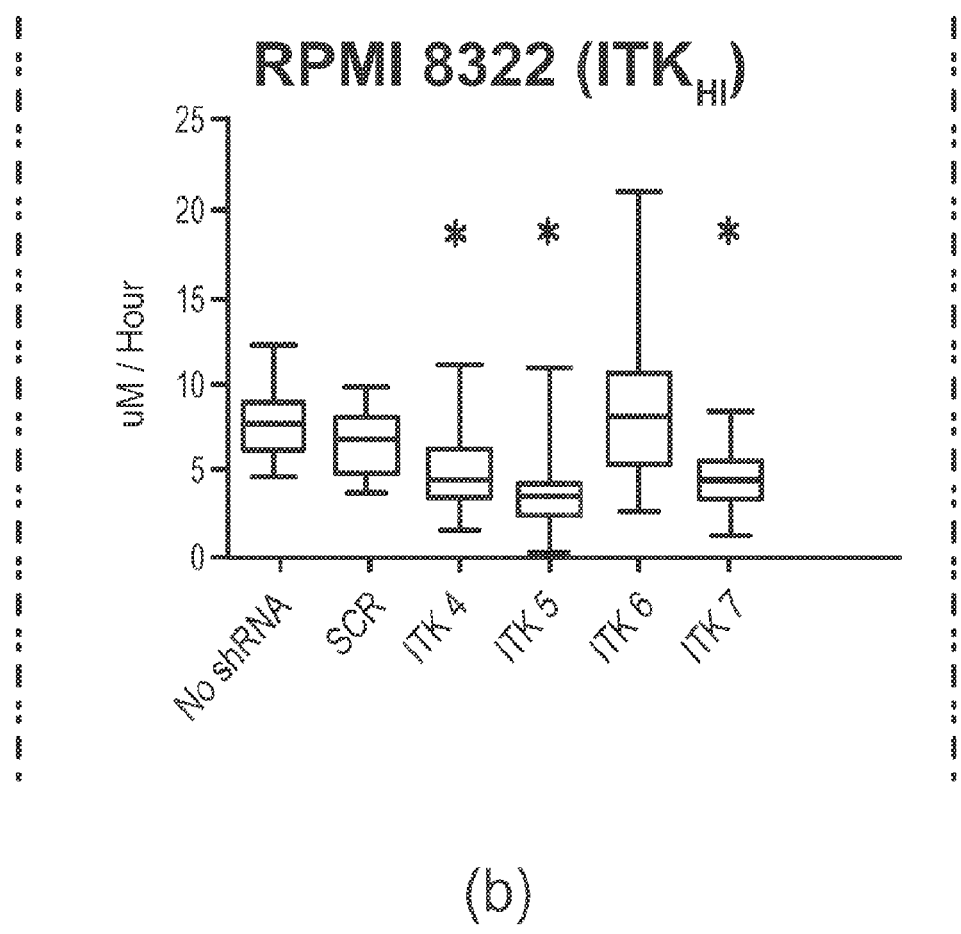
Figure 4E:
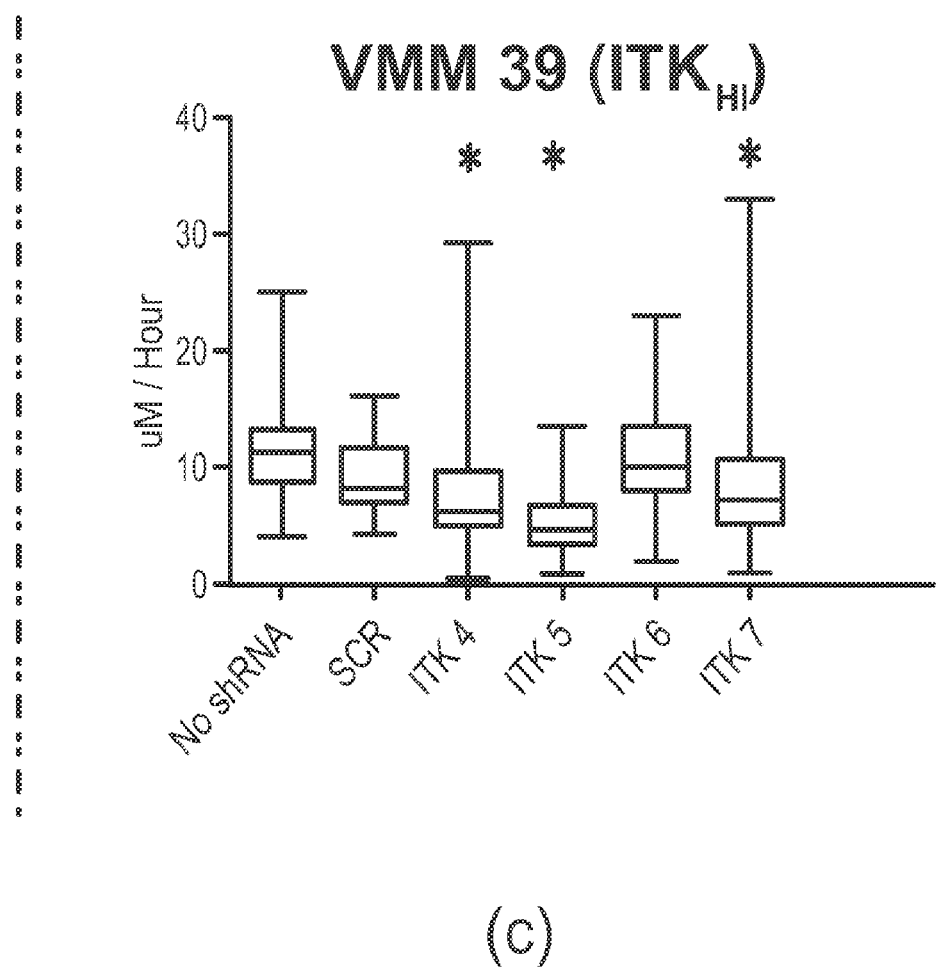

FIG. 4A-4E. Effects of ITK knockdown on proliferation and motility of melanoma cells. FIG. 4A) Western of lysates of VMM 39 containing each of the four shRNA constructs using rabbit monoclonal anti ITK (Y401). FIG. 4B) The four shRNA lentiviral constructs were used to transduce three melanoma cell lines, PMWK ($ITK_{LO}$), VMM 39 ($ITK_{HI}$), and RPMI 8322 ($ITK_{HI}$). 50,000 cells were placed into each well of a 6 well plate, which was then counted 3, 5, and 6, or 7 days after plating to assess the proliferation rates of the different cell lines. FIG. 4C) Single Cell Motility assays were performed on three different melanoma cell lines, PMWK, VMM 39, and RPMI 8322. Each melanoma cell line was transduced with the four shRNA lentiviral constructs producing a total of 12 cell lines. 10,000 cells were plated on fibronectin coated glass bottom dishes. Pictures were taken once every 40 minutes for 16 hours. FIG. 4D) Cell cycle analysis of PMWK, VMM 39, and RPMI 8322 cells that have been transduced with various shRNAs. Cells were harvested after 3 hours of incubation with 5-ethynyl-2'-deoxyuridine (EdU). EdU incorporation and DNA content with FxCycle Violet were analyzed using flow cytometry. Illustrated in this panel are the percentages of cells in G0/G1 (low DNA and EdU content), S (high EdU and low-to-medium DNA content), and G2/M (Low EdU and high DNA content). FIG. 4E) Single-cell motility analysis of PMWK, VMM 39, and RPMI 8322 that have been transduced with various shRNAs. At least 50 cells were tracked for each cell line and the average motility rate was determined. Shown with asterisks are the shRNA-transduced melanoma cell lines with significant impairment in motility ($P<0.001$ one-way ANOVA following Bonferroni adjustments for multiple comparisons).

Figure 5A:
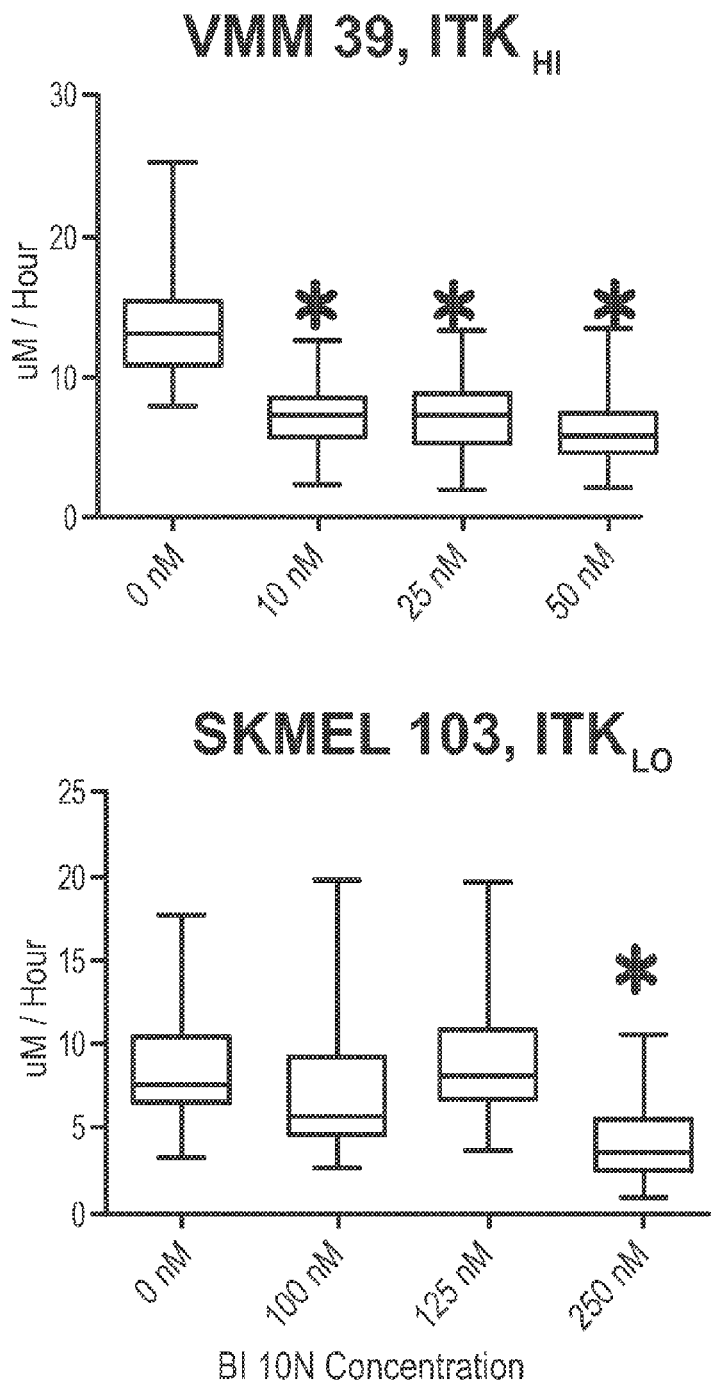
Figure 5A:
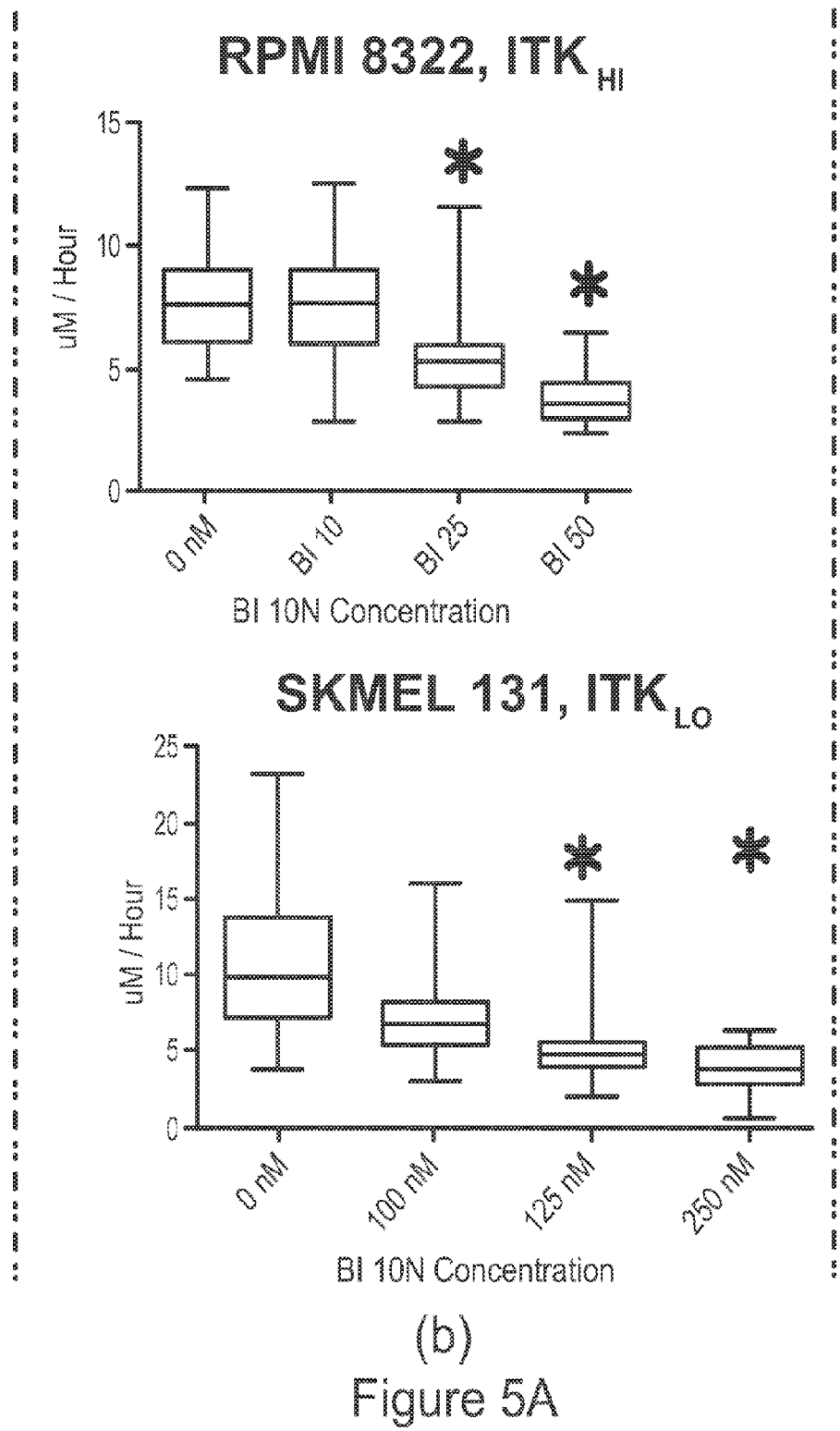
Figure 5A:
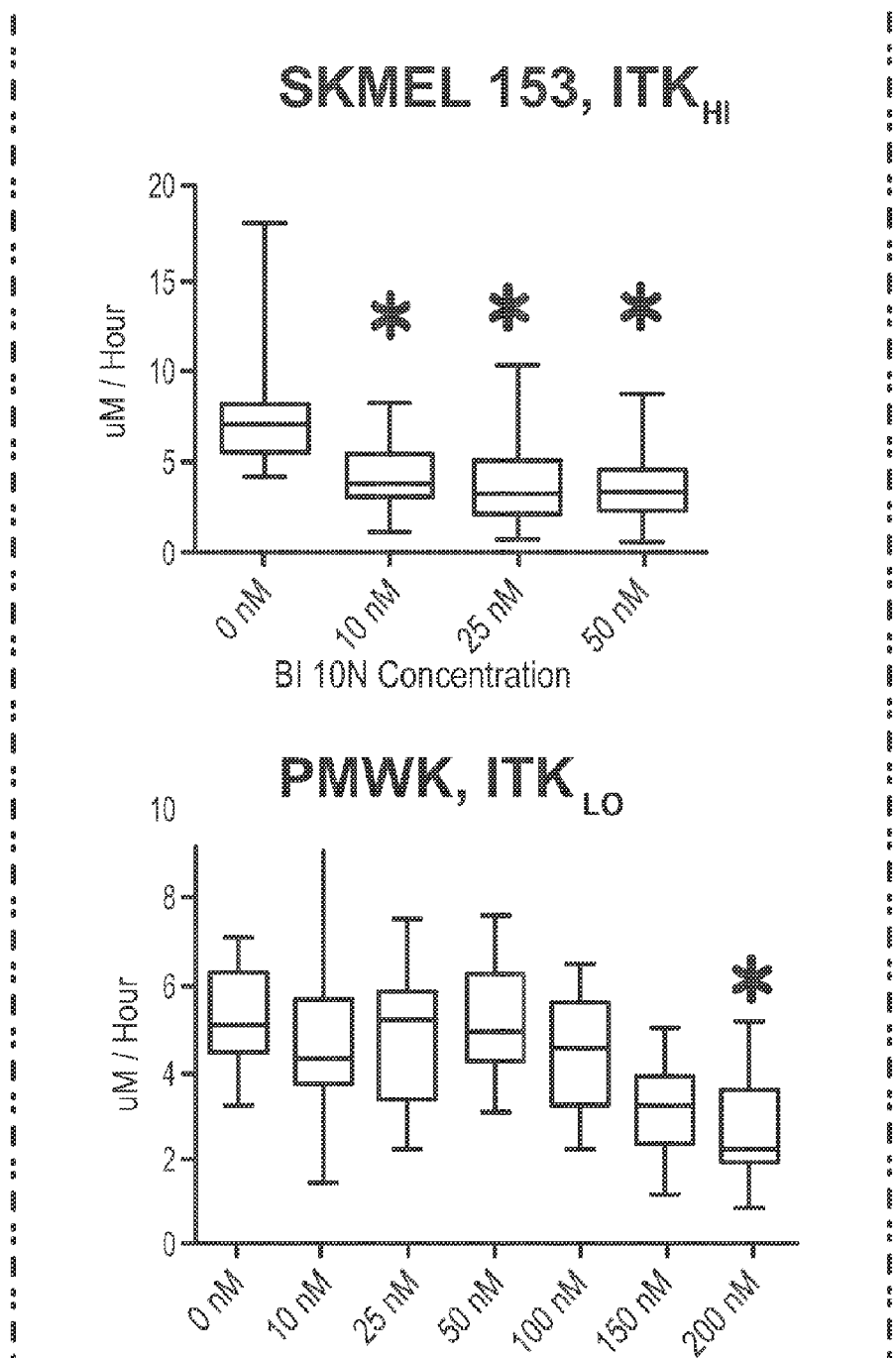
Figure 5A:
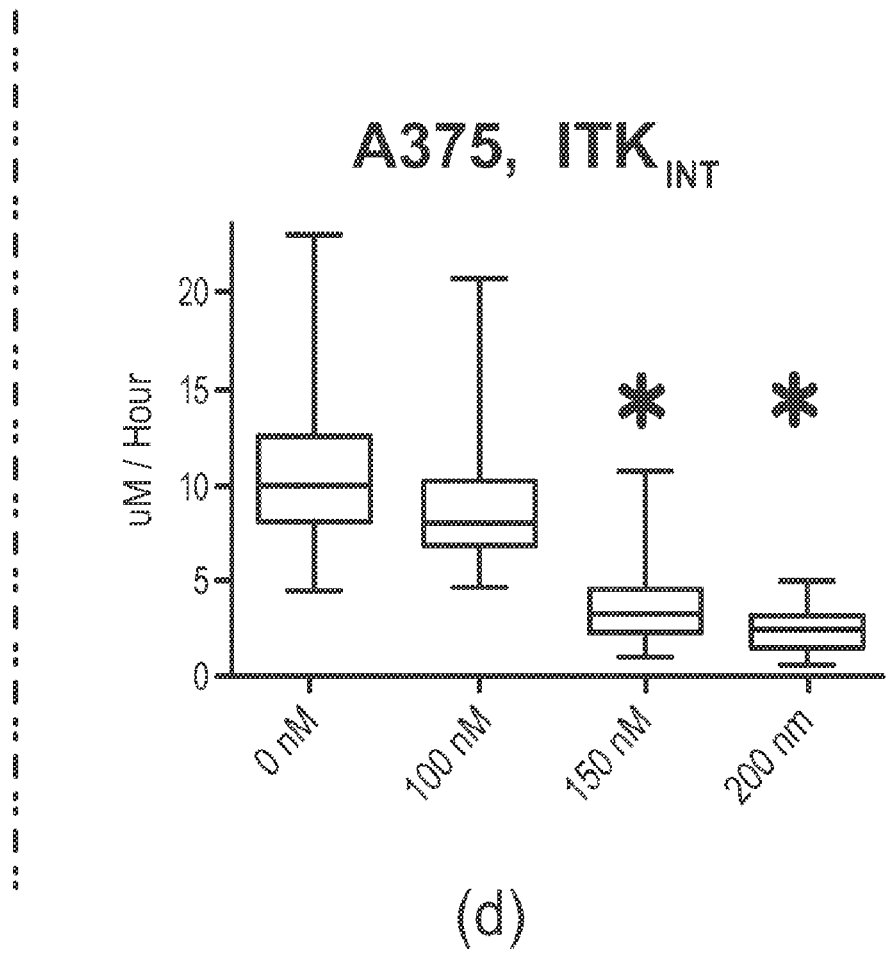
Figure 5B:
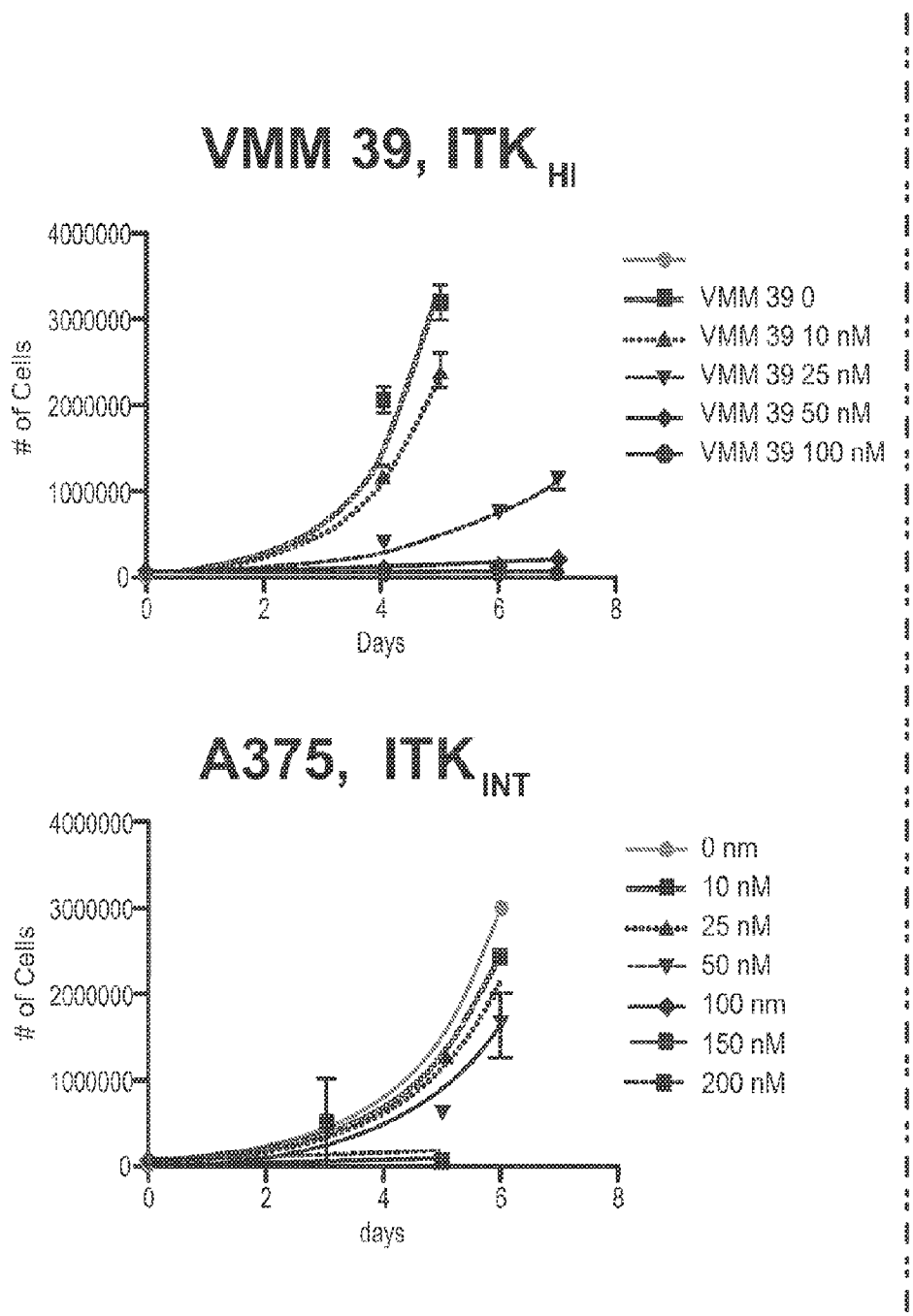
Figure 5B:
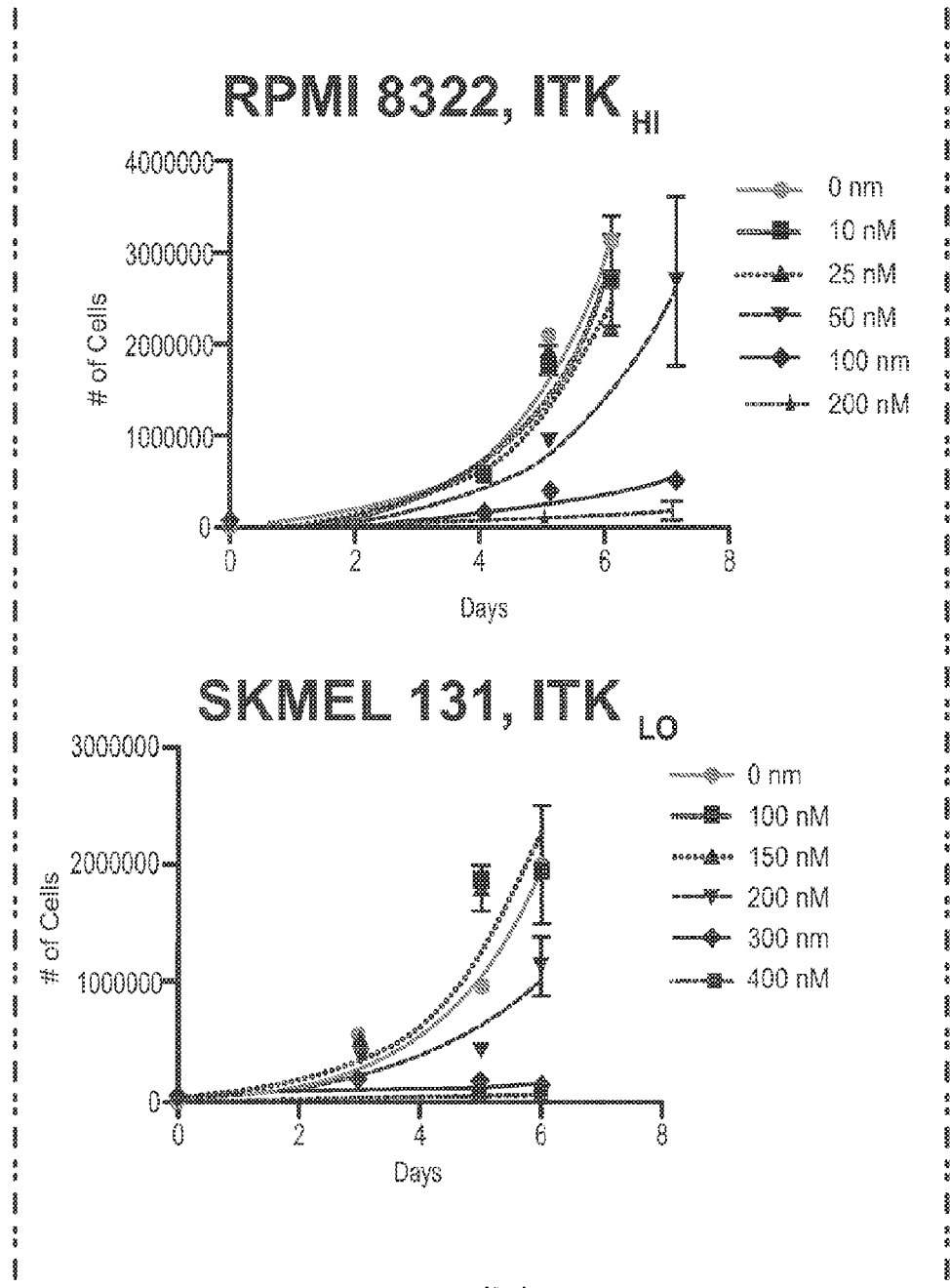
Figure 5B:
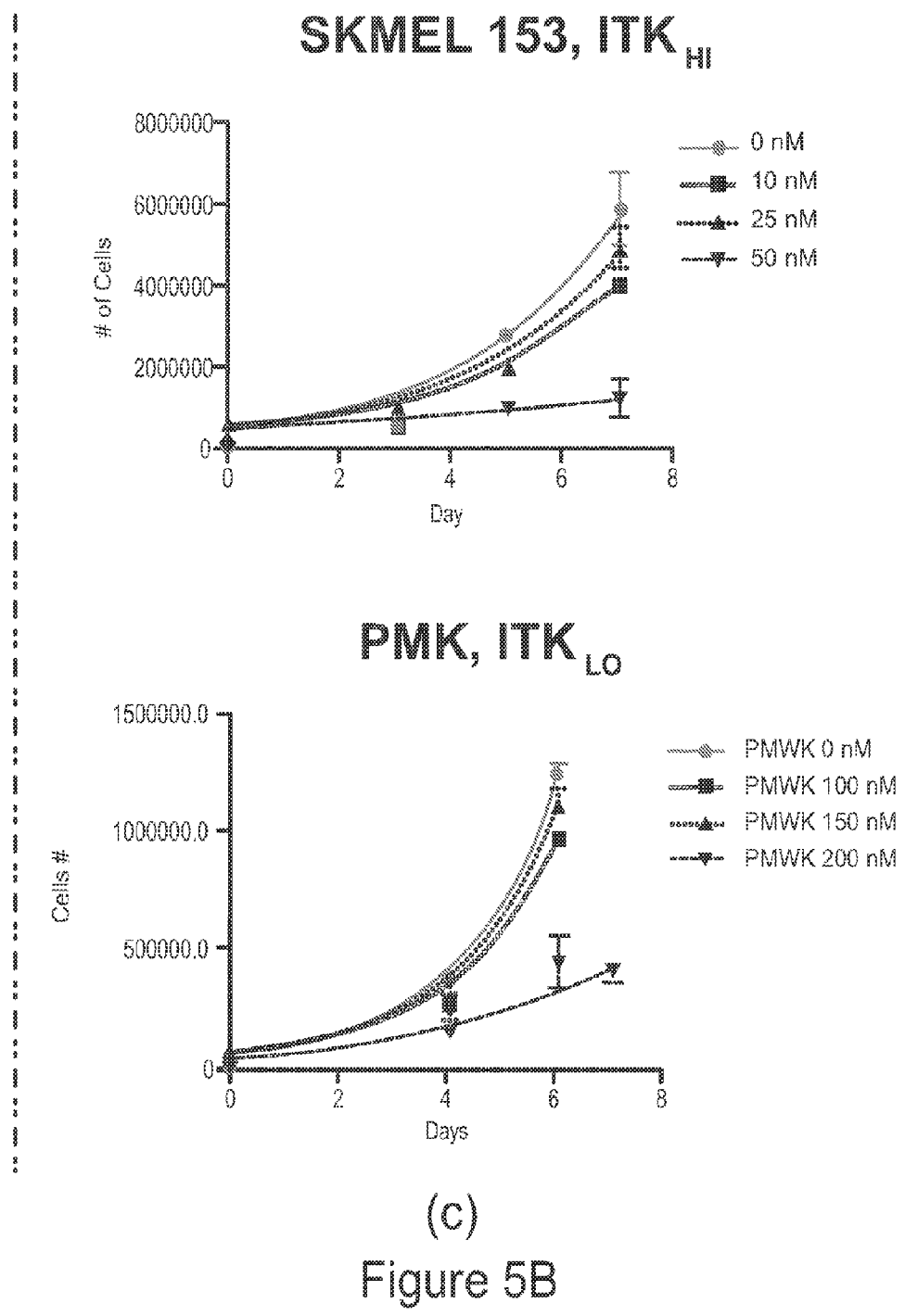
Figure 5C:
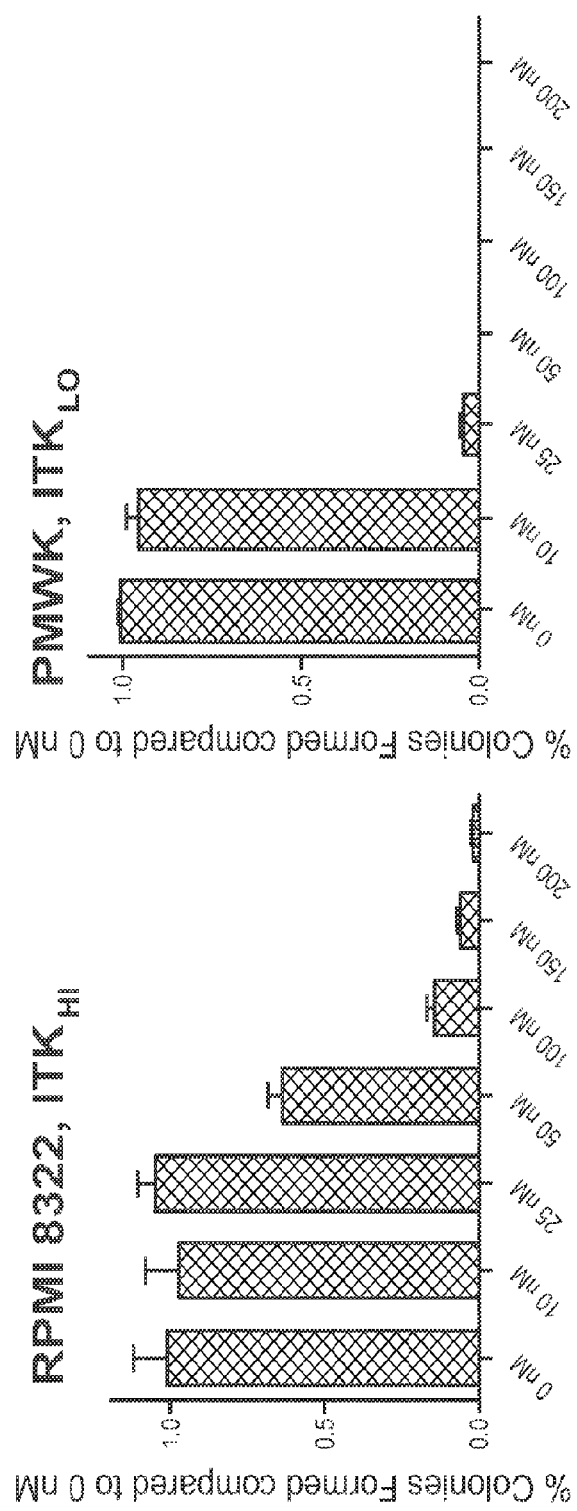
Figure 5D:
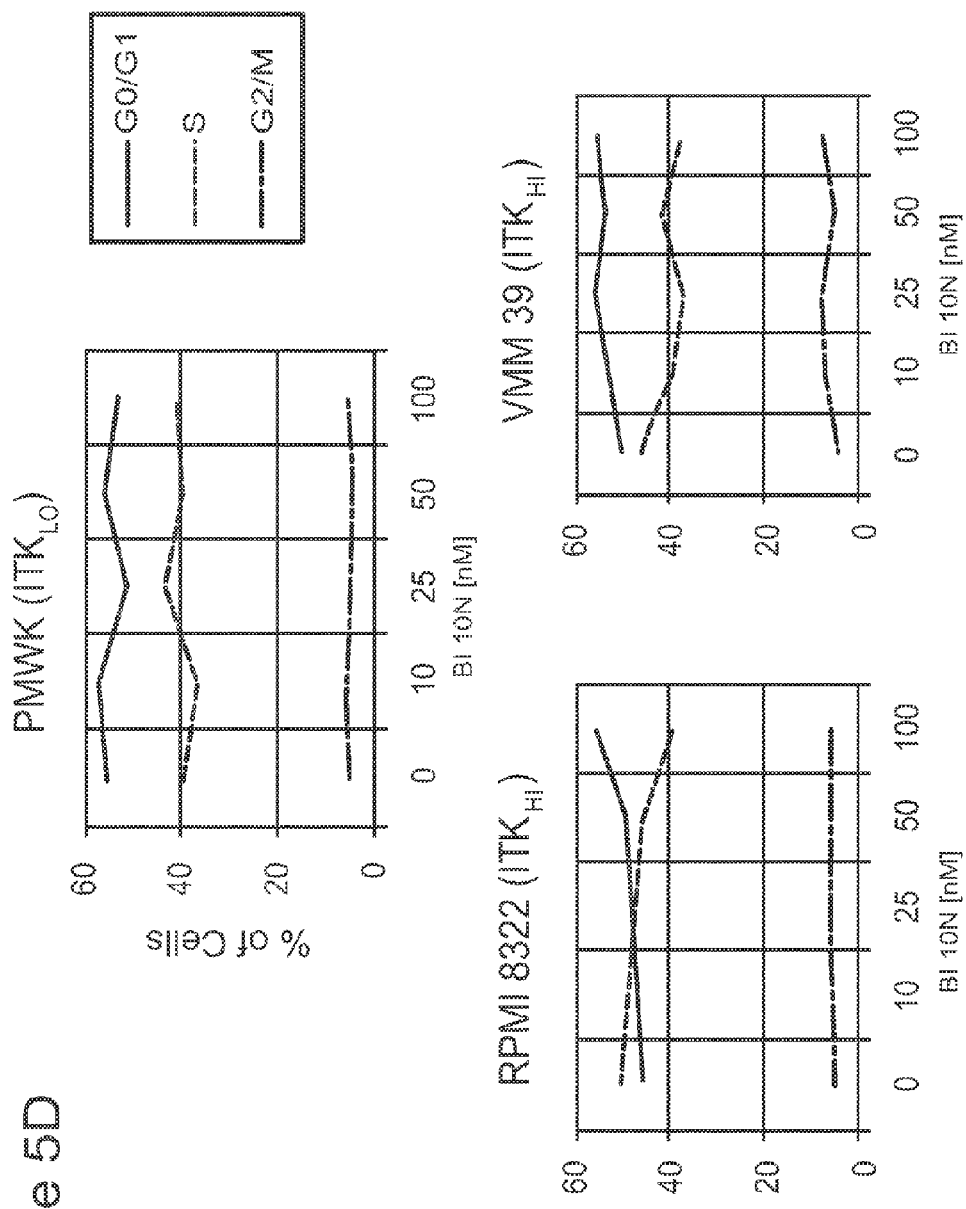

FIG. 5A-5C. Effects of BI 10N inhibitor on proliferation and motility of melanoma cells. FIG. 5A) Cell motility assays were performed as described in FIG. 4A-4E; however, the inhibitor BI 10N was added to the media to decrease ITK kinase activity in parental cell lines instead of using the shRNA ITK knockdown cell lines. BI 10N was added to the media 24 hours prior to the start of the motility assay and the VivaView camera system was used to image cellular motility of the melanoma cells as described previously. FIG. 5B) The proliferation assays were completed as described in FIG. 4A-4E, substituting the BI 10N compound for the shRNA. Cells were trypsinized and counted using the Invitrogen Countess. Fifty thousand cells were placed into each well of a 6 well plate and BI 10N was added to the indicated concentrations. The cells were counted with the Invitrogen Countess at 3, 5, and 6 or 7 days after plating to assess the proliferation rates of the different cell lines in the presence of BI 10N. FIG. 5C) Both $ITK_{HI}$ (RPMI 8322) and $ITK_{LO}$ (PMWK) melanoma cell lines were grown in the presence of BI 10N (10-200 nM) in soft agar. In 24-well cell culture plates 2,500 cells per well were added to a 1.4% agarose solution. The agarose and cell solution was then poured on top of a solidified base agar. The cells were incubated at 37° C. for three to four weeks to ensure adequate growth before analysis. FIG. 5D) Cell cycle analysis of PMWK, VMM 39, and RPMI 8322 cells that have been treated with increasing concentrations of BI 10N. Following 3 days of BI 10N treatment, the cells were incubated with EdU for 3 hours and were subsequently assessed for 5-ethynyl-2'-deoxyuridine (EdU) incorporation rate and DNA content with FxCycle Violet. Shown in this panel are the percentages of cells in G0/G1 (low DNA and EdU content), S (high EdU and low-to-medium DNA content), and G2/M (Low EdU and high DNA content)

Figure 6B:
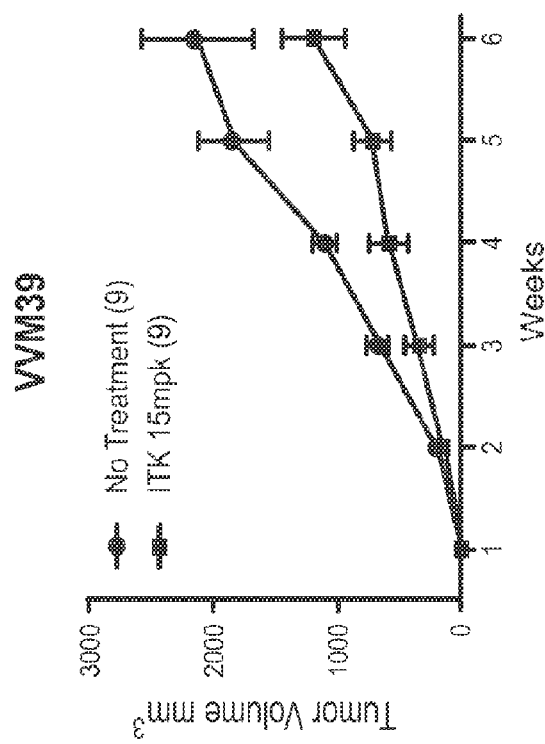
Figure 6A:
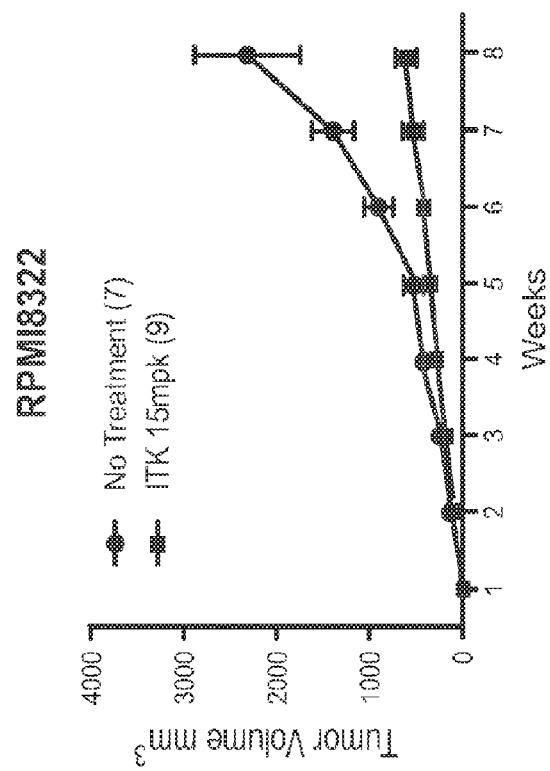
Figure 6C:
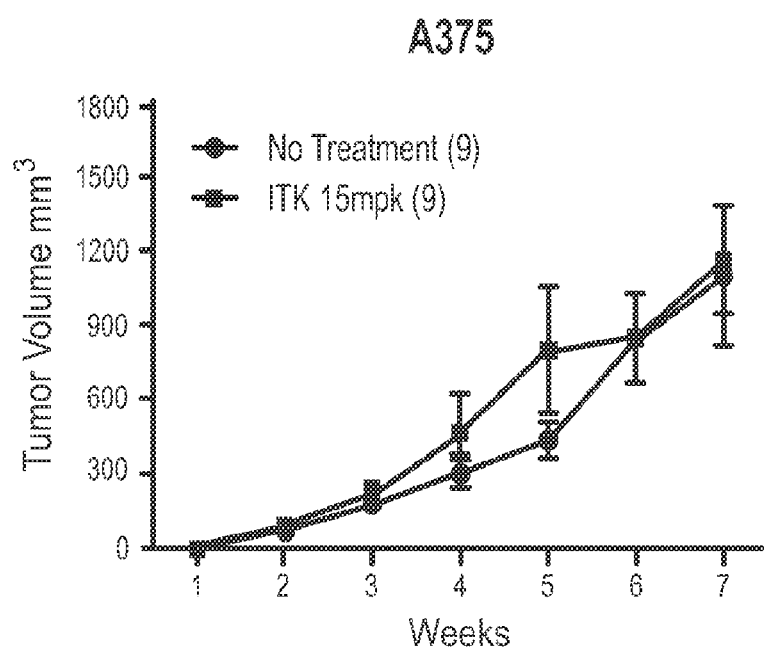
Figure 6D:
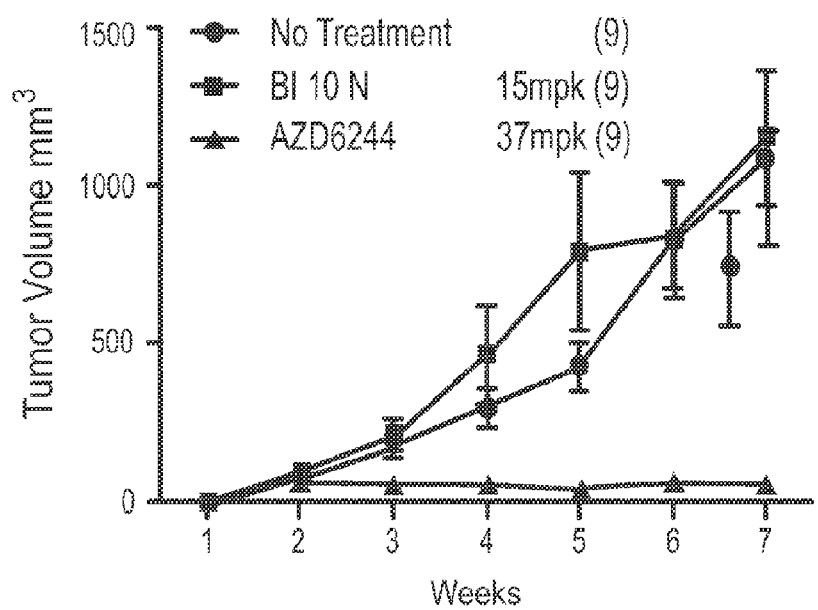
Figure 6E:
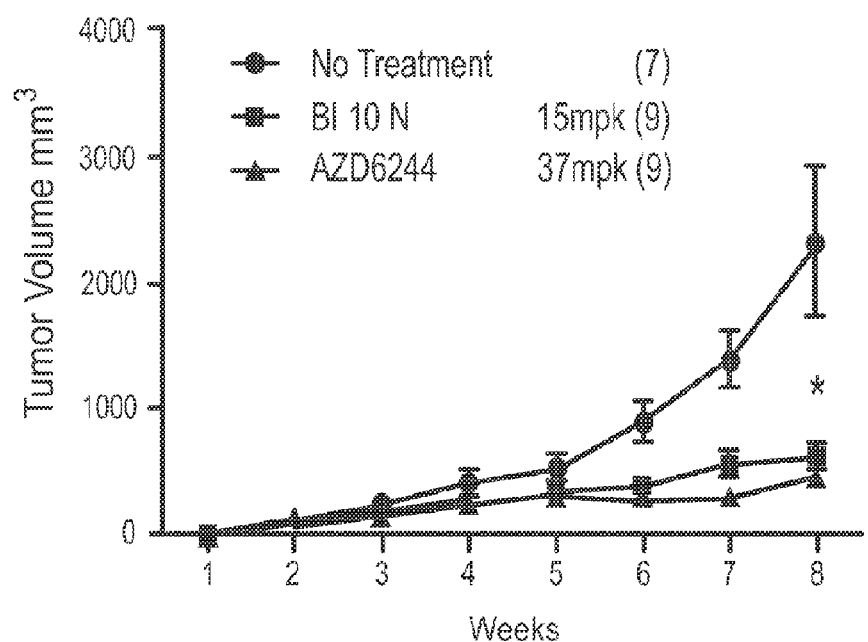
Figure 6F:
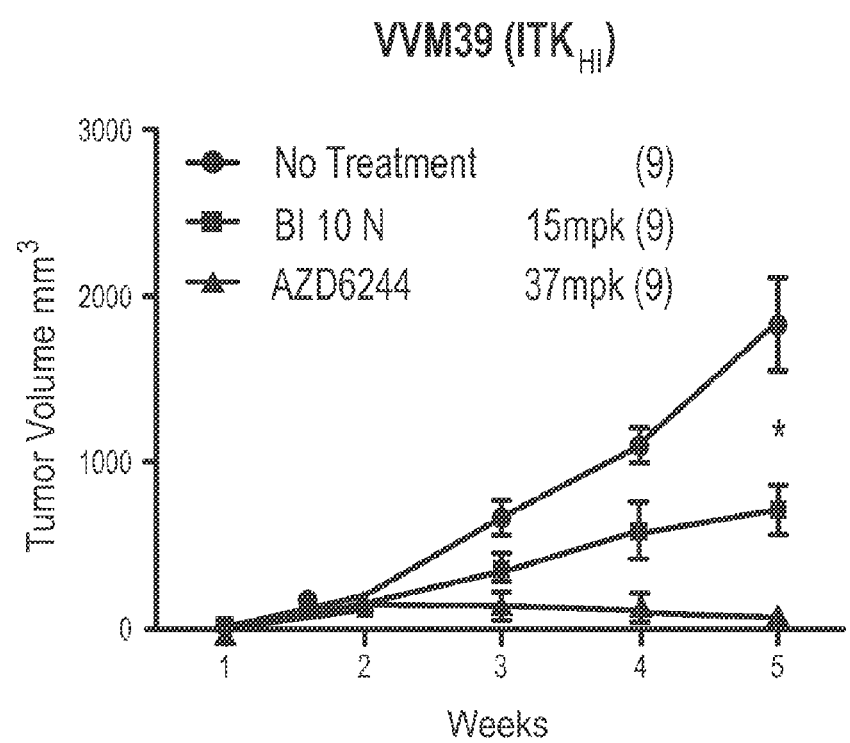

FIG. 6A-6F. Effects of BI 10N inhibitor on growth of melanoma xenografts in vivo. FIG. 6A-6C) Cell lines RPMI 8322 ($ITK_{HI}$), VMM 39 ($ITK_{HI}$), and A375 ($ITK_{INT}$) were grown as described previously, suspended in matrigel and injected into the flanks of nude mice as described in the Materials and Methods section. The mice received either BI 10N at a concentration of 15 mpk or no treatment. Mice were then followed to assess the effect of the treatments on tumor progression. FIG. 6D-6F) Effect of BI 10N (15mpk) on tumor growth (mean and standard error of mean) in A375, RPMI 8322, and VMM 39 melanoma xenografts. Shown with asterisks are significant results for tumor growth inhibition of BI 10N-treated compared to untreated mice ($P<0.05$, Mann Whitney T test) AZD6244, an active agent against melanoma, is shown for comparison. Samples sizes are indicated in parentheses.

Figure 7A:
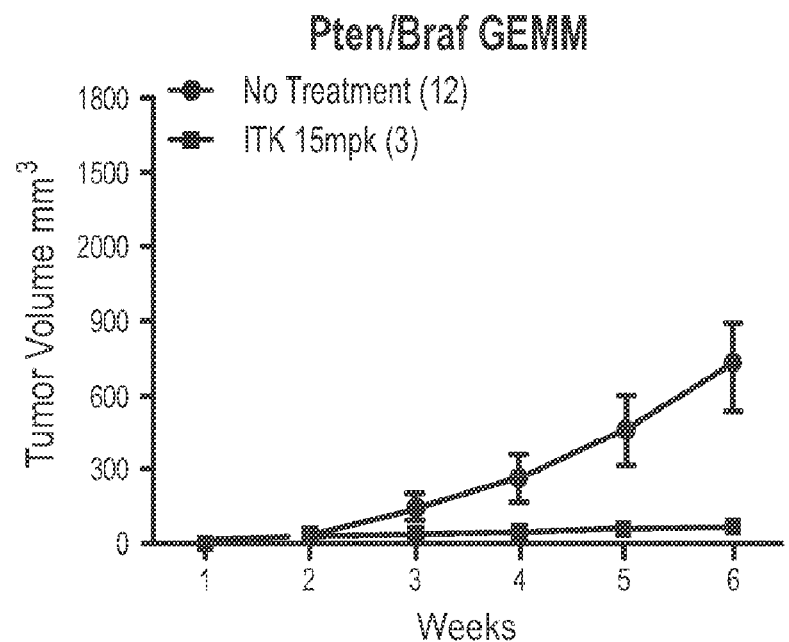
Figure 7B:
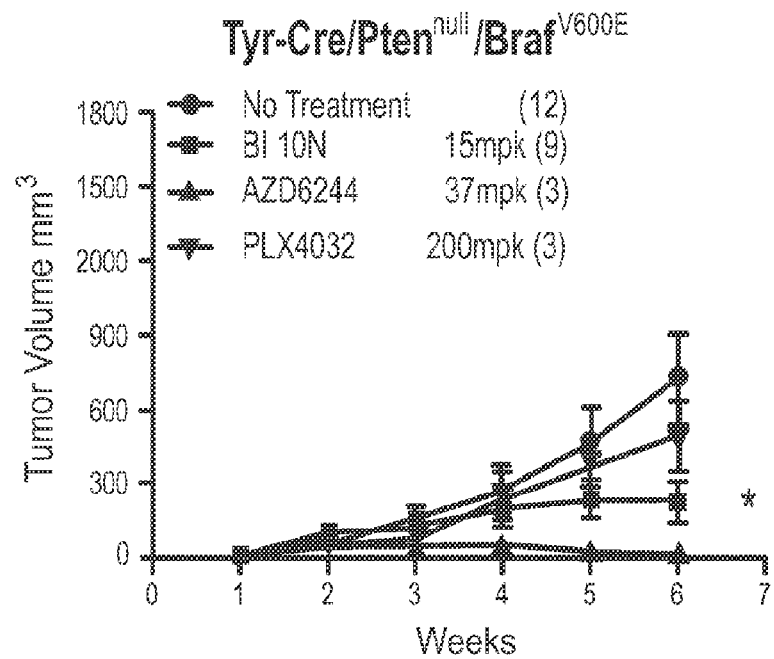

FIG. 7A-7B Effects of BI 10N inhibitor on growth of primary melanoma in the PTEN/BRAF GEMM. A primary melanoma tumor from the PTEN/BRAF mouse GEMM untreated with inhibitors stained with acid fast red for ITK using ITK antibody (Abeam cat#ab32113) (data not shown). A PTEN/BRAF mouse model was used for these in vivo studies. The mice were painted with 4HT (4-hydroxy-tamoxifen) at the base of their tails and within about 4 weeks, 4 mm×4 mm melanomas were typically present in each mouse. The animals were then divided into treatment or no treatment groups. FIG. 7A) Animals were treated as described in panel B, then placed on BI 10N BI 10N at 15 MPK or not treated. Mice were followed for 7 weeks and their tumors were measured once a week to assess tumor volume as described in the Materials and Methods. FIG. 7B) Effect of BI 10N on tumor growth (mean and standard error of mean) in the PTEN/BRAF GEMM. Shown with asterisk is the significant result for tumor growth inhibition of BI 10N-treated compared to untreated mice ($P<0.05$). The effects of AZD6244 and PLX4032 on tumor growth are also shown. Samples sizes are indicated in parentheses.

Figure 8A:
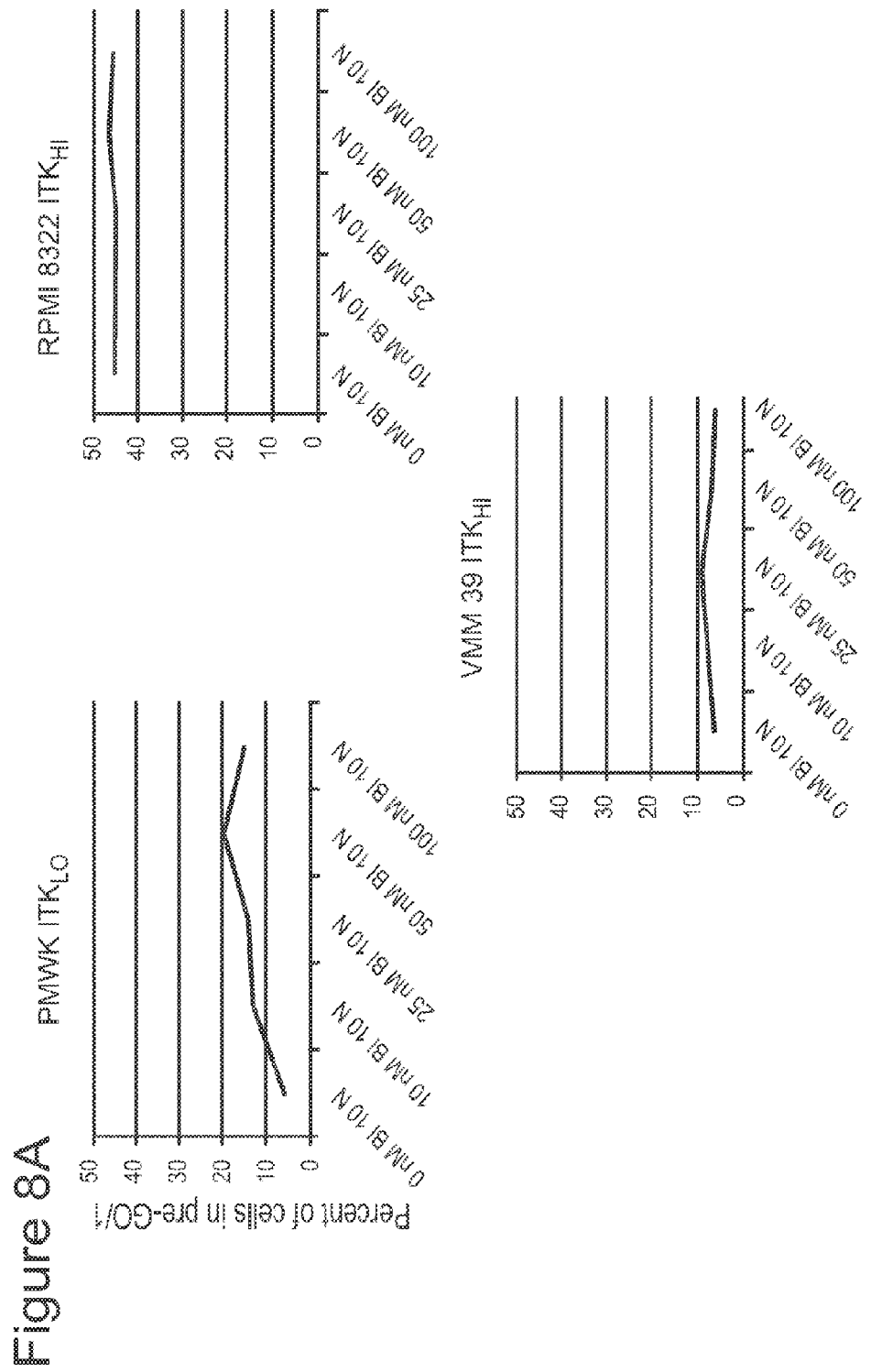

FIG. 8A-8B. Effects of BI 10N on melanoma cell death rates. FIG. 8A) A) Cells within the pre-G0/G1 fraction. Cells were assessed for 5-ethynyl-2'-deoxyuridine (EdU) incorporation rate and DNA content with FxCycle Violet and counted using a Cyan flow cytometer. The percentage of particle in the pre G0/G1 fraction was determined by subtracting the number of cells in the G0/G1, S and G2/M phases from the total number of cells and is plotted at the given BI 10N concentrations. FIG. 8B) Caspase activity in the treated melanoma cells. Caspase activity, a measure of apoptosis, was assayed in PMWK ($ITK_{LO}$), RPMI 8322 ($ITK_{HI}$), and VMM 39 ($ITK_{HI}$) cell lines that had shRNAs against ITK introduced. Staurosporine (staur) is the positive control for apoptosis.

Figure 9:
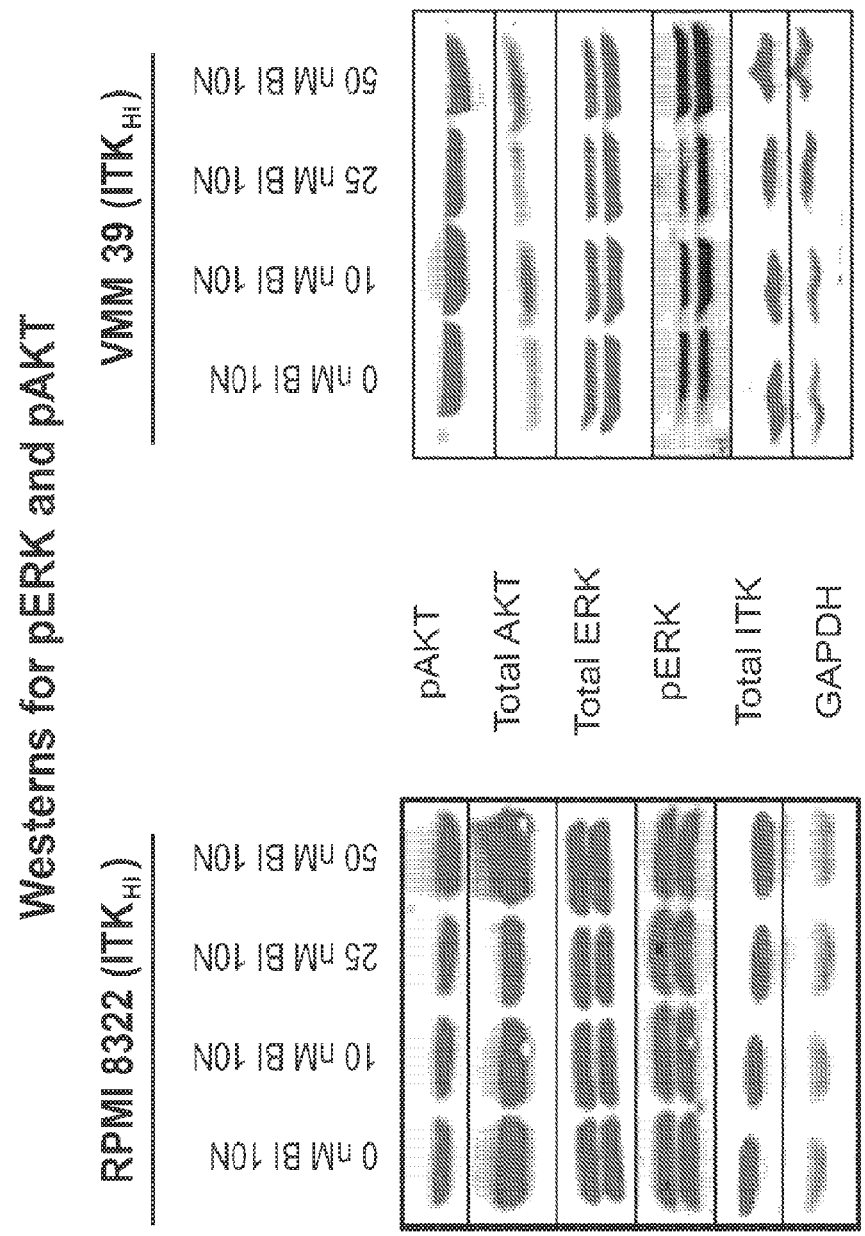

FIG. 9. Western blots of phospho-ERK and phospho-AKT. FIG. 9 shows western blots of phospho-ERK and phospho-AKT in IKT two ITK high cell lines RPMI 8322 ($ITK_{HI}$), and VMM 39 ($ITK_{HI}$) in the presence of increasing concentration of ITK inhibitor BI 10N.

Figure 10A:
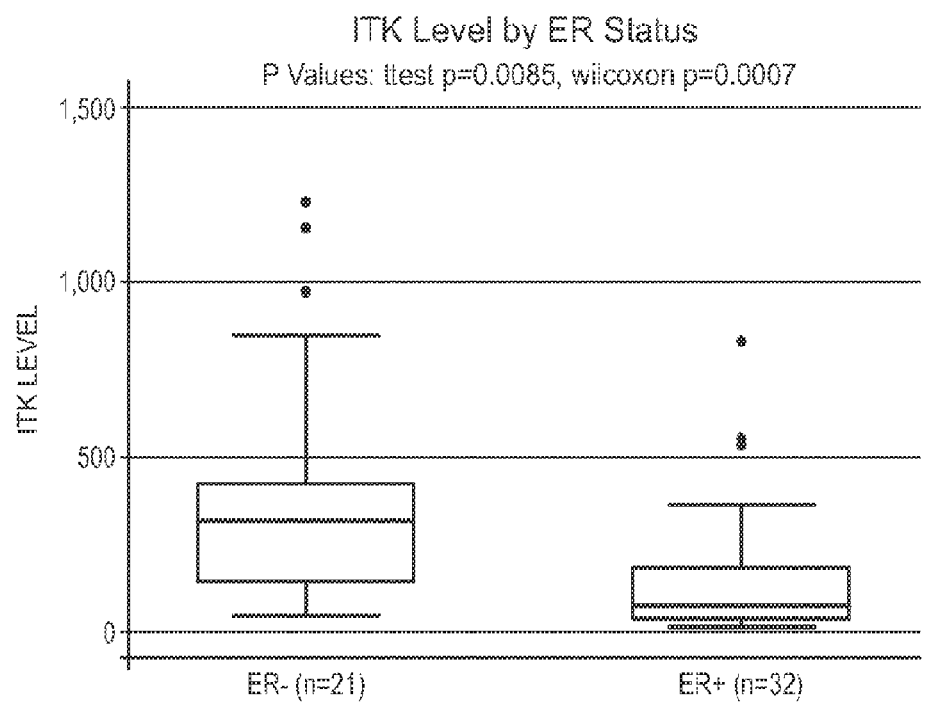
Figure 10B:
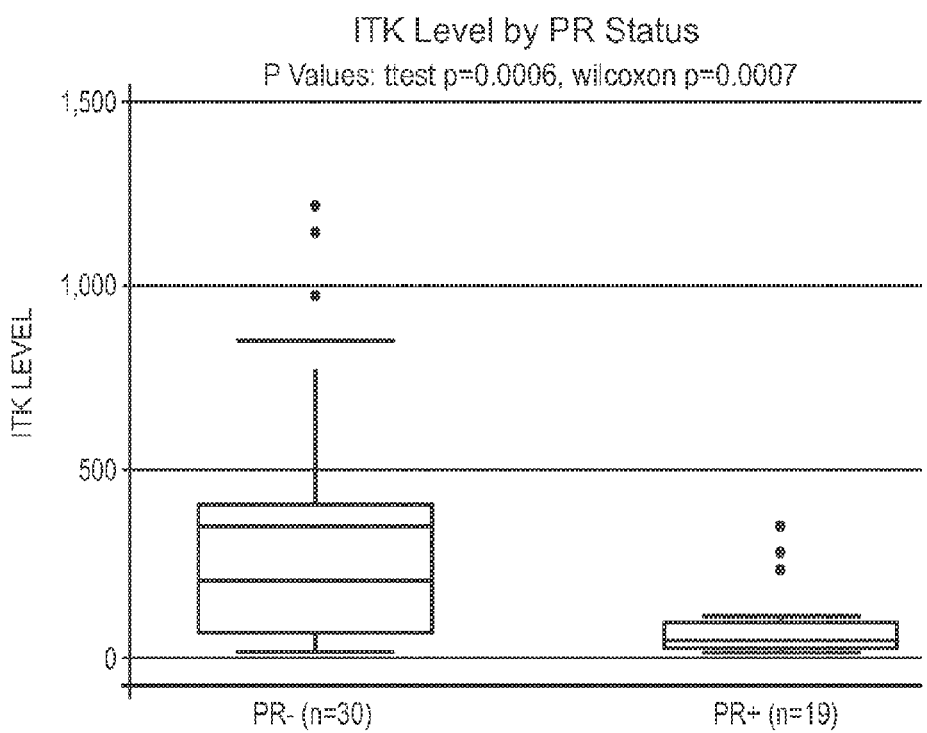
Figure 10C:
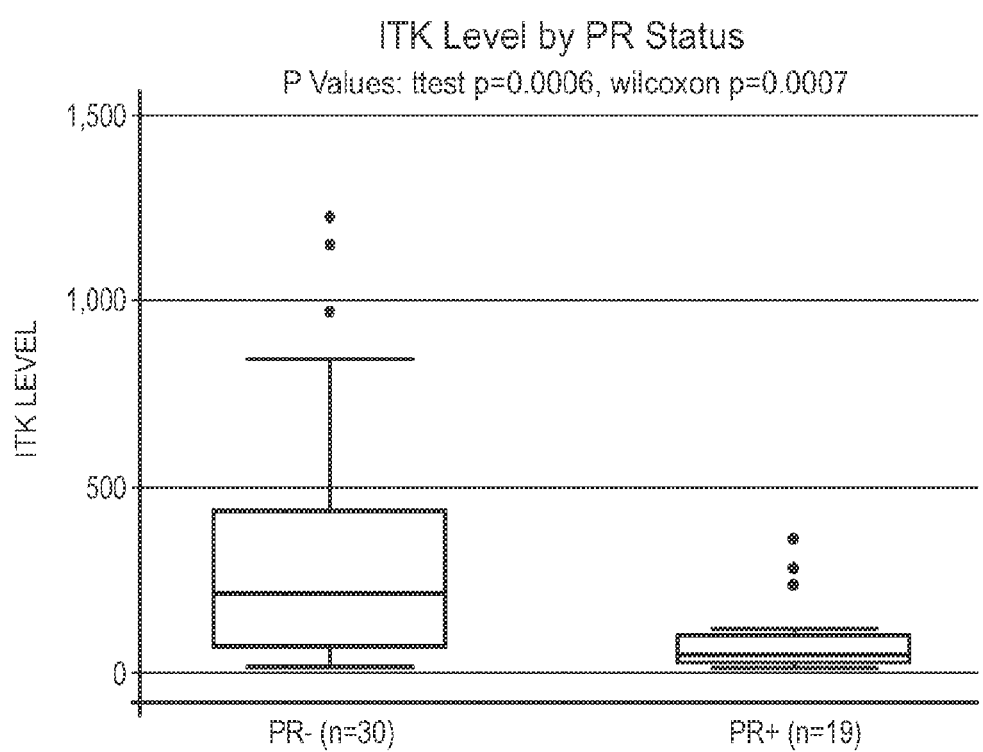

FIG. 10A-10C. The relationship between ITK levels and ER status, PR status or both ER and PR status. FIG. 10A-10C shows the relationship between ER status, PR status and ITK levels for breast cancer samples. See also Table 10 and Section 6.2.15.

5. DETAILED DESCRIPTION OF THE INVENTION

This invention related the use of interleukin-2 inducible T-cell kinase (ITK) inhibitors for the treatment of patients who have melanoma or other solid tumors. This invention provides information regarding the presence of ITK in primary melanoma, melanoma metastases, and in a variety of other solid tumors. This invention also provides demonstration that ITK lentiviral small hairpin RNA knockdowns and a small molecule inhibitor can each decrease the proliferation and migration of melanoma cell lines and a small molecule inhibitor can be used to inhibit the growth of melanomas in mouse models.

Applicants have shown that ITK is expressed at high levels in patient metastatic melanoma tumors and that a small molecule inhibitor decreases the proliferation and migration of melanoma cells in culture and also slows the growth of melanomas in two mouse models. The use of an ITK inhibitor for solid tumors is a surprising result because a key strategy of cancer treatment is to boost a subject's immune response to fight cancer. Expression of ITK is highly restricted and is only normally found in T cells, natural killer (NK) cells, macrophages, and mast cells (Berg et al., 2005 *Annu Rev Immunol* 23:549-600). While there has been interest in ITK inhibitors for hematologic cancers such as T-cell related cancers, for solid tumors a clinician would be reluctant to use an ITK inhibitor because it might interfere with a subject's natural cancer fighting immune response. Surprisingly, Applicants have shown that ITK inhibitors can lead to the regression of solid tumors in vivo.

In the case of melanoma, ITK inhibitors would not only directly inhibit the melanoma cells themselves but also could inhibit dysfunctional $TH_2$ immune cells that inhibit other immune cells from effectively killing the tumors (Igney and Krammer, 2002, *J Leukoc Biol* 7(16): 907-920). Pharmaceuticals targeting ITK are likely to be useful for a variety of solid tumors. Through the use of immunochemistry, applicants have identified high levels of ITK in a substantial percentage of breast, colorectal, uterine carcinoma (including endometrial), gastric, head and neck, and non-small cell lung carcinoma (NSCLC) tumors. There has been extensive pharmacological interest in ITK as a target for the treatment of immunological diseases such as asthma (Lo, 2012 *Expert Opin Ther Pat* 20(4): 459-69). As a result of these efforts, there are several selective small molecule inhibitors available for preclinical studies or to initiate new pharmaceutical programs.

5.1. Definitions

As used herein the term "selective interleukin-2 inducible T-cell kinase (ITK) inhibitor" means a compound with an $IC_{50}$ of at least 2-fold greater for ITK than representative members of the kinase enzyme family. More preferably, the selective inhibitor has an $IC_{50}$ of 5-fold, 10-fold, 20-fold, 100-fold, 500-fold greater than other representative members of the kinase enzyme family. The compound may be an ATP competitive ITK inhibitor. The compounds may be a covalent or irreversible ITK inhibitor. BI 10N is an example of a selective interleukin-2 inducible T-cell kinase (ITK) inhibitor. Examples of selective ITK inhibitors may be found in the scientific and patent literature. Charrier et al. 2013 *Exp Opin Drug Disc* 8(4) 369-381; Charrier et al. 2011 *J Med Chem* 54 2341-2350, e.g. pyridones; Das et al. 2006 *Bioorg Med Chem Lett* 16 2411-2415; Das et al. 2006 *Bioorg Med Chem Lett* 16 3706-3712, e.g., aminothiazoles; Dubovsky et al., 2013 *Blood* 122 2539-2549 (available online Jul. 25, 2013), ibrutinib as an irreversible ITK inhibitor; Guo et al. 2012 *Mol Pharm* 82(5):938-47 e.g., tricyclic imidazo quinoxalins such as CTA056; Harling et al., 2013 *J Biol Chem* 288:28195-28206, e.g., acrylamide-based irreversible ITK inhibitors; Herdemann et al. 2011 *Bioorg Med Chem Lett* 21 1852-1856; Kaur et al. 2012 *Eur J Pharm Sci* 47 574-588; Lin et al. 2004 *Biochem* 43 11056-11062; Lo 2010; Maxwell et al. 2011 *Am Chem Soc* MEDI-8 (e.g., aminobenzothiazoles); Meganathan et al. 2012 *J Mol Model* 2012 Sep. 27. [Epub ahead of print]; Sahu and August 2009 *Curr Top Med Chem* 690-703; Riether et al. 2009; Vargas et al. 2013 *Scand J Immunol* 78 130-139; Velankar et al. 2010 *Bioorg Med Chem* 18 4547-4559; Zapf et al. 2012 *J Med Chem* 2012 Nov. 12. [Epub ahead of print]e.g., pyrazolopyrimidine-based covalent inhibitors; PCT Int'l. Pub Nos WO 2002/050071 (Barrish et al.), WO 2007/058832 (Bentzien et al.), WO 2007/076228 (Bentzien et al.), WO 2011/110575 (e.g., aminobenzothiazoles, Alder et al.), U.S. Pat. Publ. No 2007/0293499 (e.g., aryl ketones, Flynn et al.) the contents of which are hereby incorporated by reference in their entireties.

"Alkenyl" refers to an unsaturated branched, straight-chain or cyclic alkyl group having at least one carbon-carbon double bond derived by the removal of one hydrogen atom from a single carbon atom of a parent alkene. The group may be in either the Z- and E-forms (or cis or trans conformation) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. The alkenyl group may be substituted or unsubstituted. In certain embodiments, an alkenyl group has from 2 to 20 carbon atoms and in other embodiments, from 2 to 8 carbon atoms.

"Alkoxy" refers to a radical —OR where R represents an alkyl, alkyl, cycloalkyl, aryl, or heteroaryl group as defined herein. Representative examples include, but are not limited to, methoxy, ethoxy, propoxy, butoxy, cyclohexyloxy, and the like.

"Alkyl" refers to a saturated, branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. The alkyl group may be substituted or unsubstituted. In certain embodiments, an alkyl group comprises from 1 to 20 carbon atoms. Alternatively, an alkyl group comprising from 1 to 8 carbon atoms.

"Alkyl(aryl)" refers to an acyclic alkyl group in which one of the hydrogen atoms bonded to a carbon atom, typically a terminal or $sp^3$ carbon atom, is replaced with an aryl group. Typical alkyl(aryl) groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. In certain embodiments, an alkyl(aryl) group can be $(C_{6-20})$ alkyl(aryl) e.g., the alkyl group may be $(C_{1-10})$ and the aryl moiety can be $(C_{5-10})$.

"Alkynyl" refers to an unsaturated branched or straight-chain having at least one carbon-carbon triple bond derived by the removal of one hydrogen atom from a single carbon atom of a parent alkyne. Typical alkynyl groups include, but are not limited to, ethynyl, propynyl, butenyl, 2-pentynyl, 3-pentynyl, 2-hexynyl, 3-hexynyl and the like. The alkynyl group may be substituted or unsubstituted. In certain embodiments, an alkynyl group has from 3 to 20 carbon atoms and in other embodiments, from 3 to 8 carbon atoms.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene or cyclopentadiene; or bicyclic ring systems wherein at least one ring is carbocyclic and aromatic, for example, naphthalene, indane. The aryl group may be substituted or unsubstituted.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. The cycloalkyl group may be substituted or unsubstituted. In certain embodiments, the cycloalkyl group can be $C_{3-10}$ to cycloalkyl, such as, for example, $C_{3-6}$ cycloalkyl.

An "effective amount" refers generally to an amount that is a sufficient, but non-toxic, amount of the active ingredient (i.e., an ITK inhibitor) to achieve the desired effect, which is a reduction or elimination in the severity and/or frequency of symptoms and/or improvement or remediation of damage.

"Halogen" refers to a fluoro, chloro, bromo, or iodo group.

"Heteroaryl" refers to a monovalent heteroaromatic group derived by the removal of one hydrogen atom from a single atom of a parent heteroaromatic ring system. Heteroaryl encompasses: 5- to 7-membered aromatic, monocyclic rings containing one or more, for example, from 1 to 4, or in certain embodiments, from 1 to 3, heteroatoms chosen from N, O, and S, with the remaining ring atoms being carbon; and polycyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. The heteroaryl group may be substituted or unsubstituted.

For example, heteroaryl includes a 5- to 7-membered heteroaromatic ring fused to a 5- to 7-membered cycloalkyl ring and a 5- to 7-membered heteroaromatic ring fused to a 5- to 7-membered heterocycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Heterocycloalkyl" refers to a saturated or unsaturated cyclic alkyl group where one or more carbon atoms is replaced with a hetero atom. Where a specific level of saturation is intended, the nomenclature "heterocycloalkanyl" or "heterocycloalkenyl" is used. Typical heterocycloalkyl groups include, but are not limited to, groups derived from cyclopentane, cyclohexane, and the like. The heterocycloalkyl group may be substituted or unsubstituted.

"Pharmaceutically acceptable" refers to generally recognized for use in animals, and more particularly in humans.

"Pharmaceutically acceptable salts" include, but are not limited to, salts of mineral acids, such as hydrochlorides; salts of organic acids; e.g., acetate, benzoate, besylate, bromate, brosylate, camphorsulfonate, fumarate, maleate, mesylate, oxalate, phosphate, succinate, sulfate, tartrate, tosylate, and trifluoroacetate.

A "prophylactically effective amount" refers to an amount that is effective to prevent, hinder or retard the onset of a disease state or symptom.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereoisomers."

"Subjects" include, but are not limited to, humans, mammals, animals such as dogs, cats, farm animals, laboratory animals such as rats, mice, monkeys.

"Substituted" refers to a group in which one or more hydrogen atoms are each independently replaced with the same or different substituent(s). Typical substituents include, but are not limited to, $CO_2H$, halogen, hydroxyl, $-N_3$, $-NH_2$, $-SO_{(1-3)}H$, or $-SH$.

A "therapeutically effective amount" refers to an amount that is sufficient to remedy a disease state or symptoms, or otherwise prevent, hinder, retard or reverse the progression of a disease or any other undesirable symptom.

5.2. Therapeutic Antibodies to ITK

In one non-limiting embodiment the methods described herein may involve the use of therapeutic antibodies specific to ITK. The terms "antibody" and "antibody substance" as used interchangeably herein refer to immunoglobulin molecules and immunologically active portions of immunoglobulin molecules, i.e., molecules that contain an antigen binding site which specifically binds an antigen, such as a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. Alternatively, monomeric binders such as scFv, diabodies, minibodies, small immunoproteins (SIPs) may be prepared. Olafsen et al., 2005 *Cancer Res* 65:5907-5916; Borsi et al., 2002 *Int J Cancer* 102:75-85; Berndorff et al., 2005 *Clin Cancer Res* 11:7053s-7063s; and Tijink et al., 2006 *J Nucl Med* 47:1127-1135. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Antibody producing cells can be obtained from the subject and used to prepare monoclonal antibodies by standard techniques, such as the hybridoma technique originally described by Kohler and Milstein 1975 *Nature* 256:495-497, the human B cell hybridoma technique (see Kozbor et al., 1983, *Immunol. Today* 4:72), the EBV-hybridoma technique (see Cole et al., pp. 77-96 In Monoclonal Antibodies and Cancer Therapy, Alan R. Liss, Inc., 1985) or trioma techniques. The technology for producing hybridomas is well-known (see generally *Current Protocols in Immunology*, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409 (Winter); PCT Publication Nos. WO 92/18619; WO 91/17271; WO 92/20791; WO 92/15679; WO 93/01288; WO 92/01047; WO 92/09690; WO 90/02809; Fuchs et al., 1991 Bio/Technology 9:1370-1372; Hay et al., 1992 *Hum. Antibod Hybridomas* 3:81-85; Huse et al., 1989 *Science* 246:1215-1281; Griffiths et al., 1993 *EMBO J.* 12:725-734.

Additionally, recombinant antibodies, such as chimeric and humanized monoclonal antibodies, comprising both human and non-human portions can be made using standard recombinant DNA techniques. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 5,225,539 (Winter); U.S. Pat. No. 4,816,567 (Cabilly et al.); European Patent Application 125,023; Better et al., 1988 *Science* 240:1041-1043; Liu et al., 1987 *Proc. Natl. Acad Sci. USA* 84:3439-3443; Liu et al., 1987 *J. Immunol.* 139:3521-3526; Sun et al., 1987 *Proc. Natl. Acad. Sci. USA* 84:214-218; Nishimura et al., 1987 *Cancer Res.* 47:999-1005; Wood et al., 1985 *Nature* 314:446-449; and Shaw et al., 1988 *J. Natl. Cancer Inst.* 80:1553-1559; Morrison 1985 *Science* 229: 1202-1207; Oi et al., 1986 Bio/Techniques 4:214; Jones et al., (1986) *Nature* 321:552-525; Verhoeyen et al., 1988 *Science* 239:1534-1536; and Beidler et al., 1988 *J. Immunol.* 141:4053-4060.

Completely human antibodies can be produced using transgenic mice which are incapable of expressing endogenous immunoglobulin heavy and light chain genes, but which can express human heavy and light chain genes. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661, 016; and 5,545,806 (Lonberg et al.). In addition, companies such as Abgenix, Inc. (Freemont, Calif.), can be engaged to provide human antibodies directed against a selected antigen using technology similar to that described above.

Nelson et al., and Nieri et al., recently reviewed therapeutic antibodies either in the market or in clinical development and current techniques for their production. Nelson et al., 2010 *Nat Rev Drug Disc* 9 767-774; Nieri et al., 2009 *Curr Top Med Chem* 16 753-779.

Fully human antibodies also may be produced via CHO cell culture and by transgenic animals and plants. Full-size human monoclonal antibodies are now extracted by milk of transgenic animals (e.g., cows, goats). Redwan 2009 *J Immunoass Immunochem* 30 262-290. Also plants, like tobacco, are used for making antibodies. Tobacco is relatively easy to transfect using the tobacco virus. Yusibov et al., 2011 *Hum Vacc* 7(3) 313-321.

An antibody can be used to detect the ITK over-expression (e.g., in a cellular lysate or cell supernatant) in order to evaluate the level and pattern of expression of the marker. The antibodies can also be used diagnostically to monitor protein levels in tissues or body fluids (e.g., in a tumor cell-containing body fluid) as part of a clinical testing procedure, e.g., to for example, determine the efficacy of a given treatment regimen. Detection can be facilitated by coupling the antibody to a detectable substance. Examples of detectable substances include, but are not limited to, various enzymes, prosthetic groups, fluorescent materials, luminescent materials, bioluminescent materials, and radioactive materials. Examples of suitable enzymes include, but are not limited to, horseradish peroxidase, alkaline phosphatase, β-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not limited to, luciferase, luciferin, and aequorin, and examples of suitable radioactive materials for diagnostics or therapeutics include, but are not limited to, $^{3}$H, $^{125}$I, $^{131}$I, $^{111}$In, $^{177}$Lu, $^{90}$Y, or $^{35}$S.

Therapeutic antibody conjugates are well-known in the art and are the basis for a number of approved drugs such as Gemtuzumab ozogamicin (Mylotarg; Wyeth) with calicheamicin toxin; Brentuximab vedotin (Adcetris; Seattle Genetics) with an auristatin toxin; $^{90}$Y-labelled ibritumomab tiuxetan (Zevalin; IDEC Pharmaceuticals); and $^{131}$I-labelled tositumomab (Bexxar; GlaxoSmithKline), see Scott et al., 2012 *Nat Rev Canc* 12 278-287. Radioactive conjugates may be high energy β-emitters such as $^{90}$Y, medium energy β-emitters such $^{131}$I or $^{177}$Lu, Auger electron emitters such as $^{125}$I, or $^{111}$In, or α-emitters such as $^{225}$Ac, $^{211}$At, $^{213}$Bi, or $^{227}$Th. Steiner and Neri 2011 *Clin Canc Res* 17(20) 6406-6416. In addition to the antibody drug conjugates (ADCs) mentioned above, various toxins that target microtubules, DNA or DNA enzymes such as topoisomerase II are in development. Examples of other conjugates in clinical development are dolastatin, doxorubicin, maytansine, or paclitaxel. The linker technology for ADCs is well understood. See for example Iyer and Kadambi 2011 *J Pharmacol Tox Meth* 64 207-211.

5.3. Methods of Inhibition Using Nucleic Acids

A variety of nucleic acids, such as antisense nucleic acids, shRNAs, siRNAs or ribozymes, may be used to inhibit the function of the markers of this invention. Ribozymes that cleave mRNA at site-specific recognition sequences can be used to destroy target mRNAs, particularly through the use of hammerhead ribozymes. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art. A composition of ribozyme molecules preferably includes one or more sequences complementary to a target mRNA, and the well-known catalytic sequence responsible for mRNA cleavage or a functionally equivalent sequence (see, e.g., U.S. Pat. No. 5,093,246 (Cech et al.); U.S. Pat. No. 5,766,942 (Haseloff et al.); U.S. Pat. No. 5,856,188 (Hampel et al.) which are incorporated herein by reference in their entirety). Ribozyme molecules designed to catalytically cleave target RNA transcripts can also be used to treat or prevent ITK expressing tumors.

5.4. Combination Therapies

The invention provides combination therapies for various solid tumors. The methods of inhibiting solid tumor growth using ITK inhibitors may be used in combination with various chemotherapeutic agents. Non-limiting examples chemotherapeutic agents known in the art are 5-fluorouracil; asparaginase; bevacizumab (Avastin®); bleomycin; campathecins; carboplatin; cetuximab (Erbitux®); cisplatin; crizotinib (Xalkori®); cyclophosphamide; cytarabine; dacarbazine; dactinomycin; dasatinib (Sprycel®); daunorubicin; DNA methyltransferase inhibitors (DNMTs) such as azacitidine (Vidaza®) and decitabine; doxorubicin; doxorubicin; epirubicin; erbstatin; erlotinib (Tarceva®); estramustine; etoposide; etoposide; gefitinib (Iressa®), gemcitabine, genistein, histone acetyl transferase inhibitors (HATs); histone deacetyl transferase inhibitors (HDACs) such as belinostat, entinostat (MS-275), panobinostat, PCI-24781, romidepsin (depsipeptide, FK-228), valproic acid, vorinostat (Zolinza®, SAHA) or heat shock protein inhibitors, including HSP90 inhibitors such as alvespimycin (IPI-493), AT13387, AUY922 (resorcinolic isoxazole amide), CNF2024 (BIIB021), HSP990, MPC-3100, retaspimycin (IPI-504), SNX-2112, SNX-5422, STA-9090, tanespimycin (17-AAG; KOS-953), or XL888; herbimycin A; hexamethylmelamine; hedgehog pathway inhibitors such as saridegib (IPL-926), vismodegib (ERIVEDGE™); hydroxyurea, idarubicin, ifosfamide, imatinib (Gleevec®), irinotecan, lapatinib (Tykerb®), lavendustin A, leucovorin, levamisole, mercaptopurine, methotrexate, mitomycin, mitoxantrone, mTOR inhibitors such as everolimus (Afinitor®), sirolimus (Rapamune®), temsirolimus (Torisel®); nilotinib (Tasigna®); nitrosoureas such as carmustine and lomustine; paclitaxel; panitumumab (Vectibix®); pazopanib (Votrient®); pegaptanib (Macugen®); platinum compounds; plicamycin; procarbizine; proteasome inhibitors such as bortezomib (Velcade®); ranibizumab (Lucentis®); sorafenib (Nexavar®); sunitinib (Sutent®); Tamoxifen; taxanes such as docetaxel, paclitaxel, taxol; thioguanine; topotecan; trastuzumab (Herceptin®); tyrosine kinase inhibitors; tyrphostins; vandetanib (Caprelsa®); vemurafenib (Zelboraf®); vinblastine; vinca alkaloids; vincristine; or vinorelbine.

In a preferred embodiment, the chemotherapeutic agent used in combination is bevacizumab (Avastin®), cetuximab (Erbitux®), crizotinib (Xalkori®), dasatinib (Sprycel®), erlotinib (Tarceva®), everolimus (Afinitor®), gefitinib (Iressa®), imatinib (Gleevec®), lapatinib (Tykerb®), nilotinib (Tasigna®), panitumumab (Vectibix®), pazopanib (Votrient®), sirolimus (Rapamune®), sorafenib (Nexavar®), sunitinib (Sutent®), Tamoxifen, temsirolimus (Torisel®), trastuzumab (Herceptin®), vandetanib (Caprelsa®), or vemurafenib (Zelboraf®). Further examples of chemotherapeutic agents may be found in standard publications and texts. See e.g., National Comprehensive Cancer Network (NCCN Guideline™) or Manual of Clinical Oncology, Dennis A. Casciato and Barry B. Lowitz, ed., 4th edition, Jul. 15, 2000, Little, Brown and Company, U.S.

5.5. Pharmaceutically Acceptable Compositions

Provided herein are pharmaceutical compositions comprising an ITK inhibitor as an active ingredient, or a pharmaceutically acceptable salt, solvate or hydrate thereof in combination with a pharmaceutically acceptable vehicle, carrier, diluent, or excipient, or a mixture thereof.

The compound provided herein may be administered alone, or in combination with one or more other compounds provided herein. The pharmaceutical compositions that comprise an ITK inhibitor can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy,* 21st Ed., Lippincott, Williams & Wilkins, Baltimore, M. D., 2006; Modified-Release Drug Delivery Technology, Rathbone et al., Eds., *Drugs and the Pharmaceutical Science*, Marcel Dekker, Inc.: New York, N. Y., 2003; Vol. 126).

In one embodiment, the pharmaceutical compositions are provided in a dosage form for oral administration, which comprise a compound provided herein, e.g., an ITK inhibitor or a pharmaceutically acceptable salt, solvate or hydrate thereof; and one or more pharmaceutically acceptable excipients or carriers.

In another embodiment, the pharmaceutical compositions are provided in a dosage form for parenteral administration, which comprise an ITK inhibitor or a pharmaceutically acceptable salt, solvate or hydrate thereof; and one or more pharmaceutically acceptable excipients or carriers.

In yet another embodiment, the pharmaceutical compositions are provided in a dosage form for topical administration, which comprise an ITK inhibitor or a pharmaceutically acceptable salt, solvate or hydrate thereof; and one or more pharmaceutically acceptable excipients or carriers.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons. The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In one embodiment, the therapeutically effective dose is from about 0.1 mg to about 2,000 mg per day of a compound provided herein. The pharmaceutical compositions therefore should provide a dosage of from about 0.1 mg to about 2000 mg of the compound. In certain embodiments, pharmaceutical dosage unit forms are prepared to provide from about 1 mg to about 2000 mg, from about 10 mg to about 1000 mg, from about 20 mg to about 500 mg or from about 25 mg to about 250 mg of the essential active ingredient or a combination of essential ingredients per dosage unit form. In certain embodiments, the pharmaceutical dosage unit forms are prepared to provide about 10 mg, 20 mg, 25 mg, 50 mg, 100 mg, 250 mg, 500 mg, 1000 mg or 2000 mg of the essential active ingredient.

5.5.1. Parental Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein can be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In one embodiment, the lyophilized nanoparticles are provided in a vial for reconstitution with a sterile aqueous solution just prior to injection. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions. The pharmaceutical compositions provided herein can be formulated as immediate or modified release dosage forms, including delayed-, sustained-, pulsed-, controlled, targeted-, and programmed-release forms.

The pharmaceutical compositions can be formulated as a suspension, solid, semisolid, or thixotropic liquid, for administration as an implanted depot.

5.5.2. Oral Administration Compositions

The pharmaceutical compositions provided herein can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, troches, lozenges, pastilles, cachets, pellets, medicated chewing gum, bulk powders, effervescent or non-effervescent powders or granules, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar, bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W. R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Hydrophilic polymer formulations have been widely used for improved oral availability such as ethylene oxides, hydroxy propyl methyl cellulose (HPC), poly(ethylene oxide) (PEO), polyvinyl alcohol (PVA), poly(hydroxyethylmethyl acrylate) methyl methacrylate (PHEMA), or vinyl acetate (PCT Pub. No. WO1999/37302 (Alvarez et al.); Dimitrov & Lambov, 1999, Int J Pharm 189 105-111; Zhang et al., 1990, *Proc Int. Symp Controlled Release Bioact. Mater.* 17, 333, the contents of which are hereby incorporated by reference in their entirety). Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545, the contents of which are hereby incorporated by reference in their entirety. The capsules may also be coated as known by those of skill in the art in order to modify or sustain dissolution of the active ingredient.

The pharmaceutical compositions provided herein can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458, the content of which is hereby incorporated by reference in its entirety.

The pharmaceutical compositions provided herein can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms. The pharmaceutical compositions provided herein can be formulated as immediate or modified release dosage forms, including delayed-, sustained, pulsed-, controlled, targeted-, and programmed-release forms.

The pharmaceutical compositions provided herein can be co-formulated with other active ingredients which do not impair the desired therapeutic action, or with substances that supplement the desired action.

5.5.3. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein can also comprise liposomes, micelles, microspheres, nanosystems, and mixtures thereof Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJEC™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration can further comprise a suitable flavor, such as menthol and levomenthol, or sweeteners, such as saccharin or saccharin sodium.

The pharmaceutical compositions provided herein for topical administration can be formulated to be immediate release or modified release, including delayed-, sustained-, pulsed-, controlled-, targeted, and programmed release.

5.6. Modified Release Formulations

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500, the contents of which are hereby incorporated by reference in their entirety.

5.6.1. Matrix Controlled Release Devices

The pharmaceutical compositions provided herein in a modified release dosage form can be fabricated using a matrix controlled release device known to those skilled in the art (see, Takada et al. in "*Encyclopedia of Controlled Drug Delivery*," Vol. 2, Mathiowitz Ed., Wiley, 1999).

In one embodiment, the pharmaceutical compositions provided herein in a modified release dosage form is formulated using an erodible matrix device, which is waterswellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethylene terephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed; the polymer viscosity; the particle sizes of the polymer and/or the active ingredient(s); the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, melt-granulation followed by compression.

5.6.2. Osmotic Controlled Release Devices

The pharmaceutical compositions provided herein in a modified release dosage form can be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol, organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220, the contents of which are hereby incorporated by reference in their entirety.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art. See, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27, the contents of which are hereby incorporated by reference in their entirety.

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918, the contents of which are hereby incorporated by reference in their entirety. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxyethyl cellulose, and other pharmaceutically acceptable excipients or carriers.

5.6.3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

5.7. Dosage

The pharmaceutical compositions that are provided can be administered for prophylactic and/or therapeutic treatments. In general, toxicity and therapeutic efficacy of the ITK inhibitor can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred.

The data obtained from cell culture and/or animal studies can be used in formulating a range of dosages for humans. The dosage of the active ingredient typically lines within a range of circulating concentrations that include the ED50 with little or no toxicity. The dosage can vary within this range depending upon the dosage form employed and the route of administration utilized.

The effective amount of a pharmaceutical composition comprising an ITK inhibitor to be employed therapeutically or prophylactically will depend, for example, upon the therapeutic context and objectives. One skilled in the art will appreciate that the appropriate dosage levels for treatment, according to certain embodiments, will thus vary depending, in part, upon the molecule delivered, the indication for which the ITK inhibitor is being used, the route of administration, and the size (body weight, body surface or organ size) and/or condition (the age and general health) of the patient. A clinician may titer the dosage and modify the route of administration to obtain the optimal therapeutic effect. Typical dosages range from about 0.1 μg/kg to up to about 100 mg/kg or more, depending on the factors mentioned above. In certain embodiments, the dosage may range from 0.1 µg/kg up to about 150 mg/kg; or 1 µg/kg up to about 100 mg/kg; or 5 µg/kg up to about 50 mg/kg.

The dosing frequency will depend upon the pharmacokinetic parameters of the ITK inhibitor in the formulation. For example, a clinician will administer the composition until a dosage is reached that achieves the desired effect. The composition may therefore be administered as a single dose or as two or more doses (which may or may not contain the same amount of the desired molecule) over time, or as a continuous infusion via an implantation device or catheter. Treatment may be continuous over time or intermittent. Further refinement of the appropriate dosage is routinely made by those of ordinary skill in the art and is within the ambit of tasks routinely performed by them. Appropriate dosages may be ascertained through use of appropriate dose-response data.

5.8. In Vivo Imaging

The invention also provide reagents for in vivo imaging such as, for instance, the imaging of ITK over-expression in a tumor using labeled reagents that detect (i) nucleic acids encoding ITK, (ii) ITK polypeptides, or (iii) the full-length ITK protein. In vivo imaging techniques may be used, for example, as guides for surgical resection or to detect the distant spread of melanoma metastasis. For in vivo imaging purposes, reagents that detect the presence of these proteins or genes, such as antibodies, may be labeled with a positron-emitting isotope (e.g., 18F) for positron emission tomography (PET), gamma-ray isotope (e.g., 99mTc) for single photon emission computed tomography (SPECT), a paramagnetic molecule or nanoparticle (e.g., $Gd^{3+}$ chelate or coated magnetite nanoparticle) for magnetic resonance imaging (MRI), a near-infrared fluorophore for near-infrared (near-IR) imaging, a luciferase (firefly, bacterial, or coelenterate), green fluorescent protein, or other luminescent molecule for bioluminescence imaging, or a perfluorocarbon-filled vesicle for ultrasound.

Furthermore, such reagents may include a fluorescent moiety, such as a fluorescent protein, peptide, or fluorescent dye molecule. Common classes of fluorescent dyes include, but are not limited to, xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Fluorescent dyes are discussed, for example, in U.S. Pat. No. 4,452,720 (Harada et al.); U.S. Pat. No. 5,227,487 (Haugland and Whitaker); and U.S. Pat. No. 5,543,295 (Bronstein et al.). Other fluorescent labels suitable for use in the practice of this invention include a fluorescein dye. Typical fluorescein dyes include, but are not limited to, 5-carboxyfluorescein, fluorescein-5-isothiocyanate, and 6-carboxyfluorescein; examples of other fluorescein dyes can be found, for example, in U.S. Pat. No. 4,439,356 (Khanna and Colvin); U.S. Pat. No. 5,066,580 (Lee), U.S. Pat. No. 5,750,409 (Hermann et al.); and U.S. Pat. No. 6,008,379 (Benson et al.). The kits may include a rhodamine dye, such as, for example, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the trade name of TEXAS RED®, and other rhodamine dyes. Other rhodamine dyes can be found, for example, in U.S. Pat. No. 5,936,087 (Benson et al.), U.S. Pat. No. 6,025,505 (Lee et al.); U.S. Pat. No. 6,080,852 (Lee et al.). The kits may include a cyanine dye, such as, for example, Cy3, Cy3B, Cy3.5, Cy5, Cy5.5, and Cy7. Phosphorescent compounds including porphyrins, phthalocyanines, polyaromatic compounds such as pyrenes, anthracenes and acenaphthenes, and so forth, may also be used.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present invention may suitably "comprise", "consist of", or "consist essentially of", the steps, elements, and/or reagents described in the claims.

The following Examples further illustrate the invention and are not intended to limit the scope of the invention.

6. EXAMPLES 6.1. Materials and Methods 6.1.1. Production and Use of shRNA Lentivirus Lentiviral small hairpin RNA (shRNA) constructs were procured from the University of North Carolina at Chapel Hill's Lenti shRNA core facility. This facility supplied shRNA constructs TRCN0000010020 (ITK4), TRCN0000010021 (ITK5), TRCN0000010022 (ITK6), and TRCN0000010023 (ITK7) from the Thermo Scientific TRC shRNA library TRC-Hs1.0 (Human). Lentivirus was produced using the Invitrogen ViraPower™ Lentiviral Packaging Mix (cat#44-2050). Briefly, $5 \times 10^6$ 293 FT cells were plated in a 75 $cm^2$ tissue culture flask the day before transfection. On the day of transfection, the culture media was removed and replaced with 5 ml of growth media without serum. The cells were transfected with 9 jigs of Virapower and 3 µgs of the shRNA plasmid from the TRC-Hs1.0 library using Lipofectamine 3000. The next day the media was removed and replaced with 7 mls of media plus serum. Two days later the media was harvested, centrifuged at 1000 RPM for 5 minutes to remove debris and the supernatant was placed in cryotubes and stored at −80° C. In order to produce cell lines that harbored the shRNA lentivirus the cells were plated at 25% confluency the day before transduction in complete media. The next day the media was removed and replaced with fresh complete media with polybrene added to 4 ug/ml concentration. The lentiviral stock was thawed at room temperature and 100 uls was added to the cells. The next day the media was removed and fresh complete media was added. The next day the media was removed and replaced with fresh complete media with puromycin at a final concentration of 10 µg/ml. The cells were allowed to grow for 4 more days and then they were used as described in the experiment.

For a negative control, we transduced the exact same melanoma cell lines with a scrambled shRNA (SCR). As shown in FIG. 4E, western blot analysis of whole cell lysates obtained from lentiviral transduced and parental melanoma cell lines showed a dramatic decrease (>85%) in the level of ITK protein in the VMM 39 ($ITK_{HI}$) cells which were stably transduced with shRNAs ITK 4, 5, and 7 while the ITK 6 and SCR cell lines did not show any appreciable ITK reduction.

6.1.2. Westerns and Cell Lysate Generation

Cells were trypsinized from the plate and washed once with PBS. The PBS was removed and the cells were resuspended in lysis buffer (0.5×PBS and 2% NP-40, lx Roche protease inhibitors (cat#05 892 791 001) and 1× phosphatase inhibitors (04906845001)). The cells were incubated on ice for 10 minutes and the lysate was then spun at 14,000 rpm for 5 minutes to pellet the nuclei. Lysates were then assayed for protein concentration using the DC Protein Assay Kit II from BioRad (cat#500-0112EDU). Westerns were quantitated using the LiCor Biosciences Odyssey infrared imaging system.

6.13. Antibodies

Rabbit monoclonal anti ITK (Y401) (cat #ab32039) was obtained from Abcam (Cambridge, Mass.). Phospho-ser473-AKT (736E 11) and Phospho ERK antibodies were from Cell Signaling Technology (Danvers Mass.). Rabbit polyclonal antibody to S100 was obtained from DakoCytomation, Inc. (Carpinteria, Calif.) and mouse monoclonal S100 (clone S1/61/69) antibody from Leica Microsystems Inc. (Norwell Mass.). Mouse tissues were stained for ITK using ab32113 from Abcam, Inc. Tables 10, 11A and 11B describe the details of the antibodies and protocols.

6.1.4. Cell Line Block Preparation and Construction of Cell Line Arrays (CLA)

Cell pellets were fixed in 10% buffered formalin for 16-24 h, washed twice in 70% ethanol, clotted in 2% low-melting agarose, and processed then embedded in paraffin wax. Individual cell line blocks were sectioned and stained with Hematoxylin and Eosin (H&E) to verify the quality of the prepared cell clots and guide Cell Line Array (CLA) construction. Three 1 mm diameter cores were removed from each cell line block and randomly embedded into a CLA block. The CLA block was cut into 5 micron-thick sections.

6.1.5. Tissue Microarray (TMA) Construction

Metastatic melanoma and other solid tumor cases were obtained from the UNC Hospitals surgical pathology archive under Internal Review Board approval. Hematoxylin and Eosin (H&E) stained sections of tumors on slides were reviewed by a pathologist who circled representative areas of the tumors for coring of the tumor blocks. TMA blocks, containing triplicate cores (0.6 mm) of melanoma metastases were constructed. TMA blocks were cut into 4 micron-thick sections. A pathologist examined H&E slides of the TMAs to confirm the presence of tumor.

6.1.6. Immunohistochemistry for ITK in Human Tissues

Single fluorescent immunohistochemistry (IHC) of the Cell Line Arrays with ITK and sequential dual stains of metastatic melanoma TMA and whole tissue primary melanoma and nevus (mole) section (WTS) slides with ITK (Abcam (Cambridge, Mass.) Cat#ab32039), S100 and other antibodies (see Tables 10, 11A and 11B) were carried out using the Bond fully-automated slide staining system (Leica Microsystems Inc., Norwell Mass.). Slides were deparaffinized in Bond dewax solution (AR9222) and hydrated in Bond wash solution (AR9590). Antigen retrieval for ITK and S100 was performed for 30 min at 100° C. in Bond-epitope retrieval solution 2 pH9.0 (AR9640). After pretreatment, slides were first incubated with ITK antibody (1:3000) followed with Bond polymer (DS9800); the tyramide Cy5 amplification was used to visualize ITK (PerkinElmer, Boston, Mass.). After completion of ITK staining the S100 antibody (1:3200) was applied, which was detected with Alexa555 labeled goat anti rabbit secondary antibody (Invitrogen, Carlsbad, Calif.). The stained slides were mounted with ProLong Gold antifade reagent (Molecular Probes, Inc. Eugene, Oreg. 97402) containing 4',6-diamidino-2-phenylindole (DAPI) to define nuclei.

Deidentified specimens of bladder, brain (astrocytoma/glioblastoma), breast, colorectal, gastric, head and neck, hepatocellular, larynx, neuroendocrine, NSCLC, ovarian, pancreatic, renal, thyroid, and uterine carcinomas on TMA slides were stained with ITK (1:3000) for 1 h as described above and detected with the 3,3'-diaminobenzidine (DAB) chromogen using Bond Polymer Refine Detection System (DS9800). Stained slides were dehydrated and coverslipped. See Tables 3B and 3C.

6.1.7. P-AKT, P-ERK, PD-L1, S100 and Others in Human Tissues

Antigen retrieval for P-AKT, P-ERK, PD-L, S100 and others was carried out for 30 min at 100° C. in Bond-epitope retrieval solution 1 pH6.0 (AR9961) or in solution 2 pH9.0 (AR9640). Metastatic melanoma TMAs were stained with a cocktail comprised of P-AKT (1:10)-S100 (1:25) or P-ERK (1:100)-S100 (1:25) antibodies. S100 was detected with Alexa555 labeled goat anti mouse secondary antibody (Invitrogen, Carlsbad, Calif.) and P-AKT and P-ERK with Bond polymer (DS9800) followed by the tyramide Cy5 (PerkinElmer, Boston, Mass.). The stained slides were mounted with ProLong Gold antifade reagent (Molecular Probes, Inc. Eugene, Oreg. 97402) containing 4',6-diamidino-2-phenylindole (DAPI) to define nuclei. See tables 11A-11C for additional details

6.1.8. Digitization of Slides and Analyses

H&E and IHC stained WTS, CLA and tumor TMA slides were digitally imaged at 20× magnification using the Aperio ScanScope XT (Aperio Technologies, Vista, Calif.). High resolution acquisition (20× objective) of fluorescently stained slides in the DAPI, Cy3 and Cy5 channels was performed in the Aperio-FL (Aperio Technologies, Vista, Calif.). Fluorescently stained CLA slides were scanned in PM2000 (HistoRx). Chromogenically and fluorescently stained images were stored within the Aperio Spectrum Database. TMALab™ (Aperio Technologies, Vista, Calif.) software was used to segment TMA spots, folded tissues and artifacts were excluded from the analysis using Aperio negative pen. WTS tumor areas were circled for analysis using the Aperio positive pen tool. Fluorescently stained WTS and TMA spot images were submitted for analysis through Spectrum using HistoRx AQUA software version 2.2 according to the AQUAnalysis™ user guide (Aperio Edition; Rev. 1.0, CDN0044, HistoRx, New Haven, Conn.). Expression of ITK and P-AKT or P-ERK target proteins labeled by Cy5 (red) were measured in S100-specific tumor mask labeled by Alexa555 (green). ITK expression in CLA spots were measured in the autofluorescent (Cy3) mask. Aperio V9 color deconvolution (area analysis) algorithm was used to quantify expression of ITK in chromogenically stained tumor TMA spots using score (0-300) and percent of positive area outputs.

6.1.9. Cell Culture

Human melanoma cell lines A375, VMM 39, RPMI 8322, SKMEL 103, SKMEL 131, PMWK, and SKMEL 153 were cultured and obtained from sources detailed previously (Carson et al., 2012 *Pigment Cell Melanoma Res* 25(4):514-526). PMWK cells were passaged in Alpha MEM media with 0.5× minimal essential amino acids and 10% FBS, VMM 39, SKMEL 103, SKMEL 147 and A375 were passaged in DMEM with 10% FBS, and RPMI 8322 and SKMEL 131, were grown in RPMI 1640 with 10% FBS. All were grown without antibiotic unless noted in the materials and methods section. Normal human melanocytes were obtained from Clonetech, Inc. (Mountain View, Calif., USA) and were cultured as described previously (Carson et al., 2012; Kaufmann et al., (2008) *J Invest Dermatol* 128, 175-187).

6.1.10. ITK Inhibitor BI 10N

The ITK inhibitor used for these experiments was the BI 10N compound described previously (Riether et al., 2009 *Bioorg Med Chem Lett* 19(6):1588-91). BI 10N is a 5-aminomethylbenzimdazole derivative that has been shown to inhibit ITK with an IC50 of 1 nM, is bioavailable in mice with an F value of 21%, and has been shown to decrease cytokine production in anti-CD3 antibody stimulated Balb/c mice in vivo (Riether et al., 2009). The BI 10N compound was procured from ChangChun Discovery Sciences and 1000× working dilutions were made in DMSO. The dilutions were stored at −20° C. until they were needed.

6.1.11. Proliferation Assay

Human melanoma cell lines were plated onto 10 cm² 6 well dishes at a density of 50,000 cells per well. ITK inhibitor was added to the desired concentration and DMSO (1:1000) was used as a negative control (0 nM). To count the cells, they were trypsinized from the plate on the designated day by aspirating the media, adding 4 mls of PBS, aspirating the PBS, adding 500 μl of 1× Trypsin EDTA for 5 minutes or until the cells were no longer adhered to the plate. Five hundred Ls of media was added to the cell suspension, the cells were removed from the well and then counted using the Countess® Automated Cell Counter from Life Technologies (cat #C10227). Ten L of cell suspension sample was added to ten μL of 0.4% trypan blue staining solution and a Ten L of this was then recounted using the Countess® Automated Cell Counter. Graphs were generated using GraphPad Prism 5.

6.1.12. EdU-FxCycle Violet Staining of Melanoma Cells

Melanoma cells were grown to approximately 60% confluence in T25 tissue culture flasks (Corning Product #430639). On the day of analysis cells were labeled with Click-iT EdU Alexa fluor 488 (C10425, Invitrogen) followed by detection using and FxCycle Violet (F-10347, Invitrogen) for DNA stain, as per manufacturer's recommendations. Cell cycle acquisition was performed on the CyanADP from Beckman Coulter followed by cell cycle analysis using the Summit (version 4.3) software.

6.1.13. Motility Assay

Single cell tracking was performed as described (Williams et al., 2012 *Circ Res* 111(1):56-65). Briefly melanoma cells were plated on 5 μg/cm2 collagen coated MatTek dishes (MatTek Corp., Ashland, Mass. part #P35G-1.5-10-C) and allowed to attach for 24 hours in the presence of either DMSO (1:1000) or BI 10N in DMSO. Cells were monitored for 16 hours using the Olympus VivaView live cell imaging microscope system. Images were taken at a magnification of 10× and were converted to stacks using Image J software. Single-cells were tracked using Image J manual tracking software and velocities were obtained. To avoid bias in the analysis, we tracked only cells that did not divide, remained within the field of view for the entire duration of the experiment, and did not touch other cells more than transiently.

6.1.14. Soft Agar Assay

Soft agar assays were performed employing the RPMI 8322, VMM 39, PMWK, and A375 cell lines. In 24-well cell culture plates (BD Falcon), a 2.0% base agar solution in the appropriate cell line media was poured and allowed to solidify. Tissue culture cells were then trypsinized from their flask, counted using the Countess® Automated Cell Counter, and 2,500 cells per well were added to a 1.4% agarose solution then poured on top of the solidified base agar. Each of the three layers in the culture plate wells contained BI 10N in the indicated concentrations. The cells were incubated at 37° C. for three to four weeks to ensure adequate growth. 3-(4,5-dimethylthiazol-2-yl)-2,5-diphenyltetrazolium bromide (MTT) was then added in order to perform colony counts using Image J photo processing software.

The shRNAs were utilized to study the effects of decreased ITK expression on melanoma cell proliferation, cell cycle profiles, apoptosis, and motility. Melanoma cell lines VMM 39 and RPMI 8322 (both $ITK_{HI}$) that were transduced with shRNAs ITK 4, 5 or 7 proliferated at a rate approximately 50% that of the parental lines with normal ITK expression (FIG. 4C). Small hairpin RNAs 4 and 7 slightly decreased the proliferation of PMWK ($ITK_{LO}$) weakly (P=0.01 and P=0.11, respectively) but no effects on the PMWK proliferation were seen with the shRNAs ITK 5, 6 or SCR. The results of the statistical analyses of the effects of ITK shRNAs on proliferation of melanoma cell lines are shown in Table 7A.

To assess whether the lower proliferation rate of ITK suppressed melanoma cells was secondary to an arrest at any particular phase of the cell cycle, each of the shRNA expressing melanoma cells were subjected to cell cycle analysis by testing their ability to incorporate 5-ethynyl-2'-deoxyuridine (EdU) for measurement of de novo DNA synthesis (S-phase) and FxCycle violet staining for DNA content. Inhibition of ITK expression in the VMM 39 ($ITK_{HI}$) and RPMI 8322 ($ITK_{HI}$) cell lines increased the number of cells in G0/G1 ($FxCycle^{low}$ $EdU^{low}$) and decreased the number of cells in the S phase ($FxCycle^{medium/low}EdU^{high}$), whereas no difference was observed between the treated and untreated PMWK ($ITK_{LO}$) cell cycle profiles (FIG. 8A). The FXcycle and EDU incorporation data was further analyzed by quantitating the number of cellular particles that had less than the normal amount of DNA in them. There was no change in the amount of particles that contained less than the regular amount of DNA and would be produced by apoptosis or another cell death process. To further assess whether apoptosis was playing a role in the cell cycle changes, the same cell lines that were utilized for the cell cycle experiments were also used to assess the level of caspase 3/7 activity in the cells (FIG. 8B). No consistent effects by any of the shRNAs on the caspase levels were noted.

6.1.15. PTEN/BRAF Mouse

All animal studies were approved by UNC-CH Institute for Animal Care and Use Committee prior to study start. PTEN/BRAF mice were bred in house, and tumors were induced with 1 ul of 20 mM Tamoxafen at 4 weeks near the base of the tail as previously described (Dankort et al., 2009 *Nat Genet* 41(5): 544-52).

6.1.16. Immunohistochemistry for ITK in Mouse Tumors

The AR-10 (BioGenex, HK057-5K) protocol was used for antigen retrieval from FFPE blocks (Shi et al., 1995). Briefly slides were rinsed in deionized water, then covered with Antigen Retrieval Citra Plus Solution, heated in a microwave until it comes to a rapid boil. The slide is heated for 10-15 minutes, cooled for 20-30 minutes at room temperature, rinsed with several changes of deionized water, and placed in IX PBS. Slides were blocked with DakoCytomation, X0909 (KEY 2006), and incubated with the primary antibody (ITK 1:1000; Abcam cat#ab32113) for 1 hour at RT (Room Temperature) or 4° C. overnight. The slides were blocked with Dako X0590 biotin blocking solution (Agilent Product No. X059030-2) and then Biogenex SuperSensitive™ Link-Label IHC Detection System (Biogenex cat #LA000-UL) was used to detect the bound antibodies.

6.1.17. Xenograft Mouse Model

Nude athymic animals were acquired through the UNC Animal Studies Core and are similar to Jackson Labs (strain 000819). Mice were aged to 10 weeks and inoculated in the hind flank with 500K cells suspended in a 50/50 solution of Hank's Solution plus 2% FBS and matrigel (BD cat#356234). Once weekly caliper measurements of the length and width of the tumors were recorded; volume was then calculated using the formula $((L^2) \times W)/2$. Treatment began when a tumor reached an approximate size of 60 mm$^3$. Mice received compounds orally via admixture with standard rodent diet (Research Diets, Inc; New Brunswick, N.J.) or the same diet for non-treated mice as per MP1U (mouse phase I unit) protocol (Roberts et al., 2012 *Clin Cancer Res* 18(19):5290-5303). Tissues were cut in half and either flash frozen and then stored at −80 or formalin-fixed/paraffin embedded.

6.2. Results 6.2.1. ITK is Expressed in Melanomas and Melanoma Cell Lines

Demethylation of gene promoters is associated with increases in the expression of the protein that is encoded by that gene. We previously reported (Conway et al., 2011, *Pigment Cell Melanoma Res* 24(2):352-360) that the ITK promoter was significantly demethylated in melanoma compared to in nevi (moles). This led us to investigate the presence of ITK protein in melanoma cell lines, nevi, and primary and metastatic melanomas. Dual fluorescent immunohistochemistry (IHC) was used to probe Tissue Microarrays (TMAs) containing 30 benign nevi, 22 primary melanomas, and 86 metastatic melanomas using the Rabbit monoclonal anti ITK (Y401) from Abcam. The results demonstrated that nevi contain little if any ITK staining while the median levels of ITK expression significantly increased in the primary and metastatic melanomas (p<0.001) (FIG. 1). No ITK staining was observed in normal skin surgical discard specimens including the melanocytes found in the skin samples (data not shown).

We also performed IHC staining of the TMA containing the 37 melanoma cell lines and 3 normal human melanocyte (NHM) cultures to identify the level of ITK protein in each (Table 1). In this set of experiments, analysis of the stained cell line TMAs detected ITK levels ranging from 30.4 to 4,941 in the melanoma cell lines. Using the IHC values for the ITK levels we were able to classify the cell lines as ITK$_{LO}$, ITK$_{INT}$, and ITK$_{HI}$. We define ITK$_{LO}$ cell lines as those having an ITK value of 30.4 to 40, ITK$_{INT}$ as those having an ITK value >40 to 100, and any cell line that has an ITK value >100 is considered ITK$_{HI}$.

To extend our findings further and investigate the expression of ITK in melanomas compared to nevi, representative tissue sections from benign nevi (n=30), primary melanomas (n=20), and metastatic melanomas (n=70) were probed with antibodies against ITK and S100, a marker for melanocytic cells, using two-color IF. Table 4 shows the clinical and histopathologic characteristics of the nevi, primary melanomas and melanoma metastases specimens used for staining.

As shown in Table 5, the mean ITK protein levels of nevi and melanomas were not significantly associated (all P>0.05) with age at diagnosis, sex, or anatomic site. Mean ITK levels of the primary melanomas were not associated with histologic subtype, Breslow thickness, ulceration, mitoses, tumor-infiltrating lymphocyte grade, pigmentation, or solar elastosis. Mean ITK levels of the metastatic melanomas were not associated with site of origin of the metastases or characteristics of the associated primary melanoma. Mean ITK protein levels were also not associated with BRAFV600E mutation status in either the primary or metastatic melanomas.

In one set of experiments, two molecular markers that were investigated for correlation with ITK expression were phosphoAKT (pAKT) and phosphoERK (pERK). Phospho AKT and pERK levels are frequently elevated in melanoma, indicating activation of the PI3K-AKT and RAF-MEK-ERK pathways respectively (Davies M A. 2012 *Cancer J* 18(2): 142-147). The total ITK protein concentration and the phosphoAKT concentration, which were both estimated from IHC, were positively correlated (p value <0.001) (FIG. 3A). Phospho AKT has been shown to be involved in melanoma initiation and progression and is thought to play an additional role in resistance to the BRAF inhibitor therapies. The correlation between pAKT and ITK levels suggests that in the melanoma cells ITK may be involved in the PI3K-pAKT pathway and may be a new therapeutic target for the pAKT signaling pathway in melanoma. The total ITK protein levels and the pERK levels, both estimated using IHC, did not correlate (data not shown).

6.2.2. ITK Protein Expression in Particular Immune Cell Subsets

The literature has established the involvement of the immune system in melanoma development and progression (McArthur and Ribas, 2013) as well as ITK's role in Th2-mediated responses (Sahu and August, 2009), which usually are associated with ineffective antitumor responses (Dai et al., 2013). For these reasons we were particularly interested in identifying, first, whether ITK expression in melanoma cells correlated with melanoma expression of immune regulatory molecules and, second, whether immune subsets in melanoma tumor biopsies expressed ITK. Regarding the former, we investigated melanoma expression of the programmed cell death 1 ligand 1 (PD-L) because it has both prognostic significance in melanoma and a biomarker role in predicting response to a growing class of inhibitors of the PDI-PD-L1 pathway with promising clinical activity (Callahan and Wolchok, 2013; Taube et al., 2012). IF analysis of melanoma metastases for PD-L expression in S100 positive cells showed that PD-L expression was positively correlated with ITK expression (r=0.468, Spearman correlation) (FIG. 3B). To examine whether immune subsets in tumor melanoma biopsies expressed ITK, we performed dual IF of ITK and markers of immune subsets on on 3 primary melanomas and 2 melanomas metastatic to lymph nodes from 5 different patients. While a few small mononuclear cells in melanomas expressed ITK, IF analysis for ITK colocalization in various immune cell subsets failed to identify ITK in CD3+, CD19+, CD68+, myeloperoxidase (MPO)+, mast cell tryptase (MCT)+, CD56+ or CD57+ cells, which correspond, respectively, to markers for T-cells, B-cells, macrophages, neutrophilic granulocytes, mast cells, and subsets of natural killer cells (data not shown). We therefore conclude that ITK may be expressed in less abundant immune cell subsets but not in a high percentage of infiltrating immune cells.

6.23. Genetic Alterations and Gene Expression Changes Associated with ITK Expression in Melanoma Cell Lines To investigate whether ITK expression is associated with a particular gene expression or gene mutation signature, we first probed a melanocyte-melanoma cell line array (CLA) with the ITK antibody using IF (Table 6). These melanoma cell lines had previously undergone next generation sequencing and whole gene expression profiling (Carson et al., 2012). Unlike the results in Table 1, the cell line array IF values in Table 6 are those after normalization across the CLAs and TMAs and whole tissue sections using standards. After normalization, the signal from three normal human melanocyte (NHM) cultures ranged from 30 to 59 (mean of 43.3) arbitrary IF units. As expected from our tumor tissue studies, ITK was highly expressed in melanoma cell lines. More specifically, the ITK signal from 38 of the melanoma cell lines ranged from about 34 to 5,550 units (mean of 312.3, median of 93.5). As shown in FIG. 2, ITK protein expression was confirmed in five of the melanoma cell lines by western blotting with the band intensities similar to the IF intensities in the CLA. On the western blot, a weak band staining for ITK was detected among the proteins from the PMWK cells that had stained at 35 arbitrary IF units, similar to that of the NHMs, in the CLAs. Stronger bands staining for ITK were observed in the A 375, SKMEL 147, RPMI 8322, and VMM 39 lanes, and these cell lines had ITK IF values ranging from 50 to 297 in the CLAs (data not shown). In this set of experiments, since the IF intensities for the amount of ITK in each cell line within the CLA varied, we used the ITK IF arbitrary units obtained for each cell line after normalization to classify them as ITK low ($ITK_{LO}$) (less than 43.3, the mean IHC value of the NHMs), intermediate ($ITK_{INT}$) (from 43.3, mean of the NHMs, through 86.6, twice the mean of the NHMs), or high ($ITK_{HI}$) (86.6 or greater, more than twice the NHMs or higher). There were no significant associations (all $P>0.05$) of ITK protein levels with NRAS and BRAF mutational status or CDKN2A, PTEN, or TP53 genetic alterations in the cell lines. Additionally we performed Quantitative Trait Analysis (QTA) to correlate ITK protein expression with gene expression data. The genes that were correlated (P value $<0.005$ correlation value) were investigated to determine if they were overrepresented in any Biologic Biochemical Image Database (BBID) (Becker et al., 2000), Kyoto Encyclopedia of Genes and Genomes (KEGG) (Kanehisa et al., 2004), BioCarta (Schaefer et al., 2009), Panther (Mi et al., 2007), or Reactome (Schaefer et al., 2009) pathways. None of the pathways contained enough of the genes in the QTA list to be statistically significant (P-value $<0.05$ after Bonferroni correction).

6.2.4. Small Hairpin RNA (shRNA) Knockdown of ITK Protein

In order to confirm that the immune active protein is in fact ITK and to elucidate the role(s) of ITK in melanoma, we utilized lentiviruses that contained shRNAs designed to knockdown ITK protein levels. A western was performed on cell lysates of the lentiviral transduced and parental melanoma cell lines to determine the amount of ITK protein remaining after introduction of the shRNA containing lentivirus. As seen in FIG. 4A, there was a dramatic decrease in the level of ITK protein in the VMM 39 cells containing three of four different shRNAs, ITK 4, 5, and 7 cell lines while the ITK 6 cell line did not show any appreciable ITK reduction. When the Western blot for the VMM 39 knockdown was quantitated, it was found that >90% of ITK was lost in the ITK 4, 5, and 7 cell lines with no discernible loss of ITK in the ITK 6 cell line compared to the parental cell line. Comparable results were noted in the RPMI 8322 cell line while the PMWK cell line did not show significant ITK levels before or after lentiviral transduction (data not shown). These results showed that ITK protein levels could be greatly reduced using shRNAs and suggested that the ITK 6 cell lines could be used as a negative control when compared to the ITK 4, 5, and 7 cell lines. Performing experiments using the four shRNA cell lines allowed us to determine if the observed effects were due to ITK specific repression or off target effects of a specific shRNA. Taken together these data confirm that ITK protein is present in the melanoma cells and validates the use of the Abcam Rabbit monoclonal anti ITK (Y401) to identify ITK in clinical samples. The results of the statistical analyses of the effects of ITK shRNAs on proliferation of melanoma cell lines are shown in Table 7A.

Due to the importance of cellular migration in metastasis and the physiologic role of ITK in T cell migration (Fischer et al., 2004; Gomez-Rodriguez et al., 2011), we investigated the effect of ITK expression on the motility of melanoma cell lines as defined with single-cell tracking (Wu et al., 2012). The VMM 39 ($ITK_{HI}$) and RPMI 8322 ($ITK_{HI}$) cell lines had a significantly decreased rate of migration when transduced with a ITK 4, 5 or 7 lentiviral clone compared to the corresponding ITK 6- or SCR-transduced cell lines or the non-transduced parental cell lines (FIG. 4E). Migration rates of the ITK 4, 5 or 7-transduced cells were significantly decreased ($P<0.001$) compared to the corresponding ITK 6- or SCR-transduced cell lines or the parental cell lines (FIG. 4E). In contrast, no significant changes in the migration of the PMWK cells were observed following transduction with any of the lentiviral clones. The results for the statistical analyses of ITK shRNA effects on the proliferation and migration of melanoma cell lines are shown in Tables 7A and 7B.

6.2.5. The Use of BI 10N, a Small Molecule Inhibitor of ITK, to Decrease ITK Activity in Cells To assess the effect of pharmacologic inhibition of ITK activity in melanoma preclinical models, we used BI 10N, which has been previously shown to inhibit ITK's phosphoryl-transfer activities (Kashem et al., 2007; Riether et al., 2009). We investigated the potency and selectivity of BI 10N against 56 kinases using a cell-free assay (Table 8A). IC50s were measured on the kinases most potently inhibited by BI 10N in the initial screen with 200 nM BI 10N (Table 8B), and tight binding studies were performed as needed (Table 8C). BI 10N is a highly selective inhibitor of ITK and this affinity is described by a K of 8.6 pM. Of the 56 protein kinases tested, BI 10N is at least 1000-fold more selective for ITK than 51 of the protein kinases and about 10-fold selective over three members of the neurotrophic tyrosine receptor kinase family (TRKA, TRKB, TRKC) and the Src family member non-receptor tyrosine kinase (SFK) YES.

In T cells ITK undergoes phosphorylation-activation in two sequential steps following its docking onto the SLP76/LAT complex. First, ITK is trans-phosphorylated at Tyr511 by the Src-family kinase Lck and then it undergoes autophosphorylation at Tyr180 (Wilcox and Berg, 2003). To assess whether ITK is constitutively active in ITK-expressing melanoma cells and is therefore phosphorylated at both Tyr-180 and 511 residues, we probed whole cell lysates from high ITK-expressing melanoma cell lines with the commercially available antibodies 4F10 and 8D11. These antibodies have been raised against Bruton's tyrosine kinase Tyr-223 and Tyr-551, which are homologous to Tyr-180 and Tyr-511 ITK phosphoepitopes. Despite previous reports (Wilcox and Berg, 2003), we were unable to definitively identify bands that migrate around the molecular weight of ITK using these antibodies.

Therefore, alternatively, we performed two-dimensional electrophoresis on whole cell lysates obtained from RPMI 8322 cells that had been treated with phosphatase or different concentrations of BI 10N for 3 days prior to harvest followed by western blot analysis using the ITK antibody. In untreated RPMI 8322 cells, two charge isoforms that migrated with the appropriate weight for ITK were identified by immunoblot analysis. Upon increasing concentrations of BI 10N≥25 nM, one of the ITK isoforms disappeared, suggesting loss of the more negatively charged phosphorylated ITK isoform. Treatment with lambda phosphatase resulted in the loss of the same ITK isoform. These observations indicate that the formation of the phosphorylated (active) form of ITK is inhibited in the presence of ≥25 nM of BI 10N (data not shown).

6.2.6. Reduction of Melanoma Cell Line Proliferation Due to the Loss of ITK Using shRNAs Previous work has shown that ITK plays an integral role in the increase in proliferation rates in T cells after the activation of the T cell receptor (TCR) (Woods et al., 2001 EMBO J 20:1232-1244). FIG. 4B shows that melanoma cell lines VMM 39 and RPMI 8322 (ITK$_{HI}$) transduced with shRNAs ITK 4, 5 and 7, which greatly reduce ITK levels, proliferate at a rate approximately 50% that of the control cells with normal ITK expression. None to little effect on cell proliferation was observed in PMWK (ITK$_{LO}$) cell lines upon transduction with shRNAs ITK 4, 5 and 7. No effect on proliferation was seen when the ITK$_{HI}$ or ITK$_{LO}$ cell lines were transduced with ITK6. The slower proliferation of ITK$_{HI}$ cell lines when transduced with each of three shRNA (ITK 4, 5, and 7) that deplete ITK, and their unimpeded proliferation when transduced with ITK 6 suggest that the proliferation decrease is due to specific ITK loss and not an off target or a general lentivirus transduction effect.

6.2.7. The Effects of ITK on Cellular Motility Using shRNAs

ITK has been shown to play a role in cytoskeletal rearrangement and in the motility of T cells (Woods et al., 2001 EMBO J 20:1232-1244). Due to the importance of cellular migration in metastasis we investigated the role of ITK on the motility of melanoma cell lines. As in the case for cell proliferation, ITK 4, 5 and 7 lentiviral clones had a decreased rate of migration in the VMM 39 (ITK$_{HI}$) and RPMI 8322 (ITK$_{HI}$) cell lines compared to the corresponding ITK6 cell lines and parental cell lines. Migration rates in the 4, 5 and 7 cells were seen to drop by about 50% (p value <0.0001 compared to ITK6 and parental cell lines) when ITK was depleted by the shRNA constructs (FIG. 4C). In contrast, none of the lentiviral clones altered the proliferation or migration of the PMWK (ITK$_{LO}$) cell line.

6.2.8. Selectivity of the ITK Inhibitor BI 10N

BI 10N, a 5-aminomethylbenzimdazole derivative, is a small molecule selective inhibitor of ITK characterized by an EC$_{50}$ of 1 nM (Riether et al., 2009). The selectivity of this inhibitor was investigated by testing the potency of the inhibitor at two concentrations with 53 kinases by Carna Biosciences (MA) (Table 2). IC50s were also measured on the nine of the most potently inhibited by BI 10N and four additional kinases of interest by Carna Biosciences. The results are summarized in Table 2. While BI 10N looks to be equipotent with a number of kinases other than ITK, further study is needed since BI 10N is a time-dependent inhibitor of ITK and TRKA and BI 10N's potency with the two enzymes is underestimated.

6.2.9. Reduction of Melanoma Cell Line Migration in the Presence of an ITK Kinase Inhibitor We repeated the single cell migration experiment that utilized the shRNA cell lines and used BI 10N instead to inhibit ITK kinase activity in the parental melanoma cell lines (FIG. 5A). Similar to the results with the shRNA clones, migration by the ITK$_{HI}$ cell lines (VMM39, RPMI 8322, and SKMEL 153) decrease about 50% in the presence of 10-25 nM of BI 10N while migration by the ITK$_{LO}$ cell lines (SKMEL 131 and PMWK) do not decrease in the presence of the same concentrations of inhibitor. Migration by the ITK$_{INT}$ cell lines (A375 and SKMEL 103) were also unaffected by 10-25 nM of BI 10N.

6.2.10. Reduction of Cellular Proliferation in the Presence of an ITK Kinase Inhibitor For these studies, BI 10N was added at the inception of the assay. As seen during the equivalent shRNA studies, in the presence of 50 nM of BI 10N, the doubling time of the ITK$_{HI}$ cell lines (VMM 39, RPMI 8322, and SKMEL 153) increased about 50%. The proliferation of the ITK$_{INT}$ cell line (A375) decreased similarly to the ITK$_{HI}$ cell lines in the presence 50 nM BI 10N. The ITK$_{LO}$ cell lines (PMWK and SKMEL 131) did not increase their doubling time in the presence of inhibitor as high as 150 nM.

6.2.11. ITK Inhibition Effects on Anchorage Independent Growth

An additional measure of the malignancy of a cell line is its ability to grow in a semi solid matrix. We investigated if ITK kinase activity influenced the ability of melanoma cell lines to grow in soft agar. We were unable to perform the matrix growth assay with the shRNA cell lines since the effects of shRNA mediated gene suppression are transient. The ITK levels in the cells would recover from the shRNA knockdown prior to the completion of the soft agar assays. The amount of BI 10N needed to decrease the number of colonies formed by 50% was 25 nM for the PMWK (ITK$_{LO}$) cell line and at 50 nM BI 10N for the ITK$_{HI}$ cell line (RPMI 8322) (FIG. 5C). This finding suggests that even low levels ITK may stimulate anchorage independent growth of PMWK cells.

Cell cycle analysis of VMM 39 and RPMI 8322 (ITK$_{HI}$) cell lines using EdU labeling and FxCycle Violet staining indicated that, similar to the shRNA studies, treatment of the cells with BI 10N increased the percentage of cells in the G0/G1 phase and decreased the percentage of cells in the S phase in a dose-dependent manner (FIG. 5D). No cell cycle changes were observed between the treated and untreated PMWK (ITK$_{LO}$) cells.

The effects of BI 10N on melanoma cell migration were determined for PMWK (ITK$_{LO}$), VMM 39 (ITK$_{HI}$), RPMI 8322 (ITK$_{HI}$) (FIG. 5C), and additional melanoma cell lines (FIG. 5C). Similar to the results with the shRNA clones, the migration by the ITK$_{HI}$ cell lines (VMM39, RPMI 8322, and SKMEL 153) decreased about 50% in the presence of 10-25 nM of BI 10N while smaller changes in the migration of a ITK$_{INT}$ cell line (A375) and ITK$_{LO}$ cell lines (SKMEL 103, SKMEL 131 and PMWK) were observed and required a concentration of 150 nM or greater BI 10N. The statistical analyses of the effects of BI 10N at different concentrations on the rate of migration by the melanoma cell lines are shown in Tables 9A and 9B.

Since BI 10N inhibits the proliferation and migration of the ITK$_{HI}$ cell lines, we investigated whether this inhibitor influences the ability of the PMWK (ITK$_{LO}$) and RPMI 8322 (ITK$_{HI}$) cell lines to grow in soft agar. For these studies BI 10N was incorporated into the agarose layers and the media to provide a consistent inhibition of ITK. The inhibition of anchorage-independent growth of both cell lines was strongly decreased by BI 10N. The concentration of BI 10N needed to achieve anchorage-independent growth inhibition was lower for the PMWK (ITK$_{LO}$) cells than for the RPMI 8322 (ITK$_{HI}$) cells. This finding suggests that even low levels of ITK may stimulate anchorage-independent growth by PMWK cells.

To investigate the impact of ITK inhibition by BI 10N on the ERK and AKT signaling pathways, which are frequently misregulated in melanoma, the ITK$_{HI}$ melanoma cell lines (VMM 39 and RPMI 8322) were grown in the presence of increasing BI 10N concentrations. Western blot analysis was performed on whole cell lysates from these cells using antibodies against ERK, pERK$^{Thr202/Tyr204}$, AKT, and pAKT$^{Ser473}$. No significant effects of BI 10N administered at concentrations as high as 50 nM and for 3 days were detected on the activation status of ERK and AKT (data not shown).

6.2.12. ITK Kinase Activity Stimulates the Growth of Tumors in Xenograft Mouse Models BI 10N is bioavailable (Riether et al., 2009) and so was incorporated into the food for the experimental mice and was utilized for studies in xenograft models (FIG. 6A-C). Tumors grew steadily in control mice that received normal food in all three xenograft models (VMM 39 (ITK$_{HI}$), RPMI 8322 (ITK$_{HI}$) and A375 (ITK$_{INT}$)). At a level of 15 mg per kg, the ITK inhibitor BI 10N significantly slowed the tumor's growth in the cell lines with high ITK levels, RPMI 8322 and VMM 39, but did not slow the growth of the cell line with an intermediate level of ITK, A375.

6.2.13. ITK Inhibitor BI 10N Slows the Progression of Melanoma in PTEN/BRAF Mice PTEN/BRAF mice lack PTEN, and V600E BRAF is induced using the CRE LOX system by exposure of the mice to Tamoxafen. These mice form spontaneous tumors following their exposure to Tamoxafen. Some of these spontaneous tumors were harvested and IHC was performed to determine if ITK was present in any of the tumors. Strikingly, high levels of ITK were detected in all of the primary tumors (data not shown), indicating that PTEN/BRAF mice are suitable for investigations of testing the efficacy of ITK inhibitors. The BI 10N at a dose of 15 mg per kg profoundly retarded the progression of tumors in the mice compared to the no treatment group (FIG. 7A). These results suggest that ITK stimulates the growth of tumors in the PTEN/BRAF GEM mouse model and that this stimulatory effect can be blocked by ITK inhibitors. FIG. 7B shows that an ITK inhibitor performs better in vivo than MEK inhibitor AZD6244 (selumentinib) and V600E BRAF inhibitor PLX4032 (vemurafenib).

6.2.14. ITK is Expressed in a Variety of Human Solid Tumors

The Abcam Rabbit monoclonal anti ITK (Y401) was used to probe TMAs containing samples from a variety of solid human tumors. The TMAs were scored by a licensed pathologist as to the amount of staining present in tumor cells (0, 1+, 2+, or 3+). These results are presented in Table 3A, 3B and 3C and indicate that ITK is expressed in a variety of human solid tumors. Given the correspondence of the Abeam Rabbit monoclonal anti ITK (Y401) staining with shRNA and BI 10N efficacy data and the presence of ITK in spontaneous tumors seen in the PTEN/BRAF GEM mouse model, the validity of utilizing the Abeam Rabbit monoclonal anti ITK (Y401) staining to identify ITK expression is established. Taken together, these data provide strong evidence that ITK is expressed in a large number of human tumors.

6.2.15. ITK is Highly Expressed in ER(−) PR(−) Breast Tumors

In these experiments dual immunofluorescence studies of breast cancer TMA and ITK were performed.

Breast cancer tissue micro arrays were constructed from samples were obtained from the UNC Hospitals surgical pathology archives. The antibodies used were rabbit monoclonal anti ITK Abeam (clone Y401, #ab32039) and ready to use mouse monoclonal anti cytokeratin (CK) antibodies Leica Microsystems Inc. (clone AE1/AE3, #PA0909, Norwell Mass.). Dual immunofluorescence (IF) was carried out in the Bond fully-automated slide staining system (Leica Microsystems Inc., Norwell Mass.). Slides were deparaffinized in Bond dewax solution (AR9222) and hydrated in Bond wash solution (AR9590). Antigen retrieval for ITK was performed for 30 min at 100° C. in Bond-epitope retrieval solution 2 pH9.0 (AR9640). After pretreatment, slides were first incubated with ITK antibody (1:3000) followed with Bond polymer (kit DS9800) and the tyramide Cy5 (#SAT705A001EA, PerkinElmer, Boston, Mass.). After completion of ITK staining unmasking of CK was done for 15 min using Bond epitope retrieval solution 1 (pH6.0 AR9661). CK antibody (RTU) was applied for 1 h, followed with Alexa555 labeled goat anti mouse secondary antibody (#A21424, Life Technologies, Grand Island, N.Y.). Nuclei were stained with Hoechst 33258 (#H3569, Life Technologies, Grand Island, N.Y.). The stained slides were mounted with ProLong Gold antifade reagent (#P36934, Life Technologies, Grand Island, N.Y.). High resolution acquisition of fluorescently stained TMA slides (20× objective) in the DAPI, Cy3 and Cy5 channels and TMA segmentation was performed in the in the Aperio-FL (Aperio Technologies, Vista, Calif.). TMA spot images were submitted for analysis through Spectrum using HistoRx AQUA software version 2.2 according to the AQUAnalysis™ user guide (Aperio Edition; Rev. 1.0, CDN0044, HistoRx). Expression of ITK labeled by Cy5 (red) was measured in CK-specific tumor mask labeled by Alexa555 (green).

The breast cancer results are shown in Table 10 and FIGS. 10A-10C. These studies indicate that ITK inhibitor treatment would be particularly well suited for ER(−) and/or PR(−) breast cancer patients.

6.3. Discussion

In this study, we provide several lines of evidence that ITK, a gene whose promoter CpG sites are hypomethylated in melanomas compared to benign nevi, is an important therapeutic target in melanoma and other solid tumors. Specifically, we show that ITK protein expression increased with progression from nevus to primary melanoma and even more so to metastatic melanoma. The data in this document also demonstrate, utilizing the Abcam Rabbit monoclonal anti ITK (Y401), that ITK protein is present in the majority of melanoma cell lines with an intermediate or high intensity (Table 1). Three of four shRNAs designed to block ITK expression reduce staining by the Abcam Rabbit monoclonal anti ITK (Y401) by 90% and significantly reduce the proliferation and migration of ITK high expressing cell lines that are expressing the three effective shRNAs. Further, the selective small molecule BI 10N reduces the proliferation and migration of ITK high expressing cell lines to the same levels of the same cell lines producing the shRNAs. When high expressing ITK melanoma cell lines form tumors in Xenograft models, the growth of those tumors are strongly slowed by inclusion of the BI 10N ITK inhibitor in the mouse diets. Finally, PTEN/BRAF mouse melanomas express ITK, and tumor growth is slowed in the PTEN/BRAF mice fed the BI 10N ITK inhibitor.

The data in this document also provide strong evidence that ITK is not expressed by normal nevi but is typically expressed at intermediate levels in primary melanocytic tumors and is predominantly expressed at high levels in metastatic melanoma (FIG. 1). This pattern of expression is consistent with ITK increasing the metastatic potential of melanoma and also with the stimulatory effects of ITK activity detailed in the results. These proposals for ITK increasing proliferation and migration in tumors are consistent with the effects of ITK activity in T cells (Berg et al., 2005 Annu Rev Immunol 23:549-600). The finding that ITK is expressed at high levels in all of the spontaneous tumors of the PTEN/BRAF mice mirrors these findings. The success of the BI 10N ITK inhibitor in drastically slowing the growth of these tumors gives hope that ITK inhibitors could help manage patients having malignant melanoma. The expression of ITK in a large number of solid tumors from patients has not been reported before and is particularly striking given the normal restricted expression of ITK in a small subset of cells from a different developmental lineage.

Unregulated tyrosine kinases have been identified in tumors a number of times before and are associated with oncogenic processes in many cases (Casaletto and McClatchey 2012, *Nat Rev Cancer* 12(6):387-400). It is therefore reasonable to conclude that the high levels of ITK identified in human tumors results in unregulated ITK tyrosine kinase activities that promote oncogenesis. Under the conditions of the xenograft studies, BI 10N may be inhibiting any present TRK family members and YES in addition to ITK. However, there is no evidence or expectation that A375, VMM 39 and RPMI 8322 cells differ in their expression of TRK family members or YES and yet only the growth of VMM39 and RPMI, both $ITK_{HI}$ cell lines, containing tumors were slowed by BI 10N. If TRK or YES inhibition were responsible for the attenuation of tumor growth in the xenograft tumors then the efficacy of BI 10N would be expected to be equal for all three cell lines. Similarly, the effects of BI 10N on the melanoma cell lines were not equal, again suggesting that the effects seen resulted from BI 10N inhibition of ITK.

Furthermore, suppression of ITK expression or kinase function in melanoma cells produced G0/G1 cell cycle arrest and decreased cell proliferation and motility without any effects in cell death. Finally, inhibition of ITK activity using BI 10N delayed tumor growth in melanoma xenografts and the Tyr-Cre/Pten$^{null}$/BraF$^{600E}$ mouse model.

To our knowledge, this is the first report that ITK, a non-receptor TEC family tyrosine kinase previously thought to be solely expressed by white blood cells, is highly expressed in a solid tumor malignancy, such as melanoma. One group reported that ITK mRNA was expressed at a low level in colon cancer extracts but perceived that its expression was probably derived from contaminating host immune cells. Chen et al. 1999 *Int J Cancer* 83, 579-584. Previous studies about the putative oncogenic role of ITK have been limited to (i) descriptions of its increased expression in T-cell malignancies (Guo et al., 2012; Kaukonen et al. 1999 *Leukemia & Lymphoma* 32, 513-522; Shin et al., 2007. Blood 110, 3015-3027); (ii) reports that it is part of a chimeric protein arising from the chromosomal translocation t(5:9)(q33:q22) identified in 17% of peripheral T-cell lymphomas (Streubel et al. 2006 Leukemia 20, 313-318); and (iii) findings that ITK inhibitors have activity against T cell malignancies (Dubovsky et al., 2013; Guo et al., 2012). We are not aware of previous articles measuring the effects of ITK inhibition on solid tumor malignancies.

Our review of the 226 melanoma samples that have undergone next generation sequencing and putative copy-number alteration analysis using the GISTIC tool as part of the Cancer Genome Atlas Project (www.cbioportal.org) revealed no evidence of copy number alterations for the ITK gene and only 7% incidence of somatic mutations (predominantly of the missense type which occur across the entire ITK gene) with relatively low mutation allele frequency (mean is 0.24 range 0.03-0.56). The lack of ITK gene copy number alterations together with the correlation of ITK protein expression with the methylation of CpG sites in the ITK promoter in melanomas and nevi suggest that epigenetic rather than genetic mechanisms, at least in part, account for the expression of ITK in melanoma.

With respect to the association of ITK with the PI3K-Akt signaling pathway, noteworthy was the significant positive correlation between activated Akt and ITK protein expression. In T cells, an initial step of ITK activation is the kinase binding to phosphatidylinositol (3,4,5) trisphosphate (PIP3) produced by PI3K at the plasma membrane. Andreotti et al., 2010 Cold Spring Harb Perspect Biol 2, a002287. Interestingly, the effects of ITK on the proliferation and migration of melanoma cells are consistent with its activity in T cells. The lack of association between PTEN and ITK protein expression in melanoma cells may imply, first, that low PTEN protein expression is not the same as PTEN gene copy number loss, which is a better surrogate biomarker for Akt activation. In accordance with this was the remarkable finding that ITK protein expression was very high in melanomas derived from the CRE-ER$^{T2}$ B-Raf$^{L/+}$Pten$^{L/L}$ mouse model. Second, the low expression of PTEN protein alone may not be sufficient to activate Akt. This is in agreement with our results about the lack of significant correlation between PTEN and pAkt expression in melanomas (data not shown).

In addition, we report a correlation between PD-L and ITK protein expression and also found a significant correlation between activated Akt and PD-L protein levels (data not shown). However, BI 10N did not change the expression of PD-L or Akt or Erk activation in the melanoma cells, suggesting that ITK kinase activity does not regulate any of these processes. These observations are consistent with PI3K regulating PD-L expression, Akt or Erk activation and ITK protein levels (Davies, 2012; Jiang and Liu 2008 Biochim Biophys Acta 1784, 150-158; Parsa et al., 2007 *Nat Med* 13, 84-88)

The oncogenic properties of ITK in melanoma led us to investigate the impact of pharmacologic ITK inhibition in melanoma and several ITK inhibitors that were developed over the years for Th2 dominant autoimmune, inflammatory, and infectious diseases were available (Charrier and Knegtel, 2013; Lo, 2010; Vargas et al., 2013). In this work, we characterized the kinase inhibitor profile of BI 10N, a small molecule selective inhibitor of ITK that has been previously used in animal studies (Riether et al., 2009). BI 10N was highly selective for ITK over a large panel of kinases including SRC family kinases (SFK) SRC, LCK, and FYN but not for 3 TRK family members and the SFK member YES. Although TRKA and TRKB are highly expressed in melanoma (www.proteinatlas.org), the effects of BI 10N are likely mediated through the inhibition of ITK as the effects of BI10N on melanoma cells are similar to those achieved with ITK depletion using shRNAs.

ITK plays an important role in the pathophysiology of the immune system. Therapeutic targeting of ITK in melanoma should critically consider its bystander effect on the host immune response given the overwhelming evidence that a functioning immune system is fundamental for the control of this disease. Our preliminary investigation failed to show high abundance of ITK expression in major tumor-infiltrating immune cell subsets such as T cells, polymorphonuclear cells, mast cells, natural killer cells and macrophages. Further, ibrutinib, a confirmed irreversible inhibitor of Bruton tyrosine kinase (BTK) and ITK (Dubovsky et al., 2013), did not result in increased incidence of grade 3 or higher infections. Byrd et al., 2013 *N Engl J Med* 369, 32-42.

In summary, ITK appears to be a driver of melanoma and a potential therapeutic target as demonstrated by its expression in all the metastatic melanomas examined and efficacy of the BI 10N small molecule inhibitor of ITK in mouse melanoma models. Clinical-grade ITK inhibitors are under study for inflammatory disorders and T-cell leukemia or lymphoma. In particular ibrutinib (IMBRUVICA, Pharmacyclics, Inc.), an irreversible inhibitor of BTK and ITK that has demonstrated clinical activity and tolerability in B-cell and T-cell malignancies in phase III trials (Byrd et al., 2013), received U. S. Food and Drug Administration accelerated approval for the treatment of patients with mantle cell lymphoma who have received at least one prior therapy.

Clinical trials using such agents in human melanoma alone or combination with existing therapies should be considered.

TABLE 1

ITK expression in cell lines by antibody immunofluorescence

| Cell Line | ITK Value | Cell Line | ITK Value | Cell Line | ITK Value |
|---|---|---|---|---|---|
| NHM 7 | 26.7 | NHM 12 | 52.3 | WM 1361A | 154.5 |
| SKMEL 131 | 30.4 | SKMEL 173 | 55.7 | SKMEL 181 | 170.3 |
| SKMEL 187 | 30.9 | SKMEL 24 | 56.8 | WM 35 | 181.1 |
| mel 505 | 31.4 | WM 1158 | 57.1 | RPMI 8322 | 193.9 |
| PMKW | 31.5 | SKMEL 130 | 58.7 | SKMEL 190 | 201.2 |
| SKMEL 103 | 36.1 | UACC 257 | 61.3 | VMM 39 | 264.4 |
| NHM 11 | 36.6 | SKMEL 235 | 68.5 | SKMEL 119 | 271 |
| SKMEL 100 | 41.5 | SKMEL 23 | 97.9 | MEL 537 | 298.9 |
| SBC 12 | 41.7 | WM 1232 | 102.9 | MALME 3M | 332.5 |
| SKMEL 78 | 42.1 | SKMEL 239 | 107.2 | WM 2664 | 571.2 |
| A375 | 44.5 | MEL 224 | 109.6 | SKMEL 186 | 1284.4 |
| SKMEL 28 | 46.3 | A2058 | 115.4 | SKMEL 153 | 4941 |
| SKMEL 147 | 48.8 | SKMEL 115 | 134.2 | | |
| SKMEL 27 | 50.7 | RPMI 7951 | 135.3 | | |

Abbreviation: NHM, normal human melanocyte culture.

TABLE 2

Kinase selectivity of BI 10N

| Kinase | IC50 (M) UNC10161229A | Positive Control* |
|---|---|---|
| ABL | 2.35E−08 | 8.15E−08 |
| FGFR1 | 5.97E−08 | 2.98E−09 |
| FYN | 2.42E−08 | 2.32E−09 |
| IGF1R | 8.86E−07 | 3.98E−08 |
| ITK | 4.86E−10 | 3.04E−09 |
| LCK | 1.06E−08 | 1.71E−09 |
| PDGFRα | 1.01E−08 | 2.00E−10 |
| SRC | 3.76E−09 | 4.98E−09 |
| TRKA | 4.59E−10 | 4.21E−10 |
| YES | 9.93E−10 | 2.52E−09 |
| HGK | 1.21E−08 | 1.16E−09 |
| IRAK4 | 3.14E−09 | 1.01E−08 |
| MST1* | 2.60E−08 | 3.43E−09 |
| TSSK1 | 2.86E−08 | 2.64E−10 |

The positive control was Staurosporine for all enzymes except MST1, for which it was K252b Table 3A. Ectopic Expression of ITK in a Variety of Solid Tumors.

Tissue Microarrays of various human solid tumors were stained using DAB with ITK antibodies to assess the presence of ITK. The staining of each sample was scored by a licensed pathologist. The samples were stained for ITK and scored 0 and 1+ if little to no staining was present and 2+ to 3+ if significant ITK was present.

TABLE 3A

ITK is expressed in multiple solid tumors

| | Breast Cancer | | Uterine Cancer | | Gastric Cancer | |
|---|---|---|---|---|---|---|
| Scoring | No. | Percent | No. | Percent | No. | Percent |
| 0 | 24 | 35.8 | 6 | 5.6 | 27 | 29.7 |
| 1+ | 8 | 11.9 | 8 | 7.4 | 32 | 35.2 |
| 2+ | 16 | 23.9 | 66 | 61.1 | 31 | 34.1 |
| 3+ | 19 | 28.4 | 28 | 25.9 | 1 | 1.1 |
| Total | 67 | | 108 | | 91 | |

| | NSCLC | | Head and Neck Cancer | | Colorectal Cancer | |
|---|---|---|---|---|---|---|
| Scoring | No. | Percent | No. | Percent | No. | Percent |
| 0 | 3 | 11.1 | 9 | 34.6 | 18 | 25.4 |
| 1+ | 4 | 14.8 | 4 | 15.4 | 15 | 21.1 |
| 2+ | 8 | 29.6 | 3 | 11.5 | 15 | 21.1 |
| 2-3+ | 2 | 7.4 | 1 | 3.8 | 13 | 18.3 |
| 3+ | 10 | 37 | 9 | 34.6 | 10 | 14.1 |
| Total | 27 | | 26 | | 71 | |

Abbreviation: NSCLC, Non-small cell lung cancer

TABLE 3B

Expanded studies of expression of ITK in a variety of solid tumors. Solid Primary Tumors Expressing ITK by Immunohistochemistry

| Primary Tumor | Percent of samples 2+ or greater | Number of samples |
|---|---|---|
| Lung Cancer, Squamous Cell Carcinoma | 100 | 3 |
| Lung Cancer, Adenocarcinoma | 100 | 3 |
| Ovarian Cancer, Serous Carcinoma | 92.9 | 14 |
| Colon Adenocarcinoma | 66.7 | 3 |
| Prostate Adenocarcinoma | 66.7 | 3 |
| Pancreatic Adenocarcinoma | 56.3 | 18 |
| Ovarian Cancer, Clear cell carcinoma | 52.9 | 17 |
| Ovarian Cancer, Endometrioid carcinoma | 50 | 6 |
| Uterine Cancer | 50 | 4 |
| Ovarian Cancer, Mucinous Carcinoma | 27.8 | 18 |
| Skin Cancer, Basal Cell Carcinoma | 0 | 10 |
| Skin Cancer, Squamous Cell Carcinoma | 0 | 10 |
| Skin Cancer, Cutaneous T-cell Lymphoma | 0 | 5 |

TABLE 3C

Additional solid tumors expressing ITK by immunohistochemistry (IHC).

| Tumor | Percent of samples 2+ or greater | Number of Samples |
|---|---|---|
| Bladder Cancer, Transitional Cell Carcinoma | 100 | 1 |
| Thyroid Cancer, Follicular Carcinoma | 100 | 1 |
| Larynx Cancer, Squamous Cell Carcinoma | 100 | 2 |
| Thyroid Cancer, Papillary Carcinoma | 100 | 2 |
| Brain Tumor, Glioblastoma | 100 | 9 |
| Brain Tumor, Astrocytoma | 75 | 4 |
| Breast Cancer, multiple subtypes | 66.7 | 9 |
| Neuroendocrine Carcinoma | 50 | 2 |
| Renal Carcinoma | 10.3 | 29 |
| Fallopian tube Cancer, Serous carcinoma | 0 | 1 |
| Hepatocellular Carcinoma | 0 | 2 |

TABLE 4

Clinical and Histologic Characteristics of Cutaneous Melanocytic Nevi, Primary Melanomas, and Melanoma Metastases Evaluated Using Immunohistochemistry

| Characteristic | n (%) | | |
|---|---|---|---|
| | Nevi N = 30 | Primary Melanomas N = 20 | Melanoma Metasases* N = 70 |
| Sex | | | |
| Male | 12 (40) | 11 (45) | 46 (66) |
| Female | 18 (60) | 9 (55) | 24 (34) |
| Age at diagnosis of mole or primary melanoma | | | |
| ≤40 yrs | 25 (83) | 5 (25) | 16 (23) |
| >40 yrs | 5 (17) | 15 (75) | 54 (77) |
| Anatomic site of mole or primary melanoma | | | |
| Head/neck | 10 (33) | 5 (25) | 25 (36) |
| Trunk | 15 (50) | 6 (30) | 23 (33) |
| Extremities | 5 (17) | 9 (45) | 18 (26) |
| Metatstasis with unknown primary | na | na | 4 (6) |
| Melanoma histologic subtype of primary melanoma | | | |
| Superficial Spreading | na | 10 (50) | 19 (27) |
| Nodular | na | 1 (5) | 9 (13) |
| Lentigo maligna | na | 3 (15) | 5 (7) |
| Acral lentiginous/unclassified/other | na | 6 (30) | 25 (36) |
| Subtype of primary not available | na | na | 12 (17) |
| Melanocytic nevus type | | | |
| Intradermal | 9 (30) | na | na |
| Compound | 12 (40) | na | na |
| Compound with congenital pattern | 9 (30) | na | na |
| Melanoma BRAFV600E status** | | | |
| Wildtype (BRAFV600E negative) | nd | 14 (70) | 47 (67) |
| BRAFV600E positive | nd | 6 (30) | 23 (33) |
| Breslow thickness of primary melanoma, mm | | | |
| 0.01 to 2.00 | na | 6 (30) | 25 (36) |
| >2.00 | na | 14 (70) | 35 (50) |
| Breslow depth of primary not available | na | na | 10 (14) |
| Ulceration of primary melanoma | | | |
| Absent | na | 12 (60) | 23 (33) |
| Present | na | 8 (40) | 22 (31) |
| Ulceration status of primary not available | na | na | 25 (30) |
| Mitoses of primary melanoma | | | |
| Absent | na | 2 (10) | 6 (9) |
| Present | na | 18 (90) | 38 (54) |
| Mitotic rate of primary not available | na | na | 26 (37) |
| Tumor infiltrating lymphocyte grade of primary melanoma | | | |
| Absent | na | 9 (45) | nd |
| Nonbrisk or brisk | na | 11 (55) | nd |
| Pigment of primary melanoma | | | |
| Absent | na | 4 (20) | nd |
| Present | na | 16 (80) | nd |
| Solar Elastosis of primary melanoma | | | |
| Absent | na | 10 (53) | nd |
| Mild to moderate or severe | na | 9 (47) | nd |
| Metastatic tissue source | | | |
| Lymph node | na | na | 31 (44) |
| Skin | na | na | 21 (30) |
| Lung | na | na | 6 (9) |
| Gastrointestinal, soft tissue | na | na | 12 (17) |

Abbreviations: na, not applicable; nd, not done.

*Age, site, histologic subtype, Breslow thickness, ulceration and mitoses are for the associated primary melanoma from the same patient. However, immunohistochemical stains for BRAF VE1, ITK, pAKT, pERK, PDL1, and PTEN were performed on the melanoma metastasis

**For the primary melanomas, BRAFV600E was determined by sequencing. For the metastatic melanomas, BRAFV600E status was determining through immunohistochemistry with the BRAF VE1 antibody. Details are in the methods.

TABLE 5

Relationship of ITK Protein Levels by Immunohistochemistry to Clinical Characteristics of Moles, Primary Melanomas and Melanoma Metastases

| Characteristic | Mean ITK Level +/− SE | | |
|---|---|---|---|
| | Nevi N = 30 | Primary Melanomas N = 20 | Melanoma Metasases* N = 70 |
| All specimens in each category | 79.6 +/− 12.6 | 215 +/− 23.8 | 696 +/− 30 |
| Sex | | | |
| Male | 83.3 +/− 23.1 | 244 +/− 30.7 | 695 +/− 35.3 |
| Female | 77.2 +/− 14.9 | 179 +/− 35.5 | 698 +/− 56.8 |
| P value, Wilcoxon rank-sum test | 0.88 | 0.13 | 0.95 |
| Age at diagnosis of mole or primary melanoma | | | |
| ≤40 yrs | 72.4 +/− 12.9 | 174 +/− 45.7 | 698 +/− 68.1 |
| >40 yrs | 116 +/− 38.8 | 229 +/− 27.8 | 695 +/− 33.7 |
| P value, Wilcoxon rank-sum test | 0.07 | 0.35 | 0.89 |

TABLE 5-continued

Relationship of ITK Protein Levels by Immunohistochemistry to
Clinical Characteristics of Moles, Primary Melanomas and Melanoma Metastases

| Characteristic | Mean ITK Level +/− SE | | |
| --- | --- | --- | --- |
| | Nevi<br>N = 30 | Primary<br>Melanomas<br>N = 20 | Melanoma<br>Metasases*<br>N = 70 |
| Anatomic site of mole or primary melanoma | | | |
| Head/neck | 101 +/− 25.4 | 201 +/− 39.2 | 685 +/− 53.1 |
| Trunk | 63.4 +/− 11.8 | 216 +/− 47.8 | 711 +/− 45.2 |
| Extremities | 86.2 +/− 46.3 | 222 +/− 39.9 | 644 +/− 57.1 |
| Metatstasis with unknown primary | na | na | 917 +/− 181 |
| P value, Kruskal-Wallis test | 0.33 | 0.96 | 0.41 |
| Melanoma histologic subtype of primary melanoma | | | |
| Superficial Spreading | na | (see below)** | 694 +/− 61 |
| Nodular | na | (see below)** | 636 +/− 68.1 |
| Lentigo maligna | na | (see below)** | 723 +/− 73.2 |
| Acral lentiginous/unclassified/other | na | (see below)** | 666 +/− 50 |
| Subtype of primary not available | na | na | 796 +/− 86 |
| P value, Kruskal-Wallis test | | | 0.53 |
| Melanoma histologic subtype of primary melanoma | | | |
| Superficial spreading melanoma | na | 221 +/− 31.4 | nd |
| Nodular, lentigo maligna, acral lentiginous, other subtypes | na | 209 +/− 37.4 | nd |
| P value, Wilcoxon rank-sum test | | 0.68 | |
| Melanocytic nevus type | | | |
| Intradermal | 68.3 +/− 16 | na | na |
| Compound | 93.2 +/− 25.5 | na | na |
| Compound with congenital pattern | 72.9 +/− 20.6 | na | na |
| P value, Kruskal-Wallis test | 0.96 | | |
| Melanoma BRAFV600 status*** | | | |
| Wildtype (BRAFV600E negative) | nd | 224 +/− 31.8 | 702 +/− 35 |
| BRAFV600E positive | nd | 194 +/− 30.3 | 684 +/− 58.3 |
| P value, Wilcoxon rank-sum test | | 0.55 | 0.67 |
| Breslow thickness of primary melanoma, mm | | | |
| 0.01 to 2.00 | na | 173 +/− 53.1 | 639 +/− 47 |
| >2.00 | na | 233 +/− 25.2 | 706 +/− 39.6 |
| Breslow thickness of primary not available | na | na | 804 +/− 104 |
| P value, Wilcoxon rank-sum test or Kruskal-Wallis test | | 0.24 | 0.18 |
| Ulceration of primary melanoma | | | |
| Absent | na | 180 +/− 26.9 | 661 +/− 53.6 |
| Present | na | 267 +/− 38.6 | 720 +/− 50.6 |
| Ulceration status of primary not available | na | na | 707 +/− 53 |
| P value, Wilcoxon rank-sum test or Kruskal-Wallis test | | 0.08 | 0.70 |
| Mitoses of primary melanoma | | | |
| Absent | na | 223 +/− 168 | 622 +/− 69.9 |
| Present | na | 214 +/− 22.8 | 675 +/− 42.8 |
| Mitotic rate of primary not available | na | na | 743 +/− 48.7 |
| P value, Wilcoxon rank-sum test or Kruskal-Wallis test | | 1.00 | 0.38 |
| Tumor infiltrating lymphocyte grade of primary melanoma | | | |
| Absent | na | 223 +/− 34.6 | nd |
| Nonbrisk or brisk | na | 208 +/− 34.1 | nd |
| P value, Wilcoxon rank-sum test | | 0.88 | |
| Pigment of primary melanoma | | | |
| Absent | na | 194 +/− 31.4 | nd |
| Present | na | 220 +/− 29 | nd |
| P value, Wilcoxon rank-sum test | | 0.89 | |
| Solar elastosis of primary melanoma | | | |
| Absent | na | 241 +/− 39 | nd |
| Mild to moderate or severe | na | 197 +/− 28.9 | nd |
| P value, Wilcoxon rank-sum test | | 0.50 | |

TABLE 5-continued

Relationship of ITK Protein Levels by Immunohistochemistry to
Clinical Characteristics of Moles, Primary Melanomas and Melanoma Metastases

| | Mean ITK Level +/− SE | | |
|---|---|---|---|
| Characteristic | Nevi N = 30 | Primary Melanomas N = 20 | Melanoma Metasases* N = 70 |
| Metastatic tissue source | | | |
| Lymph node | na | na | 710 +/− 47.1 |
| Skin | na | na | 711 +/− 45.6 |
| Lung | na | na | 612 +/− 155 |
| Gastrointestinal, soft tissue | na | na | 675 +/− 70.1 |
| P value, Kruskal-Wallis test | | | 0.91 |

Abbreviations: na, not applicable; nd, not done; SE, standard error.
*Age, site, histologic subtype, Breslow thickness, ulceration and mitoses are for the associated primary melanoma from the same patient. However, immunohistochemical stains for BRAF VE1, ITK, pAKT, pERK, PDL1, and PTEN were performed on the melanoma metastasis.
**For primary melanomas, superficial spreading was compared to all other melanoma subtypes due to small numbers in the other subgroups.
***For the primary melanomas, BRAFV600E was determined by sequencing. For the metastatic melanomas, BRAFV600E status was determining through immunohistochemistry with the BRAF VE1 antibody. Details are in the methods.

TABLE 6

Normalized ITK Protein Expression in Cell Lines by Single Fluorescent Immunohistochemistry

| Cell Line | BRAF/NRAS | ITK Value | Cell Line | BRAF/NRAS | ITK Value |
|---|---|---|---|---|---|
| *NHM 7 | nd | 30 | SKMEL 235 | BRAF (V600E) | 77 |
| SKMEL 131 | WT | 34 | SKMEL 23 | BRAF (G466A) | 110 |
| SKMEL 187 | WT | 35 | WM 1232 | BRAF (V600E) | 116 |
| mel 505 | WT | 35 | SKMEL 239 | BRAF (V600E) | 120 |
| PMWK | WT | 35 | MEL 224 | NRAS (Q61R) | 123 |
| SKMEL 103 | NRAS (Q61R) | 41 | A2058 | BRAF (V600E) | 130 |
| *NHM 11 | nd | 41 | SKMEL 115 | BRAF (V600E) | 151 |
| SKMEL 100 | BRAF (V600E) | 47 | RPMI 7951 | BRAF (V600E) | 152 |
| SBC 12 | NRAS (Q61K) | 47 | WM 1361A | NRAS (Q61R) | 174 |
| SKMEL 78 | WT | 47 | SKMEL 181 | BRAF (V600E) | 191 |
| A375 | BRAF (V600E) | 50 | WM 35 | BRAF (V600E) | 203 |
| SKMEL 28 | BRAF (V600E) | 52 | RPMI 8322 | WT | 218 |
| SKMEL 147 | NRAS (Q61R) | 55 | SKMEL 190 | BRAF (V600E) | 226 |
| SKMEL 27 | BRAF (V600E) | 57 | VMM 39 | NRAS (Q61R) | 297 |
| *NHM 12 | nd | 59 | SKMEL 119 | NRAS (Q61R) | 304 |
| SKMEL 173 | NRAS (Q61K) | 63 | MEL 537 | WT | 336 |
| SKMEL 24 | BRAF (V600E) | 64 | MALME 3M | BRAF (V600E) | 373 |
| WM 1158 | BRAF (V600E) | 64 | WM 2664 | BRAF (V600D) | 642 |
| SKMEL 130 | BRAF (V600E) | 66 | SKMEL 186 | NRAS (Q61K) | 1443 |
| UACC 257 | BRAF (V600E) | 69 | SKMEL 153 | BRAF (V600K) | 5550 |
| SKMEL 5 | WT | 73 | | | |

Abbreviation: nd; not done; *NHM normal human melanocyte culture; WT; wildtype (negative for BRAF and NRAS mutations).

Table 7A-7B. Results of the Statistical Analysis of ITK shRNA Effects on Proliferation and Motility Rates of Melanoma Cell Lines

TABLE 7A

Statistical Analysis of shRNA Melanoma Cell Lines Proliferation Rates

| PMWK (ITK$_{LO}$) | P value | RPMI 8322 (ITK$_{HI}$) | P value | VMM 39 (ITK$_{HI}$) | P value |
|---|---|---|---|---|---|
| SCR vs PMWK | 1.000 | SCR vs RPMI 8322 | 0.002 | SCR vs VMM 39 | 1.000 |
| ITK 4 vs PMWK | 0.011 | ITK 4 vs RPMI 8322 | <0.001 | ITK 4 vs VMM 39 | <0.001 |
| ITK 5 vs PMWK | 1.000 | ITK 5 vs RPMI 8322 | <0.001 | ITK 5 vs VMM 39 | <0.001 |
| ITK 6 vs PMWK | 1.000 | ITK 6 vs RPMI 8322 | 0.645 | ITK 6 vs VMM 39 | 1.000 |
| ITK 7 vs PMWK | 0.106 | ITK 7 vs RPMI 8322 | <0.001 | ITK 7 vs VMM 39 | <0.001 |

TABLE 7B

Statistical Analysis of shRNA Melanoma Cell Lines Motility Rates

| PMWK (ITK$_{LO}$) | P value | RPMI 8322 (ITK$_{HI}$) | P value | VMM 39 (ITK$_{HI}$) | P value |
|---|---|---|---|---|---|
| SCR vs PMWK | 1.000 | SCR vs RPMI 8322 | 0.355 | SCR vs VMM 39 | 0.048 |
| ITK 4 vs PMWK | 0.985 | ITK 4 vs RPMI 8322 | <0.001 | ITK 4 vs VMM 39 | <0.001 |
| ITK 5 vs PMWK | 1.000 | ITK 5 vs RPMI 8322 | <0.001 | ITK 5 vs VMM 39 | <0.001 |
| ITK 6 vs PMWK | 1.000 | ITK 6 vs RPMI 8322 | 1.000 | ITK 6 vs VMM 39 | 1.000 |
| ITK 7 vs PMWK | 0.935 | ITK 7 vs RPMI 8322 | <0.001 | ITK 7 vs VMM 39 | <0.001 |

Abbreviations: SCR, scrambled shRNA
T-tests with Bonferroni correction were conducted for each statistical analysis Table 8A-8C. Kinase Selectivity of BI 10N at Single Inhibitor Concentration and IC50s with ATP Concentration at Approximate Km for ATP and at 1 mM ATP

TABLE 8A

Screen at a Single Inhibitor Concentration

| Kinase | % Inhibition At 0.2 µM | Kinase | % Inhibition At 0.2 µM |
|---|---|---|---|
| ITK | 106.7 | IGF1R | 19 |
| TRKA | 106 | AurA | 15.9 |
| IRAK4 | 105.1 | AMPKα1/β1/γ1 | 15.3 |
| PDGFRα | 101.4 | PIM1 | 10.4 |
| HGK | 100.4 | EGFR | 8.6 |
| SRC | 99.9 | TIE2 | 8.2 |
| LCK | 96.7 | EPHA2 | 7.8 |
| ABL | 91.9 | p70S6K | 7.6 |
| MST1 | 91.7 | PKD2 | 7 |
| TSSK1 | 88.9 | DAPK1 | 5.5 |
| FGFR1 | 80.2 | PAK2 | 4.5 |
| DYRK1B | 79.6 | MET | 4.1 |
| KDR | 79.3 | PKACα | 2.5 |
| CK1ε | 76.2 | PBK | 1.7 |
| JAK3 | 75 | PDK1 | 1.5 |
| CDK2/CycA2 | 72.3 | SGK | 1.4 |
| CHK1 | 60.3 | NEK2 | 0.3 |
| EPHB4 | 52.1 | JNK2 | −0.1 |
| SYK | 40.6 | Erk2 | −1.5 |
| TYRO3 | 35.6 | AKT1 | −2.2 |
| PYK2 | 35.1 | IKKβ | −2.4 |
| ROCK1 | 33 | p38α | −4.1 |
| CSK | 32.4 | CaMK4 | −4.3 |
| GSK3β | 31.5 | MAPKAPK2 | −5.2 |

TABLE 8B

IC50s with the ATP Concentration at Approximately the Km for ATP

| | IC50(M) | |
|---|---|---|
| Kinase | BI 10N | Positive Control* |
| ITK | ** | 3.04E−09 |
| TRKA | ** | 4.21E−10 |
| YES | 9.93E−10 | 2.52E−09 |
| FGR | 2.89E−09 | 1.89E−09 |
| IRAK4 | 3.14E−09 | 1.01E−08 |
| SRC | 3.76E−09 | 4.98E−09 |
| PDGFRα | 1.01E−08 | 2.00E−10 |
| LCK | 1.06E−08 | 1.71E−09 |
| HGK | 1.21E−08 | 1.16E−09 |
| ABL | 2.35E−08 | 8.15E−08 |
| FYN | 2.42E−08 | 2.32E−09 |
| MST1* | 2.60E−08 | 3.43E−09 |
| TSSK1 | 2.86E−08 | 2.64E−10 |
| LYNa | 3.66E−08 | 2.18E−09 |
| LYNb | 4.30E−08 | 2.19E−09 |
| BLK | 5.22E−08 | 2.17E−09 |
| FGFR1 | 5.97E−08 | 2.98E−09 |
| IGF1R | 8.86E−07 | 3.98E−08 |
| ZAP70 | 7.09E−06 | 1.77E−09 |

*The positive control was Staurosporine for all enzymes except MST1, for which it was K252b.
**BI 10N is more potent than can be measured with this assay. The IC50 under these assay conditions is significantly lower than 5 E−10. Further analysis of the potency of BI 10N with these enzymes is presented in C.

TABLE 8C

IC50s at 1 mM ATP Concentration***

| | Km ATP | IC50(M) | | Calculated Apparent Km |
|---|---|---|---|---|
| Kinase | (µM) | BI 10 | Staurosporine | for BI 10N Binding |
| ITK | 6.1 | 1.43E−09 | 1.52E−07 | 8.65E−12 |
| TRKA | 65 | 8.28E−10 | 5.95E−10 | 5.05E−11 |
| TRKB | 80 | 1.28E−09 | 4.74E−10 | 9.47E−11 |
| TRKC | 47 | 1.58E−09 | 1.10E−09 | 7.08E−11 |
| YES | 13 | 5.90E−09 | 2.42E−08 | 7.57E−11 |

***The positive control was Staurosporine for all enzymes.

Table 9A-9B. Statistical Analysis of BI 10N Effects on Proliferation and Motility Rates of Melanoma Cell Lines

TABLE 9A

Effects of BI 10N at Different Concentrations on Proliferation Rate of Melanoma Cell Lines

| PMWK (ITK$_{LO}$) | P value | SKMEL 131 (ITK$_{LO}$) | P value | SKMEL 103 (ITK$_{INT}$) | P value | A375 (ITK$_{INT}$) | P value |
|---|---|---|---|---|---|---|---|
| 100 nM vs. 0 nM | 0.003 | 100 nM vs. 0 nM | 1.000 | 100 nM vs. 0 nM | <0.001 | 10 nM vs. 0 nM | <0.001 |
| 150 nM vs. 0 nM | 0.548 | 150 nM vs. 0 nM | 1.000 | 150 nM vs. 0 nM | <0.001 | 25 nM vs. 0 nM | <0.001 |
| 200 nM vs. 0 nM | <0.001 | 200 nM vs. 0 nM | 0.007 | 200 nM vs. 0 nM | 0.001 | 50 nM vs. 0 nM | 0.001 |
| | | 300 nM vs. 0 nM | <0.001 | | | 100 nM vs. 0 nM | <0.001 |
| | | 400 nM vs. 0 nM | <0.001 | | | 150 nM vs. 0 nM | <0.001 |
| | | | | | | 200 nM vs. 0 nM | <0.001 |

| RPMI 8322 (ITK$_{HI}$) | | VMM 39 (ITK$_{HI}$) | | SKMEL 153 (ITK$_{HI}$) | |
|---|---|---|---|---|---|
| 10 nM vs. 0 nM | 0.962 | 10 nM vs. 0 nM | 0.031 | 10 nM vs. 0 nM | 0.008 |
| 25 nM vs. 0 nM | 0.259 | 25 nM vs. 0 nM | <0.001 | 25 nM vs. 0 nM | 0.316 |
| 50 nM vs. 0 nM | <0.001 | 50 nM vs. 0 nM | <0.001 | 50 nM vs. 0 nM | <0.001 |
| 100 nM vs. 0 nM | <0.001 | 100 nM vs. 0 nM | <0.001 | | |
| 200 nM vs. 0 nM | <0.001 | | | | |

TABLE 9B

Effects of BI 10N at Different Concentration on Motility Rate of Melanoma Cell Lines

| PMWK (ITK$_{LO}$) | P value | SKMEL 131 (ITK$_{LO}$) | P value | SKMEL 103 (ITK$_{INT}$) | P value | A375 (ITK$_{INT}$) | P value |
|---|---|---|---|---|---|---|---|
| 10 nM vs. 0 nM | 1.000 | 100 nM vs. 0 nM | 0.001 | 100 nM vs. 0 nM | 0.004 | 100 nM vs. 0 nM | 0.620 |
| 25 nM vs. 0 nM | 1.000 | 150 nM vs. 0 nM | <0.001 | 150 nM vs. 0 nM | 1.000 | 150 nM vs. 0 nM | <0.001 |
| 50 nM vs. 0 nM | 1.000 | 200 nM vs. 0 nM | <0.001 | 200 nM vs. 0 nM | <0.001 | 200 nM vs. 0 nM | <0.001 |
| 100 nM vs. 0 nM | 0.195 | | | | | | |
| 150 nM vs. 0 nM | <0.001 | | | | | | |
| 200 nM vs. 0 nM | <0.001 | | | | | | |

| RPMI 8322 (ITK$_{HI}$) | | VMM 39 (ITK$_{HI}$) | | SKMEL 153 (ITK$_{HI}$) | |
|---|---|---|---|---|---|
| 10 nM vs. 0 nM | 1.000 | 10 nM vs. 0 nM | <0.001 | 10 nM vs. 0 nM | <0.001 |
| 25 nM vs. 0 nM | <0.001 | 25 nM vs. 0 nM | <0.001 | 25 nM vs. 0 nM | <0.001 |
| 50 nM vs. 0 nM | <0.001 | 50 nM vs. 0 nM | <0.001 | 50 nM vs. 0 nM | <0.001 |

T-tests with Bonferroni corrections were conducted for each statistical analysis

TABLE 10

ITK Protein Levels by Immunohistochemistry by Clinical and Hormone Receptor Characteristics of Breast Cancer

| Characteristic | Sample Size | Mean ITK Level |
|---|---|---|
| All specimens in each category | 54 | 247.24 |
| Sex | | |
| Female | 54 | 247.24 |
| Race | | |
| White | 25 | 267.14 |
| Black | 26 | 208.54 |
| Hispanic | 3 | 416.84 |
| P value, Kruskal-Wallis | | 0.27 |
| Age at diagnosis of primary breast cancer | | |
| ≤40 yrs | 11 | 199.98 |
| >40 yrs | 43 | 259.33 |
| P value, Wilcoxon rank-sum | | 0.71 |
| Menopausal status at diagnosis | | |
| Pre-menopausal | 23 | 221.11 |
| Post-menopausal | 31 | 266.63 |
| P value, Wilcoxon rank-sum | | 0.83 |
| ER Status | | |
| ER− | 21 | 401.22 |
| ER+ | 32 | 151.13 |
| Borderline | 1 | — |
| P value, Wilcoxon rank-sum | | 0.0007 |
| PR Status | | |
| PR− | 30 | 350.68 |
| PR+ | 19 | 92.09 |
| Borderline | 5 | 216.15 |
| P value, Kruskal-Wallis | | 0.003 |
| ER and PR Status Combined | | |
| ER− and PR− | 20 | 418.84 |
| (ER− and PR+) or (ER+ and PR−) | 11 | 199.32 |
| ER+ and PR+ | 18 | 94.50 |
| Unknown | 5 | — |
| P value, Kruskal-Wallis | | 0.0004 |
| Her2 Status | | |
| Her2− | 35 | 248.77 |
| Her2+ | 16 | 231.98 |
| Borderline | 1 | — |
| Unknown | 2 | — |
| P value, Wilcoxon rank-sum | | 0.87 |
| IHC Subtype | | |
| Luminal A | 22 | 158.95 |
| Luminal B | 10 | 139.21 |
| Her2 /ER− | 6 | 386.61 |
| Basal/TN | 13 | 400.77 |
| Unknown | 3 | — |
| P value, Kruskal-Wallis | | 0.011 |

Abbreviations: ER, estrogen receptor; PR, progesterone receptor; SLN, sentinal lymph node; HR, hormone receptor (estrogen or progesterone).

TABLE 11A

Source of Primary and Secondary antibodies

| Antibody | Type | Company | Catalogue number |
|---|---|---|---|
| ITK | rabbit monoclonal, Y401 | Abcam | ab32039 |
| ITK (for mouse tumor staining) | rabbit polyclonal | Abcam | ab32113 |
| GAPDH | mouse monoclonal | Abcam | ab9484 |
| ERK | rabbit monoclonal | Cell Signaling | #4695 |
| pERK | rabbit monoclonal, Thr202/Thr204 | Cell Signaling | #4370 |
| AKT | rabbit monoclonal | Cell Signaling | #4691 |
| pAKT | rabbit monoclonal Ser473 | Cell Signaling | #3787 |
| PD-L1 | rabbit polyclonal | ProSci, Inc. | 4059 |
| PTEN | mouse monoclonal, 6H2.1 | Millipore | 04-035 |
| CD3 | mouse monoclonal | Leica | clone 514H12 |
| CD19 | mouse monoclonal | Leica | clone BT51E |

TABLE 11A-continued

Source of Primary and Secondary antibodies

| Antibody | Type | Company | Catalogue number |
|---|---|---|---|
| CD68 | mouse monoclonal | Leica | clone 514H12 |
| myeloperoxidase (MPO) | mouse monoclonal | Leica | clone 59A5 |
| Mast Cell Tryptase (MCT) | mouse monoclonal | Leica | clone 10D11 |
| CD56 | mouse monoclonal | Leica | CD564 |
| CD57 | mouse monoclonal | Leica | clone NK-1 |
| S100 | rabbit polyclonal | Dako | Z0311 |
| S100 | mouse monoclonal S1/61/69 | Leica | NCL-S100 |
| phospho-BTK | Rabbit monoclonal | Epitomics | 1685-1 |
| phospho-BTK | Mouse monoclonal | BD Biosciences | 558034 |
| VE1 | Mouse Monoclonal to BRAF V600E | Spring Bioscience | E19290 |
| Alexa555 labeled goat anti rabbit | | Invitrogen | A21429 |
| Alexa555 labeled goat anti mouse | | Invitrogen | A21424 |
| EnVision ™ anti mouse HRP | | Dako | K4001 |

TABLE 11B

Staining Protocols for Antibodies

| Primary Antibodies | Automatic vs. manual | Detection | Bond-epitope retrieval solution | Satining protocol | Dilution incubation time of primary antibodies |
|---|---|---|---|---|---|
| ITKr(1) | Automatic | Chromogenic | Solution 2 pH9.0 | single | 1:3000, 1 h |
| ITKr(2) | Automatic | Fluorescence | Solution 2 pH9.0 | single | 1:3000, 1 h |
| P-AKTr + S100m | Automatic | Fluorescence | Solution 1 pH6.0 | cocktail | 1:10, 12 h (P-AKT) 1:25, 12 h (S100) |
| P-ERKr + S100m | Automatic | Fluorescence | Solution 1 pH6.0 | cocktail | 1:200, 1 h (P-ERK) 1:25, 6 h (S100) |
| ITKr + S100r | Automatic | Fluorescence | Solution 2 pH9.0 (ITK) Solution 1 pH6.0 (S100r) | sequential | 1:3000, 1 h (ITK) 1:1600, 1 h (S100) |
| PDL-1r + S100r | Automatic | Fluorescence | Solution 1 pH6.0 | sequential | 1:400, 1 h (PDL-1) 1:1600, 2 h (S100) |
| PTENm + S100r | Automatic | Fluorescence | Solution 2 pH9.0 (ITK) Solution 1 pH6.0 (PTEN) | sequential | 1:3000, 15 min (PTEN) 1:1600, 1 h (S100) |
| ITKr + CD3m | Automatic | Fluorescence | Solution 2 pH9.0 | sequential | 1:3000, 1 h (ITK) RTU, 1 h (CD3) |
| ITKr + CD19m | Automatic | Fluorescence | Solution 2 pH9.0 (ITK) Solution 1 pH6.0 (CD19) | sequential | 1:3000, 1 h (ITK). RTU, 1 h (CD19) |
| ITKr + CD68m | Automatic | Fluorescence | Solution 2 pH9.0 | sequential | 1:3000, 1 h (ITK) RTU, 1 h (CD68) |
| ITKr + MPOm | Automatic | Fluorescence | Solution 2 pH9.0 (ITK) Solution 1 pH6.0 (MPO) | sequential | 1:3000, 1 h (ITK) 1:200, 15 min (MPO) |
| ITKr + MCTm | Automatic | Fluorescence | Solution 2 pH9.0 (ITK) Solution 1 pH6.0 (MCT) | sequential | 1:3000, 1 h (ITK) RTU, 15 min (MCT) |
| ITKr + CD56m | Automatic | Fluorescence | Solution 2 pH9.0 (ITK) Solution 1 pH6.0 (CD56) | sequential | 1:3000, 1 h (ITK). RTU, 1 h (CD56) |
| ITKr + CD57m | Automatic | Fluorescence | Solution 2 pH9.0 (ITK) Solution 1 pH6.0 (CD57) | sequential | 1:3000, 1 h (ITK) 1:100, 15 min (CD57) |

TABLE 11B-continued

Staining Protocols for Antibodies

| Primary Antibodies | Automatic vs. manual | Detection | Bond-epitope retrieval solution | Satining protocol | Dilution incubation time of primary antibodies |
|---|---|---|---|---|---|
| VE1 | Automatic | Chromogenic | Solution 2 pH9.0 with EDTA, 30 mins | single | 1:100, 30 mins |
| ITKr* | Manual | Chromogenic | AR-10 (HK057-5K, BioGenex) | single | 1:100, 1 h | m-mouse host, r-rabbit host, RTU (Ready To Use)
*ITK abcam ab32113 for staining mouse tumors.

TABLE 11C

Staining Protocols for Antibodies

| Primary Antibodies | Peroxide block between two stains | Nuclear stain | Detection: secondary antibodies and fluorophore |
|---|---|---|---|
| ITKr(1) | N/A | Hematoxylin (Bond kit DS9800) | Bond polymer (Bond kit DS9800), DAB (Bond kit DS9800) |
| ITKr(2) | N/A | DAPI (P36935, Molecular Probes) | Bond polymer (DS9800), Tyramide Cy5 |
| P-AKTr + S100m | N/A | Hoechst 33258 (Invitrogen) | (P-AKT) Bond polymer (DS9800) + Tyramide Cy5 (PerkinElmer). (S100) Goat anti-mouse-Alexa555 |
| P-ERKr + S100m | N/A | DAPI (P36935, Molecular Probes) | (P-ERK) Bond polymer (DS9800) + Tyramide Cy5 (PerkinElmer). (S100) Goat anti-mouse-Alexa555 |
| ITKr + S100r | no | DAPI (P36935, Molecular Probes) | (ITK) Bond polymer (DS9800) + Tyramide Cy5 (PerkinElmer). (S100) goat anti-rabbit-Alexa555 |
| PDL-1r + S100r | no | Hoechst 33258 (Invitrogen) | (PDL-1) Bond polymer (DS9800) + Tyramide Cy5 (PerkinElmer). (S100) goat anti-rabbit-Alexa555 |
| PTENm + S100r | no | Hoechst 33258 (Invitrogen) | (PTEN) Bond polymer (DS9800) + Tyramide Cy5 (PerkinElmer). (S100) goat anti-rabbit-Alexa555 |
| ITKr + CD3m | yes | Hoechst 33258 (Invitrogen) | (ITK) Bond polymer (DS9800) + Tyramide Cy5 (PerkinElmer). (CD3) DAKO-EnVision ™ mouse + Tyramide Cy3 |
| ITKr + CD19m | yes | Hoechst 33258 (Invitrogen) | (ITK) Bond polymer (DS9800) + Tyramide Cy5 (Perkin Elmer). (CD19) DAKO-EnVision ™ mouse + Tyramide Cy3 (Perkin Elmer) |
| ITKr + CD68m | yes | Hoechst 33258 (Invitrogen) | (ITK) Bond polymer (DS9800) + Tyramide Cy5 (PerkinElmer). (CD68) DAKO-EnVision ™ mouse + Tyramide Cy3 |
| ITKr + MPOm | yes | Hoechst 33258 (Invitrogen) | (ITK) Bond polymer (DS9800) + Tyramide Cy5 (PerkinElmer). (CDMPO) DAKO-EnVision ™ mouse + Tyramide Cy3 |
| ITKr + MCTm | yes | Hoechst 33258 (Invitrogen) | (ITK) Bond polymer (DS9800) + Tyramide Cy5 (PerkinElmer). (MCT) DAKO-EnVision ™ mouse + Tyramide Cy3 |
| ITKr + CD56m | yes | Hoechst 33258 (Invitrogen) | (ITK) Bond polymer (DS9800) + Tyramide Cy5 (Perkin Elmer). (CD56) DAKO-EnVision ™ mouse + Tyramide Cy3 (Perkin Elmer) |
| ITKr + CD57m | yes | Hoechst 33258 (Invitrogen) | (ITK) Bond polymer (DS9800) + Tyramide Cy5 (PerkinElmer). (CD57) DAKO-EnVision ™ mouse + Tyramide Cy3 |
| VE1 | N/A | Hematoxylin (Dako S3301) | Leica Refined Red polymer detection system (Leica Microsystems) |
| ITKr* | N/A | Hematoxylin (Dako S3301) | Biogenex SuperSensitive ™ Link-Label IHC Detection System (LA000-UL, Biogenex) |

7. REFERENCES

1. Becker, K. G., White, S. L., Muller, J., and Engel, J. (2000). BBID: the biological biochemical image database. Bioinformatics 16, 745-746
2. Berg, L J., et al., *Tec family kinases in T lymphocyte development and function*. Annu Rev Immunol, 2005. 23:549-600.
3. Callahan, M. K., and Wolchok, J. D. (2013). At the bedside: CTLA-4- and PD-1-blocking antibodies in cancer immunotherapy. Journal of leukocyte biology 94, 41-53
4. Carson C, Omolo B, Chu H, Zhou Y, Sambade M J, Peters E C, Tompkins P, Simpson D A, Thomas N E, Fan C, Sarasin A, Dessen P, Shields J M, Ibrahim J G, Kaufmann W K *A prognostic signature of defective p53-dependent G1 checkpoint function in melanoma cell lines*. Pigment Cell Melanoma Res., 2012. 25(4):514-526.
5. Casaletto J. B. and McClatchey A. I. *Spatial regulation of receptor tyrosine kinases in development and cancer*, Nat Rev Cancer, 2012. 12(6):387-400.
6. Chapman, P. B., et al., *Improved survival with vemurafenib in melanoma with BRAF V600E mutation*. N Engl J Med., 2011. 364(26):2507-16.
7. Conway K, Edmiston S N, Khondker Z S, Groben P A, Zhou X, Chu H, Kuan P F, Hao H, Carson C, Berwick M, Olilla D W, Thomas N E. *DNA-methylation profiling distinguishes malignant melanomas from benign nevi*. Pigment Cell Melanoma Res., 2011. 24(2):352-60.
8. Dai, M., Wei, H., Yip, Y. Y., Feng, Q., He, K., Popov, V., Hellstrom, I., and Hellstrom, K. E. (2013). Long-lasting complete regression of established mouse tumors by counteracting Th2 inflammation. J Immunother 36, 248-257
9. Davies M A. *The role of the PI3K-AKT pathway in melanoma*. Cancer J., 2012. 18(2):142-7.
10. Dankort, D., et al., *Braf(V600E) cooperates with Pten loss to induce metastatic melanoma*. Nat Genet., 2009. 41(5):544-52.
11. Eggermont, A. M. M., Robert, C. *New Drugs in Melanoma: It's a Whole New World*. European Journal of Cancer, 2011. 47: 2150-2156.
12. Fischer, A. M., Mercer, J. C., Iyer, A., Ragin, M. J., and August, A. (2004). Regulation of CXC chemokine receptor 4-mediated migration by the Tec family tyrosine kinase ITK. J Biol Chem 279, 29816-29820
13. Hodi, F. S., et al., *Improved survival with ipilimumab in patients with metastatic melanoma*. N Engl J Med., 2010. 363(8):711-23.
14. Gomez-Rodriguez, J., Kraus, Z J., and Schwartzberg, P. L. (2011). Tec family kinases Itk and Rlk/Txk in T lymphocytes: cross-regulation of cytokine production and T-cell fates. The FEBS journal 278, 1980-1989
15. Guo W, Liu R, Ono Y, Ma A H, Martinez A, Sanchez E, Wang Y, Huang W, Mazloom A, Li J, Ning J, Maverakis E, Lam K S, Kung H J. *Molecular Characteristics of CTA056, a Novel Interleukin-2-Inducible T-Cell Kinase Inhibitor that Selectively Targets Malignant T Cells and Modulates Oncomirs*. Mol Pharmacol. 2012 November; 82(5):938-47.
16. Igney, F. H., and Krammer, P. H., *Immune Escape of Tumors: Apoptosis Resistance and Tumor Counterattack*. J Leukoc Biol., 2002. 7(16):907-920.
17. Kanehisa, M., Goto, S., Kawashima, S., Okuno, Y., and Hattori, M. (2004). The KEGG resource for deciphering the genome. Nucleic Acids Res 32, D277-280
18. Kaufmann, W. K., Nevis, K. R., Qu, P. et al., (2008). *Defective cell cycle checkpoint functions in melanoma are associated with altered patterns of gene expression*. J. Invest. Dermatol. 2008. 128:175-187.
19. Key M (ed). Education Guide: Immunohistochemical Staining Methods. 4th ed. Dako 2006.
20. Lo, H. Y., *Itk inhibitors: a patent review*. Expert Opin Ther Pat., 2010. 20(4):459-69.
21. McArthur, G. A., and Ribas, A. (2013). Targeting oncogenic drivers and the immune system in melanoma. J Clin Oncol 31, 499-506.
22. Meganathan C, Sakkiah S, Lee Y, Narayanan J V, Lee K W. *Discovery of potent inhibitors for interleukin-2-inducible T-cell kinase: structure-based virtual screening and molecular dynamics simulation approaches*. J Mol Model. 2012. Sep. 27. [Epub ahead of print]
23. Mi, H., Guo, N., Kejariwal, A., and Thomas, P. D. (2007). PANTHER version 6: protein sequence and function evolution data with expanded representation of biological pathways. Nucleic Acids Res 35, D247-252
24. Patel, S. P. and K. B. Kim, *Selumetinib (AZD6244; ARRY-142886) in the treatment of metastatic melanoma*. Expert Opin Investig Drugs, 2012. 21(4):531-9.
25. Riether D, Zindell R, Kowalski J A, Cook B N, Bentzien J, Lombaert S D, Thomson D, Kugler S Z Jr, Skow D, Martin L S, Raymond E L, Khine H H, O'Shea K, Woska J R Jr, Jeanfavre D, Sellati R, Ralph K L, Ahlberg J, Labissiere G, Kashem M A, Pullen S S, Takahashi H. *5-Aminomethylbenzimidazoles as potent ITK antagonists* Bioorg Med Chem Lett., 2009. 19(6):1588-91.
26. Roberts P J, Usary J E, Darr D B, Dillon P M, Pfefferle A D, Whittle M C, Duncan J S, Johnson S M, Combest A J, Jin J, Zamboni W C, Johnson G L, Perou C M, Sharpless N E., *Combined PI3K/mTOR and MEK Inhibition Provides Broad Antitumor Activity in Faithful Murine Cancer Models*. Clin Cancer Res., 2012. 18(19): 5290-5303.
27. Sahu N, August A. *ITK inhibitors in inflammation and immune-mediated disorders*. Curr Top Med Chem. 2009; 9(8):690-703.
28. Schaefer, C. F., Anthony, K., Krupa, S., Buchoff, J., Day, M., Hannay, T., and Buetow, K. H. (2009). PID: the Pathway Interaction Database. Nucleic Acids Res 37, D674-679
29. Shi, S. R., et al., *Antigen Retrieval immunohistochemistry under the influence of pH using monoclonal antibodies*. J Histochem Cytochem 43:193-201, 1995.
30. Siegel R, Naishadham D, Jemal A. *Cancer statistics*, 2012. CA Cancer J Clin., 2012. 62(1):10-29.
31. Taube, J. M., Anders, R. A., Young, G. D., Xu, H., Sharma, R., McMiller, T. L., Chen, S., Klein, A. P., Pardoll, D. M., Topalian, S. L., and Chen, L. (2012). Colocalization of inflammatory response with B7-h1 expression in human melanocytic lesions supports an adaptive resistance mechanism of immune escape. Sci Transl Med 4, 127ra137
32. Thomas N E, Edmiston S N, Alexander A, Millikan R C, Groben P A, Hao H, Tolbert D, Berwick M, Busam K, Begg C B, Mattingly D, Ollila D W, Tse C K, Hummer A, Lee-Taylor J, Conway K. *Number of nevi and early-life ambient UV exposure are associated with BRAF-mutant melanoma*. Cancer Epidemiol Biomarkers Prev 2007. 16:991-997.
33. Velankar A D, Quintini G, Prabhu A, Weber A, Hunaeus G, Voland B, Wuest M, Orjeda C, Harel D, Varghese S, Gore V, Patil M, Gayke D, Herdemann M, Heit I, Zaliani A. Synthesis and biological evaluation of novel (4 or 5-aryl)pyrazolyl-indoles as inhibitors of interleukin-2 inducible T-cell kinase (ITK). Bioorg Med Chem. 2010 Jun. 15; 18(12):4547-59. Epub 2010 Apr. 24.
34. Williams H C, San Martin A, Adamo C M, Seidel-Rogol B, Pounkova L, Datla S R, Lassègue B, Bear J E, Griendling K. *Role of Coronin 1B in PDGF-Induced Migration of Vascular Smooth Muscle Cells*. Circ Res. 2012. 111(1):56-65.

35. Woods M L, Kivens W J, Adelsman M A, Qiu Y, August A, and Shimizu Y. *A novel function for the Tec family tyrosine kinase Itk in activation of beta 1 integrins by the T-cell receptor*. EMBO J. 2001. 20:1232-1244.

36. Wu, C., Asokan, S. B., Berginski, M. E., Haynes, E. M., Sharpless, N. E., Griffith, J. D., Gomez, S. M., and Bear, J. E. (2012). Arp2/3 is critical for lamellipodia and response to extracellular matrix cues but is dispensable for chemotaxis. Cell 148, 973-987

37. Zapf C W, Gerstenberger B S, Xing L, Limburg D C, Anderson D R, Caspers N, Han S, Aulabaugh A, Kurumbail R, Shakya S, Li X, Spaulding V, Czerwinski R M, Seth N, Medley Q G. *Covalent Inhibitors of Interleukin-2 Inducible T Cell Kinase (Itk) with Nanomolar Potency in a Whole-Blood Assay*. J Med Chem. 2012 Nov. 12. [Epub ahead of print]

It is to be understood that, while the invention has been described in conjunction with the detailed description, thereof, the foregoing description is intended to illustrate and not limit the scope of the invention. Other aspects, advantages, and modifications of the invention are within the scope of the claims set forth below. All publications, patents, and patent applications cited in this specification are herein incorporated by reference as if each individual publication or patent application were specifically and individually indicated to beincorporated by reference.

What is claimed is:

1. A method of inhibiting the growth of a solid tumor in a subject which comprises administering an effective amount of a selective interleukin-2 inducible T-cell kinase (ITK) inhibitor to the subject wherein the selective ITK inhibitor is a benzimidazole having the formula

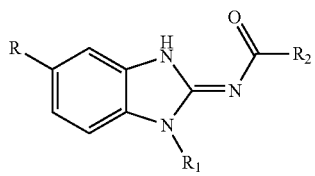

R is alkenyl, alkoxy, alkyl, alkyl(aryl), alkynyl, amino, aryl, cycloalkyl, halogen, hydroxyl, heteroaryl, heterocycloalkyl, or nitro;

$R_1$ is alkenyl, alkyl, alkyl(aryl), alkynyl, aryl, heteroaryl, or heterocycloalkyl; and $R_2$ is alkenyl, alkyl, alkyl(aryl), alkynyl, amino, aryl, cycloalkyl, hydroxyl, heterocycloalkyl, nitro, thiophenyl cycloalkyl, thiophenyl heteroaryl, or thiophenyl heterocycloalkyl.

2. The method of claim 1, wherein the solid tumor is a breast, a gastric, a head and neck, a kidney, a liver, a lung, a melanoma, a non-small cell lung cancer (NSCLC), a pancreatic, or a uterine tumor.

3. The method of claim 2, wherein the melanoma tumor is a primary melanoma tumor.

4. The method of claim 2, wherein the melanoma tumor is a melanoma metastasis tumor.

5. The method of claim 2, wherein the breast tumor is an estrogen receptor negative (ER(-)) or a progesterone receptor negative (PR(-)) breast tumor.

6. The method of claim 1, wherein the benzimidazole is

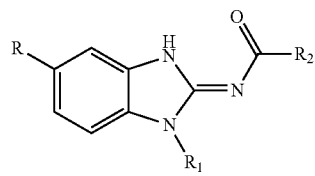

R is alkenyl, alkoxy, alkyl, alkyl(aryl), alkynyl, amino, aryl, cycloalkyl, halogen, heteroaryl, or heterocycloalkyl;

$R_1$ is alkyl, alkyl(aryl), alkynyl, aryl, heteroaryl, or heterocycloalkyl; and $R_2$ is alkenyl, alkyl, alkyl(aryl), alkynyl, amino, aryl, cycloalkyl, heteroaryl, heterocycloalkyl, thiophenyl cycloalkyl, thiophenyl heteroaryl or thiophenyl heterocycloalkyl.

7. The method of claim 6, wherein the benzimidazole is

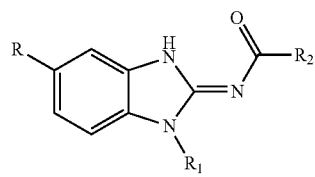

R is alkyl, alkyl(aryl), amino, heteroaryl, or heterocycloalkyl;

$R_1$ is alkyl; and $R_2$ is aryl, heteroaryl, heterocycloalkyl, thiophenyl cycloalkyl, thiophenyl heteroaryl or thiophenyl heterocycloalkyl.

8. The method of claim 7, wherein the benzimidazole is

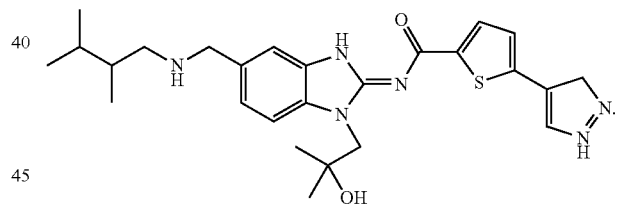

9. A method of inhibiting melanoma cell motility in a subject which comprises administering an effective amount of a selective interleukin-2 inducible T-cell kinase (ITK) inhibitor to the subject wherein the selective ITK inhibitor is a benzimidazole having the formula

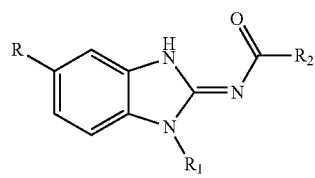

R is alkenyl, alkoxy, alkyl, alkyl(aryl), alkynyl, amino, aryl, cycloalkyl, halogen, hydroxyl, heteroaryl, heterocycloalkyl, or nitro;

$R_1$ is alkenyl, alkyl, alkyl(aryl), alkynyl, aryl, heteroaryl, or heterocycloalkyl; and R₂ is alkenyl, alkyl, alkyl(aryl), alkynyl, amino, aryl, cycloalkyl, hydroxyl, heterocycloalkyl, nitro, thiophenyl cycloalkyl, thiophenyl heteroaryl, or thiophenyl heterocycloalkyl.

10. A method of maintaining a cell in a G0/G1 cell cycle which comprises administering to the cell an effective amount of a selective interleukin-2inducible T-cell kinase (ITK) inhibitor wherein the selective ITK inhibitor is a benzimidazole having the formula

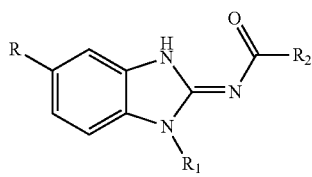

R is alkenyl, alkoxy, alkyl, alkyl(aryl), alkynyl, amino, aryl, cycloalkyl, halogen, hydroxyl, heteroaryl, heterocycloalkyl, or nitro;

R₁ is alkenyl, alkyl, alkyl(aryl), alkynyl, aryl, heteroaryl, or heterocycloalkyl; and R₂ is alkenyl, alkyl, alkyl(aryl), alkynyl, amino, aryl, cycloalkyl, hydroxyl, heterocycloalkyl, nitro, thiophenyl cycloalkyl, thiophenyl heteroaryl, or thiophenyl heterocycloalkyl.

* * * * *